United States Patent
Chakka et al.

(10) Patent No.: US 7,754,711 B2
(45) Date of Patent: *Jul. 13, 2010

(54) PYRIDAZINE DERIVATIVES AND THEIR USE AS THERAPEUTIC AGENTS

(75) Inventors: Nagasree Chakka, Burnaby (CA); Mikhail Chafeev, Vancouver (CA); Sultan Chowdhury, Scarborough (CA); Jian-Min Fu, Burnaby (CA); Duanjie Hou, Burnaby (CA); Rajender Kamboj, Burnaby (CA); Vishnumurthy Kodumuru, Burnaby (CA); Shifeng Liu, Port Coquitlam (CA); Vandna Raina, Vancouver (CA); Shaoyi Sun, Vancouver (CA); Serguei Sviridov, Burnaby (CA); Michael D. Winther, Vancouver (CA); Zaihui Zhang, Vancouver (CA); Melwyn Abreo, Jamul (CA); Mark W. Holladay, San Diego, CA (US); Wenbao Li, San Diego, CA (US); Sengen Sun, San Diego, CA (US); Chi Tu, San Diego, CA (US); Heinz W. Gschwend, Santa Rosa, CA (US)

(73) Assignee: Xenon Pharmaceuticals Inc., Burnaby, British Columbia (CA)

( * ) Notice: Subject to any disclaimer, the term of this patent is extended or adjusted under 35 U.S.C. 154(b) by 480 days.

This patent is subject to a terminal disclaimer.

(21) Appl. No.: 11/055,034

(22) Filed: Feb. 9, 2005

(65) Prior Publication Data

US 2006/0009459 A1  Jan. 12, 2006

Related U.S. Application Data

(63) Continuation-in-part of application No. 10/901,563, filed on Jul. 29, 2004, now Pat. No. 7,335,658.

(60) Provisional application No. 60/553,491, filed on Mar. 16, 2004, provisional application No. 60/553,404, filed on Mar. 16, 2004, provisional application No. 60/553,403, filed on Mar. 16, 2004, provisional application No. 60/553,446, filed on Mar. 16, 2004, provisional application No. 60/553,416, filed on Mar. 16, 2004, provisional application No. 60/546,815, filed on Feb. 23, 2004, provisional application No. 60/546,898, filed on Feb. 23, 2004, provisional application No. 60/546,786, filed on Feb. 23, 2004, provisional application No. 60/546,934, filed on Feb. 23, 2004, provisional application No. 60/491,095, filed on Jul. 30, 2003.

(51) Int. Cl.
A61K 31/551 (2006.01)
A61K 31/5513 (2006.01)
A61K 31/50 (2006.01)
A61K 31/502 (2006.01)
A61K 31/501 (2006.01)
C07D 245/02 (2006.01)
C07D 243/04 (2006.01)
C07D 243/08 (2006.01)
C07D 403/04 (2006.01)
C07D 401/14 (2006.01)
C07D 403/14 (2006.01)
A61P 7/12 (2006.01)

(52) U.S. Cl. .............. 514/218; 540/470; 540/492; 540/575; 544/238; 514/252.01; 514/252.02

(58) Field of Classification Search ............... 514/183, 514/218, 252.13, 252.01, 252.02; 540/470, 540/492, 575; 544/238
See application file for complete search history.

(56) References Cited

U.S. PATENT DOCUMENTS

| 5,001,125 | A | * | 3/1991 | Stokbroekx et al. | ..... 514/252.02 |
|---|---|---|---|---|---|
| 5,883,094 | A | * | 3/1999 | Fliri et al. | ............... 514/242 |
| 5,985,878 | A | * | 11/1999 | Stokbroekx et al. | ..... 514/252.02 |
| 7,119,086 | B2 | * | 10/2006 | Di Malta et al. | ............. 514/218 |

FOREIGN PATENT DOCUMENTS

| EP | 0-156-433 | 10/1985 |
|---|---|---|
| EP | 0-211-457 | 2/1987 |
| EP | 0-320-032 | 6/1989 |
| EP | 1-396-487 | 3/2004 |
| WO | WO-97/37975 | 10/1997 |
| WO | WO-99/00386 | 1/1999 |
| WO | WO-01/62954 | 8/2001 |

(Continued)

OTHER PUBLICATIONS

Dobrzyn, et al., Obesity Reviews 6, 169-174, 2005.*

(Continued)

*Primary Examiner*—Mark L Berch
*Assistant Examiner*—Cecilia M Jaisle
(74) *Attorney, Agent, or Firm*—Osha • Liang LLP

(57) ABSTRACT

Methods of treating an SCD-mediated disease or condition in a mammal, preferably a human, are disclosed, wherein the methods comprise administering to a mammal in need thereof a compound of formula (Ia):

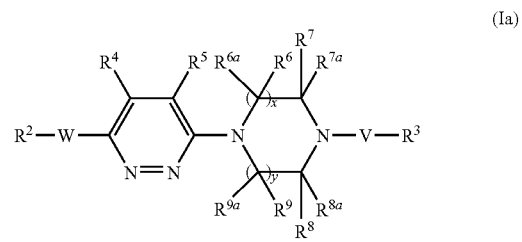

(Ia)

where x, y, W, V, $R^2$, $R^3$, $R^4$, $R^5$, $R^6$, $R^{6a}$, $R^7$, $R^{7a}$, $R^8$, $R^{8a}$, $R^9$ and $R^{9a}$ are defined herein. Pharmaceutical compositions comprising the compounds of formula (I) are also disclosed.

6 Claims, No Drawings

FOREIGN PATENT DOCUMENTS

| | | | |
|---|---|---|---|
| WO | WO-02/10154 | | 2/2002 |
| WO | WO 03/066604 | * | 2/2003 |
| WO | WO 03/105853 | * | 12/2003 |
| WO | WO 2004/011441 | * | 2/2004 |
| WO | WO 2004/058754 | * | 7/2004 |
| WO | WO-2005/011653 | | 2/2005 |
| WO | WO-2005/011655 | | 2/2005 |
| WO | WO-2005/011657 | | 2/2005 |

OTHER PUBLICATIONS

Giutiérrez-Juárez, et al., J. Clin. Invest., vol. 116, No. 6, Jun. 2006, pp. 1686-1695.*

Sjogren, et al., Diabetologia (2008) 51:328-335.*

Warensjo, et al., Obesity, vol. 15, No. 7, Jul. 2007, 1732-1740.*

PCT International Search Report and Written Opinion, regarding International Application No. PCT/US2006/004389, dated Aug. 3, 2006 (13 pages).

Office Action dated Dec. 19, 2006, from the U.S. Patent and Trademark Office for related U.S. Appl. No. 10/901,563 (24 pages).

English translation of Office Action and Search Report issued by the Taiwan Patent Office on Sep. 10, 2008, in related Taiwan Application No. 095104384 (3 pages).

Notice of Allowance and Fee(s) Due issued Sep. 20, 2007, by the U.S. Patent and Trademark Office in related U.S. Appl. No. 10/901,563 (5 pages).

Official Action dated Jan. 27, 2009, issued by the Canadian Patent Office in related-Canadian Patent Application No. 2,533,899 (3 pages).

* cited by examiner

PYRIDAZINE DERIVATIVES AND THEIR USE AS THERAPEUTIC AGENTS

CROSS REFERENCE TO RELATED APPLICATIONS

This application is a continuation-in-part of U.S. patent application Ser. No. 10/901,563, filed Jul. 29, 2004, which claimed priority to U.S. Provisional Patent Application Ser. No. 60/491,095, filed Jul. 30, 2003; U.S. Provisional Patent Application Ser. No. 60/546,820, filed Feb. 23, 2004; U.S. Provisional Patent Application Ser. No. 60/553,416, filed Mar. 16, 2004; U.S. Provisional Patent Application Ser. No. 60/546,934, filed Feb. 23, 2004; U.S. Provisional Patent Application Ser. No. 60/553,446, filed Mar. 16, 2004; U.S. Provisional Patent Application Ser. No. 60/546,786, filed Feb. 23, 2004; U.S. Provisional Patent Application Ser. No. 60/553,403, filed Mar. 16, 2004; U.S. Provisional Patent Application Ser. No. 60/546,898, filed Feb. 23, 2004; U.S. Provisional Patent Application Ser. No. 60/553,404, filed Mar. 16, 2004; U.S. Provisional Patent Application Ser. No. 60/546,815, filed Feb. 23, 2004; and U.S. Provisional Patent Application Ser. No. 60/553,491, filed Mar. 16, 2004; the disclosures of which are hereby incorporated by reference in their entireties. This application also claims the priority benefit of PCT Application, PCT/US2004/024658, filed Jul. 29, 2004, which claimed priority to U.S. Provisional Patent Application Ser. No. 60/491,095, filed Jul. 30, 2003, the disclosures of which are hereby incorporated by reference in their entireties.

FIELD OF THE INVENTION

The present invention relates generally to the field of inhibitors of stearoyl-CoA desaturase, such as pyridazine derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

BACKGROUND OF THE INVENTION

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the delta-9, delta-6, and delta-5 positions. Stearoyl-CoA desaturases (SCDs) introduce a double bond in the $C_9$-$C_{10}$ position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (Jeffcoat, R. et al., *Elsevier Science* (1984), Vol. 4, pp. 85-112; de Antueno, R J, *Lipids* (1993), Vol. 28, No. 4, pp. 285-290), it has only recently been directly implicated in human disease processes.

A single SCD gene, SCD1, has been characterized in humans. SCD1 is described in Brownlie et al, PCT published patent application, WO 01/62954, the disclosure of which is hereby incorporated by reference in its entirety. A second human SCD isoform has recently been identified, and because it bears little sequence homology to alternate mouse or rat isoforms it has been named human SCD5 or hSCD5 (PCT published patent application, WO 02/26944, incorporated herein by reference in its entirety).

To date, no small-molecule, drug-like compounds are known that specifically inhibit or modulate SCD activity. Certain long-chain hydrocarbons have been used historically to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA while cis-9, trans-11 conjugated linoleic acid does not. Cyclopropenoid fatty acids, such as those found in stercula and cotton seeds, are also known to inhibit SCD activity. For example, sterculic acid (8-(2-octylcyclopropenyl)octanoic acid) and malvalic acid (7-(2-octylcyclopropenyl)heptanoicacid) are C18 and C16 derivatives of sterculoyl and malvaloyl fatty acids, respectively, having cyclopropene rings at their C9-C10 position. These agents are believed to inhibit SCD enzymatic activity by direct interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety.

These known modulators of delta-9 desaturase activity are not useful for treating the diseases and disorders linked to SCD1 biological activity. None of the known SCD inhibitor compounds are selective for SCD or delta-9 desaturases, as they also inhibit other desaturases and enzymes. The thia-fatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids.

The absence of small molecule inhibitors of SCD enzyme activity is a major scientific and medical disappointment because evidence is now compelling that SCD activity is directly implicated in common human disease processes: See e.g., Attie, A. D. et al., "Relationship between stearoyl-CoA desaturase activity and plasma triglycerides in human and mouse hypertriglyceridemia", J. Lipid Res. (2002), Vol. 43, No. 11, pp. 1899-907; Cohen, P. et al., "Role for stearoyl-CoA desaturase-1 in leptin-mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. USA*. (2002), Vol. 99, No. 7, pp. 11482-6.

The present invention solves this problem by presenting new classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

Related Literature

U.S. Pat. No. 6,677,452 discloses novel pyridine carboxamide or sulfonamide derivative compounds. PCT Published Patent Applications, WO 03/075929, WO 03/076400 and WO 03/076401, disclose compounds having histone deacetylase inhibiting enzymatic activity.

BRIEF SUMMARY OF THE INVENTION

The present invention provides pyridazine derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of formula (I):

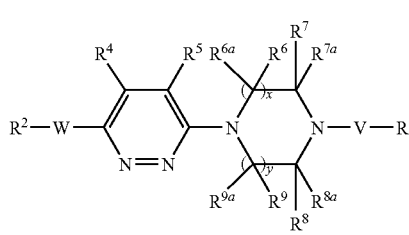

wherein:

x and y are each independently 1, 2 or 3;

W is $-C(O)N(R^1)-$; $-C(O)N[C(O)R^{1a}]-$, $-N(R^1)C(O)N(R^1)-$ or $-N(R^1)C(O)-$;

V is $-C(O)-$, $-C(S)-$, or $-C(R^{10})H$;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;

$R^{1a}$ is selected from the group consisting of hydrogen, $C_1$-$C_6$alkyl and cycloalkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or $-N(R^{12})_2$;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is $-C(O)-$, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (Ia):

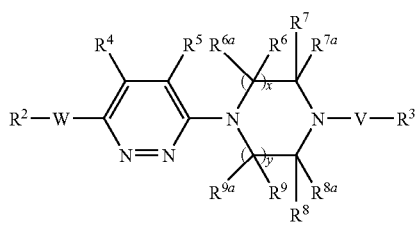

wherein:

x and y are each independently 1, 2 or 3;

W is a direct bond, $-C(O)N(R^1)-$; $-C(O)N[C(O)R^{1a}]-$, $-N(R^1)C(O)N(R^1)-$ $-N(R^1)C(O)-$, $-OC(O)N(R^1)-$, $-N(R^1)S(O)_p-$ (where p is 1 or 2), $-S(O)_pN(R^1)-$ (where p is 1 or 2), $-C(O)-$, $-OS(O)_2N(R^1)-$, $-OC(O)-$, $-C(O)O-$, $-N(R^1)C(O)O-$, $-N(R^1)C(=NR^{1a})N(R^1)-$, $-N(R^1)C(=S)N(R^1)-$, $-N(R^1)C(=NR^{1a})-$, or $-C(=NR^{1a})N(R^1)-$;

V is $-C(O)-$, $-C(O)O-$, $-C(S)-$, $-C(O)N(R^1)-$, $-S(O)_t-$ (where t is 0, 1 or 2), $-S(O)_pN(R^1)-$ (where p is 1 or 2), $-C(R^{10})H-$, or $-C(=NR^{1a})-$;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;

$R^{1a}$ is selected from the group consisting of hydrogen, $-OR^1$, cyano, $C_1$-$C_6$alkyl and cycloalkylalkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —$N(R^{12})_2$;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^5$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (II):

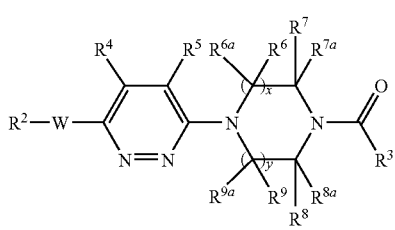

(II)

wherein:

x and y are each independently 1, 2 or 3;

W is selected from —C(O)N($R^1$)— and —N($R^1$)C(O)—;

each $R^2$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_5$-$C_{12}$ heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

including a stereoisomer, enantiomer or tautomer thereof, a pharmaceutically acceptable salt thereof, a pharmaceutical composition thereof or a prodrug thereof.

In another aspect, the invention provides compounds of formula (III):

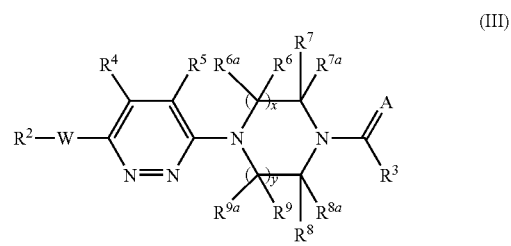

(III)

wherein:

x and y are each independently 1, 2 or 3;

A is oxygen or sulfur;

W is selected from —C(O)N($R^1$)— and —N($R^1$)C(O)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{11}$)$_2$, —OC(O)$R^{11}$, —C(O)O$R^{11}$, —S(O)$_2$N($R^{11}$)$_2$, cycloalkyl, heterocyclyl, heteroaryl and heteroarylcycloalkyl, provided that $R^3$ is not phenyl substituted with optionally substituted thienyl;

$R^4$ and $R^5$ are each independently selected from hydrogen, fluoro, chloro, methyl, methoxy and trifluoromethyl;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; and each $R^{11}$ is independently selected from hydrogen, $C_1$-$C_6$alkyl, $C_3$-$C_6$cycloalkyl, aryl or aralkyl;

a stereoisomer, enantiomer or tautomer thereof, a pharmaceutically acceptable salt thereof, a pharmaceutical composition thereof or a prodrug thereof.

In another aspect, the invention provides compounds of formula (IV):

(IV)

wherein:

x and y are each independently 1, 2 or 3;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, aryl, $C_7$-$C_{12}$aralkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$ hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

a stereoisomer, enantiomer or tautomer thereof, a pharmaceutically acceptable salt thereof, a pharmaceutical composition thereof or a prodrug thereof.

In another aspect, the invention provides compounds of formula (Va):

(Va)

wherein:

x and y are each independently 1, 2 or 3;

W is —C(O)N($R^1$)—; —N($R^1$)C(O)N($R^1$)— or —N($R^1$)C(O)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^4$ and $R^5$ are each independently selected from hydrogen, fluoro, chloro, methyl, methoxy, trifluoromethyl, cyano, nitro or —N($R^{12}$)$_2$;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

provided, however, that $R^2$ can not be pyrazinyl, pyridinonyl, pyrrolidinonyl or imidazolyl;

a stereoisomer, enantiomer or tautomer thereof, a pharmaceutically acceptable salt thereof, a pharmaceutical composition thereof or a prodrug thereof.

In another aspect, the invention provides compounds of formula (Vb):

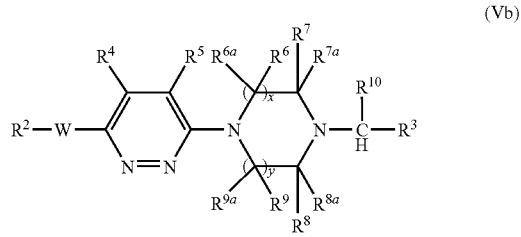

(Vb)

wherein:

x and y are each independently 1, 2 or 3;

W is —C(O)N($R^1$)—; —N($R^1$)C(O)N($R^1$)— or —N($R^1$)C(O)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxy;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_7$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy or $C_2$-$C_{12}$alkoxyalkyl $R^4$ and $R^5$ are each independently selected from hydrogen, fluoro, chloro, methyl, methoxy, trifluoromethyl, cyano, nitro or —N($R^{12}$)$_2$;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$, together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

as a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —OCH$_3$ radical.

"Cyano" refers to the —CN radical.

"Nitro" refers to the —NO$_2$ radical.

"Trifluoromethyl" refers to the —CF$_3$ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$ (where t is 1 to 2), $-S(O)_tR^{16}$ (where t is 0 to 2), and $-S(O)_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocylylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$ (where t is 1 to 2), $-S(O)_tR^{16}$ (where t is 0 to 2), and $-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to 12 carbon atoms. The $C_3$-$C_{12}$alkenyl radical may be optionally substituted as defined for an alkenyl group.

"$C_2$-$C_{12}$alkenyl" refers to an alkenyl radical as defined above containing two to 12 carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula $-OR_a$ where $R_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined-above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl-part of the $C_3$-$C_{12}$alkoxy radical may be optionally substituted as defined above for an alkyl group.

"Alkoxyalkyl" refers to a radical of the formula $-R_a-O-R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —S(O)$_2$R$_a$ where R$_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)R$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —R$_c$R$_b$ where R$_c$ is an alkenyl radical as defined above and R$_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy"-refers to a radical of the formula —OR$_b$ where R$_b$ is an aryl group as defined above. The aryl part of the aryloxy radical may be optionally substituted as defined above.

"Aryl-$C_1$-$C_6$alkyl" refers to a radical of the formula —R$_h$—R$_i$ where R$_h$ is an unbranched alkyl radical having one to six carbons and R$^1$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula —R$_a$R$_d$ where R$_a$ is an alkyl radical as defined above and R$_d$ is a cycloalkyl radical as defined above. The cycloalkyl part of the cycloalkyl radical may be optionally substituted as defined above for an cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t R^{16}$) (where t is 1 to 2), —$R^{15}$—S(O)$_t$O$R^{16}$ (where t is 1 to 2), —$R^{15}$—S(O)$_t R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula —$R_a R_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t R^{16}$) (where t is 1 to 2), —$R^{15}$—S(O)$_t$O$R^{16}$ (where t is 1 to 2), —$R^{15}$—S(O)$_t R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_a R_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_d R_f$ where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_bR_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to an hydroxyalkyl radical as defined above containing two to twelve carbon atoms. The alkyl part of the $C_2$-$C_{12}$hydroxyalkyl radical may be optionally substituted as defined above for an alkyl group.

"$C_3$-$C_{12}$hydroxyalkyl" refers to an hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to an hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula —$R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to an hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to an hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$trihaloalkyl" refers to a trihaloalkyl radical as defined above having one to six carbon atoms. The $C_1$-$C_6$trihaloalkyl may be optionally substituted as defined above for a trihaloalkyl group.

"Trihaloalkoxy" refers to a radical of the formula —$OR_9$ where $R_g$ is a trihaloalkyl group as defined above. The trihaloalkyl part of the trihaloalkoxy group may be optionally substituted as defined above for a trihaloalkyl group.

"$C_1$-$C_6$trihaloalkoxy" refers to a trihaloalkoxy radical as defined above having one to six carbon atoms. The $C_1$-$C_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

For example, a compound of formula (III), as set forth above in the Summary of the Invention, where x and y are both 1; A is oxygen; W is —N($R^1$)C(O)—; $R^1$, $R^4$, $R^5$, $R^6$, $R^{6a}$, $R^7$, $R^{7a}$, $R^8$, $R^{8a}$, $R^9$, and $R^{9a}$ are each hydrogen; $R^2$ is 2-cyclopropylethyl and $R^3$ is 2,5-dichlorophenyl, i.e., a compound of the following formula:

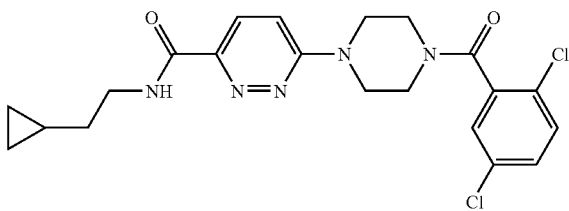

is named herein as 6-[4-(2,5-Dichlorobenzoyl)piperazin-1-yl]pyridazine-3-carboxylic acid (2-cyclopropylethyl)amide.

Certain radical groups of the compounds of the invention are depicted herein as linkages between two parts of the compounds of the invention. For example, in the following formula (I):

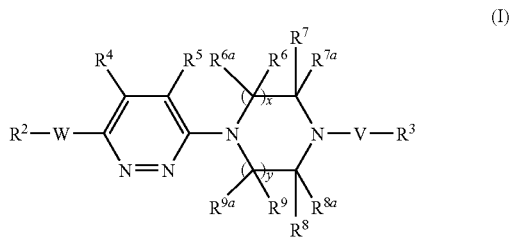

W is described, for example, as being —N($R^1$)C(O)—, —C(O)N($R^1$)—, or —N($R^1$)C(O)N($R^1$)—; and V is described as —C(O)—, —C(S)— or —C($R^{10}$)—. This description is meant to describe a W group attached to the $R^2$ group as follows: $R^2$—N($R^1$)C(O)—, $R^2$—C(O)N($R^1$)—, or $R^2$—N($R^1$)C(O)N($R^1$)—; and meant to describe a V group attached to the $R^3$ group as follows: —C(O)—$R^3$, —C($R^{10}$)—$R^3$, or —C(S)—$R^3$. In other words, the description of the W and V linkage groups are meant to be read from left to right in view of formula (I) as depicted above.

Embodiments of the Invention

In one embodiment of the invention as set forth above in the Summary of the Invention, a group of compounds of formula (II) is directed to compounds wherein x and y are each 1; W is selected from —C(O)N($R^1$)— and —N($R^1$)C(O)—; each $R^1$ is independently selected from hydrogen or $C_1$-$C_6$alkyl; $R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl; each $R^2$ is optionally substituted by one or more substituents selected from the group consisting of halo, $C_1$-$C_3$alkyl, —$OR^{11}$, —C(O)$OR^{11}$, $C_1$-$C_6$trihaloalkyl, cycloalkyl, heterocyclyl, aryl, heteroaryl and heteroarylcycloalkyl; $R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, $C_7$-$C_{12}$aralkyl, $C_3$-$C_{12}$heterocyclyl, $C_3$-$C_{12}$heterocyclylalkyl, $C_5$-$C_{12}$ heteroaryl and $C_3$-$C_{12}$heteroarylalkyl; each $R^3$ is optionally substituted by one or more substituents selected from the group consisting of $C_1$-$C_6$alkyl, $C_1$-$C_6$trihaloalkyl, $C_1$-$C_6$trihaloalkoxy, $C_1$-$C_6$alkoxy, $C_1$-$C_6$alkylsulfonyl, halo, cyano, nitro, hydroxy, —N($R^{12}$)$_2$, —C(O)$OR^{11}$, —S(O)$_2$N($R^{12}$)$_2$, cycloalkyl, heterocyclyl, aryl, aralkyl, heteroaryl and heteroarylcycloalkyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; each $R^{11}$ is independently selected from hydrogen, $C_1$-$C_6$alkyl, aryl or aralkyl; and each $R^{12}$ is independently selected from hydrogen or $C_1$-$C_6$alkyl.

Of this group of compounds of formula (II), a subgroup of compounds is directed to compounds wherein W is —N($R^1$)C(O)—; $R^1$ is hydrogen; $R^2$ is $C_4$-$C_{12}$cycloalkylalkyl; $R^3$ is $C_3$-$C_{12}$alkyl or $C_3$-$C_{12}$alkenyl, each optionally substituted with one or more halo groups; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

Another subgroup of this group of compounds of formula (II) is directed to compounds wherein W is —N($R^1$)C(O)—; $R^1$ is hydrogen; $R^2$ is $C_4$-$C_{12}$cycloalkylalkyl; $R^3$ is $C_3$-$C_{12}$cycloalkyl optionally substituted with one or more substituents selected from hydroxy, $C_1$-$C_6$trihaloalkyl or $C_1$-$C_6$alkyl; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

Another subgroup of this group of compounds of formula (II) is directed to compounds wherein W is —N($R^1$)C(O)—; $R^2$ is $C_4$-$C_{12}$cycloalkylalkyl and $R^3$ is $C_3$-$C_{12}$hydroxyalkyl optionally substituted with one or more halo groups; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

Another subgroup of this group of compounds of formula (II) is directed to compounds wherein W is —N($R^1$)C(O)—; $R^1$ is hydrogen; $R^2$ is $C_4$-$C_{12}$cycloalkylalkyl; $R^3$ is $C_3$-$C_{12}$alkoxy; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

Another subgroup of this group of compounds of formula (II) is directed to compounds wherein W is —N($R^1$)C(O)—; $R^1$ is hydrogen; $R^2$ is $C_4$-$C_{12}$cycloalkylalkyl; $R^3$ is $C_7$-$C_{12}$aralkyl optionally substituted with one or more substituents independently selected from halo or $C_1$-$C_6$trihaloalkyl; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

Another subgroup of this group of compounds of formula (II) is directed to compounds wherein W is —N($R^1$)C(O)—; $R^1$ is hydrogen; $R^2$ is $C_4$-$C_{12}$cycloalkylalkyl; $R^3$ is $C_3$-$C_{12}$heterocyclyl or $C_5$-$C_{12}$ heteroaryl, each optionally substituted with one or more substituents independently selected from halo, $C_1$-$C_6$alkyl, $C_1$-$C_6$trihaloalkyl or aralkyl; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

In another embodiment of the invention as set forth above in the Summary of the Invention, a group of compounds of formula (III) is directed to compounds wherein x and y are each 1; A is oxygen or sulfur; W is selected from —C(O)N($R^1$)— and —N($R^1$)C(O)—; each $R^1$ is independently selected from hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl; each $R^2$ is optionally substituted by one or more substituents selected from the group consisting of halo, cyano, oxo, thioxo, $C_1$-$C_3$alkyl, —$OR^{11}$, —$C(O)R^{11}$, —$OC(O)R^{11}$, —$C(O)OR^{11}$, —$C(O)N(R^{12})_2$, —$N(R^{12})_2$, $C_1$-$C_6$trihaloalkyl, cycloalkyl, heterocyclyl, aryl, heteroaryl and heteroarylcycloalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{11}$, —$C(O)OR^{11}$, —$S(O)_2N(R^{12})_2$, cycloalkyl, heterocyclyl and heteroarylcycloalkyl; $R^4$ and $R^5$ are each independently selected from hydrogen, fluoro, chloro, methyl, methoxy and trifluoromethyl; $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; or $R^6$ and $R^{6a}$ together or $R^9$ and $R^{9a}$ together are an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; each $R^{11}$ is independently selected from hydrogen, $C_1$-$C_6$alkyl, $C_3$-$C_6$cycloalkyl, aryl or aralkyl; and each $R^{12}$ is independently selected from hydrogen or $C_1$-$C_6$alkyl.

Of this group of compounds of formula (III), a subgroup of compounds is directed to compounds wherein x and y are each 1; A is oxygen or sulfur; W is —$N(R^1)C(O)$—; $R^1$ is hydrogen, methyl or ethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$alkyl.

Of this subgroup of compounds of formula (III), a set of compounds is directed to compounds wherein $R^2$ is $C_4$-$C_{12}$cycloalkylalkyl optionally substituted by one or more substituents selected from the group consisting of —$OR^{11}$, $C_1$-$C_3$alkyl or aryl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{11}$, —$C(O)OR^{11}$, —$S(O)_2N(R^{12})_2$ and cycloalkyl; each $R^{11}$ is independently selected from hydrogen, $C_1$-$C_6$alkyl, $C_3$-$C_6$cycloalkyl, aryl or aralkyl; and each $R^{12}$ is independently selected from hydrogen or $C_1$-$C_6$alkyl.

Another set of this subgroup of compounds of formula (III) is directed to compounds wherein A is oxygen; $R^2$ is $C_1$-$C_{12}$alkyl or $C_2$-$C_{12}$alkenyl, each optionally substituted by one or more substituents selected from the group consisting of halo, aryloxy, —$C(O)R^{11}$, —$OC(O)R^{11}$ or —$C(O)OR^{11}$; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{11}$, —$C(O)OR^{11}$, —$S(O)_2N(R^{12})_2$ and cycloalkyl; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein A is oxygen; $R^2$ is $C_2$-$C_{12}$hydroxyalkyl, $C_2$-$C_{12}$hydroxyalkenyl, each optionally substituted by one or more halo groups; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{11}$, —$C(O)OR^{11}$, —$S(O)_2N(R^{12})_2$ and cycloalkyl; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein A is oxygen; $R^2$ is $C_7$-$C_{12}$aralkyl, where the aryl part of the $C_7$-$C_{12}$aralkyl group is optionally substituted by one or more substituents independently selected from halo, $C_1$-$C_3$alkyl, —$OR^{11}$, —$C(O)OR^{11}$, $C_1$-$C_6$trihaloalkyl, cycloalkyl and aryl, and the alkyl part of the $C_7$-$C_{12}$aralkyl group is optionally substituted by one or more substituents independently selected from hydroxy, halo, —$OR^{11}$ and —$OC(O)R^{11}$; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{11}$, —$C(O)OR^{11}$, —$S(O)_2N(R^{12})_2$ and cycloalkyl; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein A is oxygen; $R^2$ is $C_1$-$C_6$alkoxy or $C_3$-$C_{12}$alkoxyalkyl, each optionally substituted with one or more substituents independently selected from halo or $C_3$-$C_6$cycloalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^2)_2$, —$OC(O)R^{11}$, —$C(O)OR^{11}$, —$S(O)_2N(R^2)_2$ and cycloalkyl; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein A is oxygen; $R^2$ is aryl optionally substituted with one or more substituents independently selected from halo, cyano, $C_1$-$C_3$alkyl, —$OR^{11}$, —$C(O)R^{11}$, —$OC(O)R^{11}$, —$C(O)OR^{11}$, —$C(O)N(R^{12})_2$, $C_1$-$C_6$trihaloalkyl, cycloalkyl, heterocyclyl, aryl, heteroaryl and heteroarylcycloalkyl; $R^3$ is phenyl optionally substituted by $C_1$-$C_6$trihaloalkyl or $C_1$-$C_6$trihaloalkoxy; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein A is oxygen; $R^2$ is $C_1$-$C_{12}$heteroaryl optionally substituted by one or more substituents selected from the group consisting of halo, cyano, oxo, thioxo, $C_1$-$C_3$alkyl, —$OR^{11}$, —$C(O)R^{11}$, —$OC(O)R^{11}$, —$C(O)OR^{11}$, —$C(O)N(R^{12})_2$ and $C_1$-$C_6$trihaloalkyl; $R^3$ is phenyl optionally substituted by $C_1$-$C_6$trihaloalkyl or $C_1$-$C_6$trihaloalkoxy; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Of this set of compounds of formula (III), a subset of compounds is directed to compounds wherein $C_1$-$C_{12}$heteroaryl is selected from the group consisting of pyridinyl, purinyl, pyrazinyl, indolyl, indazolyl, benzoimidazolyl, imidazolyl, tetrazolyl, triazolyl, isoxazolyl, pyrazolyl, pyrimidinyl, thiadiazolyl, thiazolyl and pyridazinyl.

Another set of this subgroup of compounds of formula (III) is directed to compounds wherein A is oxygen; $R^2$ is $C_3$-$C_{12}$ heterocyclyl, $C_3$-$C_{12}$heterocyclylalkyl or $C_3$-$C_{12}$heteroarylalkyl, each optionally substituted by one or more substituents selected from the group consisting of halo, cyano, oxo, thioxo, $C_1$-$C_3$alkyl, —$OR^{11}$, —$C(O)R^{11}$, —$OC(O)R^{11}$, —$C(O)OR^{11}$, —$C(O)N(R^{12})_2$ and $C_1$-$C_6$trihaloalkyl; $R^3$ is phenyl optionally substituted by halo, $C_1$-$C_6$trihaloalkyl or $C_1$-$C_6$trihaloalkoxy; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Of the group of compounds of formula (III) as set forth above, another subgroup of compounds of formula (III) is directed to compounds wherein x and y are each 1; A is oxygen; W is —$C(O)N(R^1)$—; $R^1$ is hydrogen, methyl or ethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each independently selected from hydrogen or $C_1$-$C_3$alkyl.

Of this subgroup of compounds, a set of compounds of formula (III) is directed to compounds wherein $R^2$ is $C_3$-$C_{12}$cycloalkyl or $C_4$-$C_{12}$cycloalkylalkyl, each optionally substituted by one or more substituents selected from the group consisting of —$OR^{11}$, $C_1$-$C_3$alkyl, $C_1$-$C_6$trihaloalkyl or aryl; $R^3$ is phenyl optionally substituted by one or more substituents selected from the group consisting of halo, $C_1$-$C_6$trihaloalkyl and $C_1$-$C_6$trihaloalkoxy; and each $R^{11}$ is independently selected from hydrogen, $C_1$-$C_6$alkyl, $C_3$-$C_6$cycloalkyl, aryl or aralkyl.

Another set of this subgroup of compounds of formula (III) is directed to compounds wherein $R^2$ is $C_1$-$C_{12}$alkyl, $C_2$-$C_{12}$alkenyl, $C_1$-$C_6$alkoxy or $C_3$-$C_{12}$alkoxyalkyl, each of which is optionally substituted by one or more substituents selected from the group consisting of halo, cyano, oxo, thioxo, $C_1$-$C_3$alkyl, —$OR^{11}$, —$C(O)R^{11}$, —$OC(O)R^{11}$, —$C(O)OR^{11}$, —$C(O)N(R^{12})_2$, —$N(R^{12})_2$, $C_1$-$C_6$trihaloalkyl, cycloalkyl and aryl; $R^3$ is phenyl optionally substituted by halo, $C_1$-$C_6$trihaloalkyl or $C_1$-$C_6$trihaloalkoxy; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

Another set of this subgroup of compounds of formula (III) is directed to compounds wherein $R^2$ is $C_7$-$C_{12}$aralkyl optionally substituted by one or more substituents selected from the group consisting of halo, cyano, oxo, thioxo, $C_1$-$C_3$alkyl, —$OR^{11}$, —$C(O)R^{11}$, —$OC(O)R^{11}$, —$C(O)OR^{11}$, —$C(O)N(R^{12})_2$, —$N(R^{12})_2$, $C_1$-$C_6$trihaloalkyl, cycloalkyl and aryl; $R^3$ is phenyl optionally substituted by halo, $C_1$-$C_6$trihaloalkyl or $C_1$-$C_6$trihaloalkoxy; each $R^{11}$ is independently selected from hydrogen, $C_1$-$C_6$alkyl, $C_3$-$C_6$cycloalkyl, aralkyl or aryl (optionally substituted with one or more halo groups); and each $R^{12}$ is independently selected from hydrogen or $C_1$-$C_6$alkyl.

In another embodiment of the invention as set for above in the Summary of the Invention, another group of compounds of formula (III) is directed to compounds wherein x and y are each 1; A is oxygen; W is —$N(R^1)C(O)$—; $R^1$ is hydrogen, methyl or ethyl; $R^2$ is cyclopropylethyl or cyclopropylmethyl; $R^3$ is phenyl optionally substituted by one or more substituents selected from the group consisting of fluoro, chloro and trifluoromethyl; $R^4$ and $R^5$ are each hydrogen; and $R^6$, $R^{6a}$, $R^7$, $R^{7a}$, $R^8$, $R^{8a}$, $R^9$, and $R^{9a}$ are each hydrogen.

In another embodiment of the invention as set for above in the Summary of the Invention, another group of compounds of formula (III) is directed to compounds wherein x and y are each 1; A is oxygen; W is —$N(R^1)C(O)$—; $R^1$ is hydrogen, methyl or ethyl; $R^2$ is $C_1$-$C_6$alkyl optionally substituted by —$C(O)OR^{11}$; $R^3$ is phenyl optionally substituted by one or more substituents selected from the group consisting of fluoro, chloro and trifluoromethyl; $R^4$ and $R^5$ are each hydrogen; $R^6$, $R^{6a}$, $R^7$, $R^{7a}$, $R^8$, $R^{8a}$, $R^9$, and $R^{9a}$ are each hydrogen; and $R^1$ is hydrogen, methyl, ethyl or 1,1-dimethylethyl.

In another embodiment of the invention as set for above in the Summary of the Invention, another group of compounds of formula (III) is directed to compounds wherein x and y are each 1; A is oxygen; W is —$N(R^1)C(O)$—; $R^1$ is hydrogen, methyl or ethyl; $R^2$ is 2-phenylethyl or 3-phenylpropyl where the phenyl group is optionally substituted by one or more substituents independently selected from chloro, fluoro or —$OR^{11}$; $R^3$ is phenyl optionally substituted by one or more substituents selected from the group consisting of fluoro, chloro and trifluoromethyl; $R^4$ and $R^5$ are each hydrogen; $R^6$, $R^{6a}$, $R^7$, $R^{7a}$, $R^8$, $R^5$, $R^9$, and $R^{9a}$ are each hydrogen; and $R^1$ is hydrogen, methyl, ethyl or 1,1-dimethylethyl.

In another embodiment of the invention as set for above in the Summary of the Invention, another group of compounds of formula (III) is directed to compounds wherein x and y are each 1; A is oxygen; W is —$C(O)N(R^1)$—; $R^1$ is hydrogen, methyl or ethyl; $R^2$ is cyclopropylethyl, cyclopropylmethyl or cyclopentylethyl; $R^3$ is phenyl optionally substituted by one or more substituents selected from the group consisting of fluoro, chloro and trifluoromethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each hydrogen.

In another embodiment of the invention as set for above in the Summary of the Invention, another group of compounds of formula (III) is directed to compounds wherein x and y are each 1; A is oxygen; W is —$C(O)N(R^1)$—; $R^1$ is hydrogen, methyl or ethyl; $R^2$ is $C_1$-$C_6$alkyl; $R^3$ is phenyl optionally substituted by one or more substituents selected from the group consisting of fluoro, chloro and trifluoromethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each hydrogen.

In another embodiment of the invention as set for above in the Summary of the Invention, another group of compounds of formula (III) is directed to compounds wherein x and y are each 1; A is oxygen; W is —$C(O)N(R^1)$—; $R^1$ is hydrogen, methyl or ethyl; $R^2$ is 3-phenylpropyl; $R^3$ is phenyl optionally substituted by one or more substituents selected from the group consisting of fluoro, chloro and trifluoromethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each hydrogen.

In another embodiment of the invention as set forth above in the Summary of the Invention, a group of compounds of formula (IV) is directed to compounds wherein x and y are each 1; each $R^1$ is hydrogen or $C_1$-$C_6$alkyl; $R^2$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxyalkyl, $C_3$-$C_{12}$cycloalkyl, $C_4$-$C_{12}$cycloalkylalkyl, $C_3$-$C_{12}$heterocyclyl, $C_3$-$C_{12}$heterocyclylalkyl, aryl, $C_7$-$C_{12}$aralkyl, $C_1$-$C_{12}$heteroaryl, and $C_3$-$C_{12}$heteroarylalkyl; each $R^2$ is optionally substituted by one or more substituents selected from the group consisting of halo, oxo, thioxo, $C_1$-$C_3$alkyl, —$OR^{11}$, —$C(O)OR^{11}$, $C_1$-$C_6$trihaloalkyl, cycloalkyl, heterocyclyl, aryl, heteroaryl and heteroarylcycloalkyl; $R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; where each of the above $R^3$ groups are optionally substituted by one or more substituents selected from the group consisting of $C_1$-$C_6$alkyl, $C_1$-$C_6$trihaloalkyl, $C_1$-$C_6$trihaloalkoxy, $C_1$-$C_6$alkoxy, $C_1$-$C_6$alkylsulfonyl, halo, cyano, nitro, hydroxy, —N($R^{12}$)$_2$, —C(O)O$R^{11}$, —S(O)$_2$N($R^{12}$)$_2$, cycloalkyl, heterocyclyl, aryl, heteroaryl and heteroarylcycloalkyl; $R^4$ and $R^5$ are each independently selected from hydrogen, fluoro, chloro, methyl, methoxy and trifluoromethyl; $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; or $R^6$ and $R^{6a}$ together or $R^7$ and $R^{7a}$ together are an oxo group while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; each $R^{11}$ is independently selected from hydrogen, $C_1$-$C_6$alkyl, $C_3$-$C_6$alkyl, aryl or aralkyl; and each $R^{12}$ is independently selected from hydrogen or $C_1$-$C_6$alkyl.

Of this group of compounds of formula (IV), a subgroup of compounds is directed to compounds wherein $R^2$ is $C_3$-$C_{12}$cycloalkyl or $C_4$-$C_{12}$cycloalkylalkyl, each optionally substituted by one or more substituents selected from the group consisting of —O$R^{11}$, $C_1$-$C_3$alkyl or aryl; $R^3$ is phenyl optionally substituted by one or more substituents selected from the group consisting of halo, $C_1$-$C_6$trihaloalkyl and $C_1$-$C_6$trihaloalkoxy; and each $R^{11}$ is independently selected from hydrogen, $C_1$-$C_6$alkyl, $C_3$-$C_6$cycloalkyl, aryl or aralkyl.

Another subgroup of this group of compounds of formula (IV) is directed to compounds wherein $R^2$ is $C_7$-$C_{12}$aralkyl optionally substituted by one or more substituents selected from the group consisting of halo, —O$R^{11}$ or $C_1$-$C_3$alkyl; $R^3$ is phenyl optionally substituted by one or more substituents selected from the group consisting of halo, $C_1$-$C_6$trihaloalkyl and $C_1$-$C_6$trihaloalkoxy; and each $R^{11}$ is independently selected from hydrogen, $C_1$-$C_6$alkyl, $C_3$-$C_6$cycloalkyl, aryl or aralkyl.

Another subgroup of this group of compounds of formula (IV) is directed to compounds wherein $R^2$ is aryl optionally substituted by one or more substituents selected from the group consisting of halo, —O$R^{11}$ or $C_1$-$C_3$alkyl; $R^3$ is phenyl optionally substituted by one or more substituents selected from the group consisting of halo, $C_1$-$C_6$trihaloalkyl and $C_1$-$C_6$trihaloalkoxy; and each $R^{11}$ is independently selected from hydrogen, $C_1$-$C_6$alkyl, $C_3$-$C_6$cycloalkyl, aryl or aralkyl.

Another subgroup of this group of compounds of formula (IV) is directed to compounds wherein $R^2$ is $C_3$-$C_{12}$alkyl, $C_3$-$C_{12}$hydroxyalkyl or $C_3$-$C_{12}$alkoxyalkyl, each optionally substituted by one or more substituents selected from the group consisting of halo, —O$R^{11}$ or —C(O)O$R^{11}$; $R^3$ is phenyl optionally substituted by one or more substituents selected from the group consisting of halo, $C_1$-$C_6$trihaloalkyl and $C_1$-$C_6$trihaloalkoxy; and each $R^{11}$ is independently selected from hydrogen, $C_1$-$C_6$alkyl, $C_3$-$C_6$cycloalkyl, aryl or aralkyl.

In another embodiment of the invention as set for above in the Summary of the Invention, another group of compounds of formula (IV) is directed to compounds wherein x and y are each 1; each $R^1$ is hydrogen, methyl or ethyl; $R^2$ is benzyl; $R^3$ is phenyl optionally substituted by one or more substituents selected from the group consisting of fluoro, chloro and trifluoromethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each hydrogen.

In another embodiment of the invention as set for above in the Summary of the Invention, another group of compounds of formula (IV) is directed to compounds wherein x and y are each 1; each $R^1$ is hydrogen, methyl or ethyl; $R^2$ is pentyl; $R^3$ is phenyl optionally substituted by one or more substituents selected from the group consisting of fluoro, chloro and trifluoromethyl; $R^4$ and $R^5$ are each independently selected from hydrogen, fluoro, chloro, methyl, methoxy and trifluoromethyl; and $R^6$, $R^{6a}$, $R^7$, $R^{7a}$, $R^8$, $R^{8a}$, $R^9$, and $R^{9a}$ are each hydrogen.

In another embodiment of the invention as set forth above in the Summary of the Invention, a group of compounds of formula (Va) is directed to compounds wherein x and y are each independently 1; W is —N($R^1$)C(O)—; each $R^1$ is hydrogen or $C_1$-$C_6$alkyl; $R^2$ is selected from the group consisting of $C_7$-$C_{12}$alkyl, $C_2$-$C_{12}$alkenyl, $C_7$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, $C_{13}$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; each $R^2$ is optionally substituted by one or more substituents selected from the group consisting of halo, cyano, oxo, thioxo, $C_1$-$C_3$alkyl, —O$R^{11}$, —C(O)$R^{11}$, —OC(O)$R^{11}$, —C(O)O$R^{11}$, —C(O)N($R^{12}$)$_2$, —N($R^{12}$)$_2$, $C_1$-$C_6$trihaloalkyl, cycloalkyl, heterocyclyl, aryl, heteroaryl and heteroarylcycloalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; each $R^3$ is optionally substituted by one or more substitutents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{11}$, —C(O)O$R^{11}$, —S(O)$_2$N($R^{12}$)$_2$, cycloalkyl, heterocyclyl and heteroarylcycloalkyl; $R^4$ and $R^5$ are each independently selected from hydrogen, fluoro, chloro, methyl, methoxy, trifluoromethyl, cyano, nitro or —N($R^{12}$)$_2$; $R^6$, $R^{6a}$, $R^7$, $R^{7a}$, $R^8$, $R^{8a}$, $R^9$, and $R^{9a}$ are each independently selected from hydrogen or $C_1$-$C_3$alkyl; $R^{10}$ is hydrogen or $C_1$-$C_3$alkyl; each $R^{11}$ is independently selected from hydrogen, $C_1$-$C_6$alkyl, $C_3$-$C_6$cycloalkyl, aryl or aralkyl; and each $R^{12}$ is independently selected from hydrogen or $C_1$-$C_6$alkyl.

Of this group of compounds of formula (Va), a subgroup of compounds is directed to compounds wherein $R^2$ is $C_3$-$C_{12}$cycloalkyl or $C_4$-$C_{12}$cycloalkylalkyl, each optionally substituted by one or more substituents selected from the group consisting of halo, $C_1$-$C_6$trihaloalkyl, —O$R^{11}$, $C_1$-$C_3$alkyl or aryl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{11}$, —C(O)O$R^{11}$, —S(O)$_2$N($R^{12}$)$_2$ and cycloalkyl; each $R^{11}$ is independently selected from hydrogen, $C_1$-$C_6$alkyl, $C_3$-$C_6$cycloalkyl, aryl or aralkyl; and each $R^{12}$ is independently selected from hydrogen or $C_1$-$C_6$alkyl.

In another embodiment of the invention as set forth above in the Summary of the Invention, a group of compounds of formula (Ia) is directed to compounds wherein W is —N($R^1$)C(O)— and V is —C(=NH)—.

Another group of compounds of formula (Ia) is directed to compounds wherein W is —N($R^1$)C(=N$R^{1a}$)—.

Another group of compounds of formula (Ia) is directed to compounds wherein W is —N($R^1$)C(=N$R^{1a}$)N($R^1$)— or —N($R^1$)C(=S)N($R^1$)—.

Specific embodiments of the above-described groups, subgroups and sets of compounds of formula (II), (III), (IV), (Va) and (Ia) are disclosed herein in the Reaction Schemes and Examples set forth below.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 33. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)).

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition includes but is not limited to a disease or condition which is, or is related to, cardiovascular disease, dyslipidemias (including, but not limited to, disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including, but not limited, to stroke, ischemic stroke and transient ischemic attack (TIA)), peripheral vascular disease, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including, but not limited to, dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including, but not limited to, obesity, overweight, cachexia and anorexia), weight loss, body mass index and leptin related diseases. In a preferred embodiment, compounds of the invention will be used to treat diabetes mellitus and obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes, but not limited to, a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including, but not limited to, eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes, but not limited to, a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including, but not limited to, all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, liheus virus, Rocio encephalitis virus, Langat virus, Pestivirus, Bovine viral diarrhea, Hog cholera virus, $R^{10}$ Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable. ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 µM, preferably below 1 µM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Brownlie et al, supra. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n–9/18:0 (oleic acid over stearic acid); 16:1n–7/16:0 (palmitoleic acid over palmitic acid); and/or 16:1n–7+18:1n–7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyidimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R¹ (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

Unless specifically indicated otherwise in the following descriptions, x, y, W, V, $R^1$, $R^{1a}$, $R^2$, $R^3$, $R^4$, $R^5$, $R^6$, $R^{6a}$, $R^7$, $R^{7a}$, $R^8$, $R^{8a}$, $R^9$ and $R^{9a}$ are as defined above in the Summary of the Invention for compounds of formula (I), compounds of formula (Ia) and compounds of formula (IV). It is understood that compounds of formula (II), formula (III), formula (Va) and formula (Vb) can be prepared in methods similiar to those described below. In addition, compounds of the invention may also be prepared according to the methods similar to those disclosed in priority document, PCT/US2004/024658, which is incorporated in full by reference herein.

In general, the compounds of formula (I) and formula (Ia) of this invention where W is —N(R¹)C(O)— can be synthesized following the general procedure as described in Reaction Scheme 1.

REACTION SCHEME 1

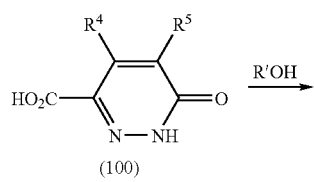

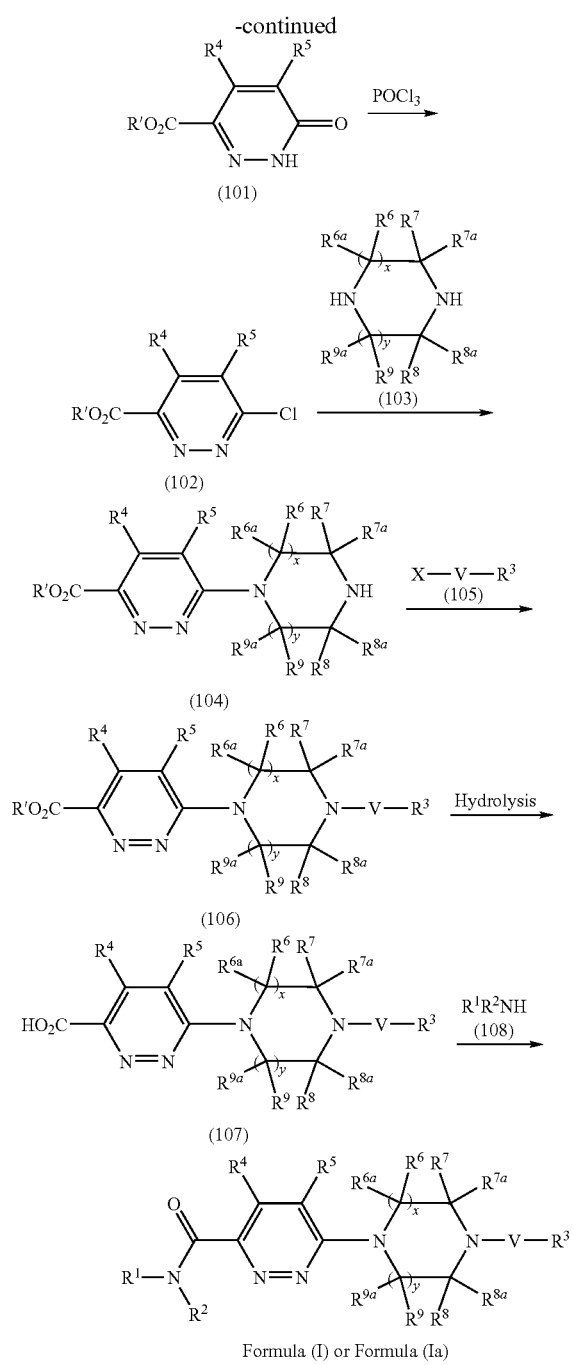

The starting materials for the above reaction scheme are commercially available or can be prepared according to methods known to one skilled in the art or by methods disclosed herein. In general, the compounds of the invention are prepared in the above reaction scheme as follows:

Compound 101. A carboxylic acid of formula (100) can easily be converted to an ester of formula (101) following a standard procedure in the literature known to one skilled in the art.

Compound 102. A mixture of a compound of formula (101) obtained above and phosphorous oxychloride is carefully heated to reflux for 2-8 hours. The reaction mixture is then cooled and excess phosphorous oxychloride is removed. The residue is then poured into ice water. The precipitate obtained is collected by filtration, washed with saturated NaHCO₃ and water, and then dried to yield the compound of formula (102).

Compound 104. A mixture of the compound of formula (102) (1 equivalent) and the compound of formula (103) (3 equivalent) in a solvent such as, but not limited to, N,N-dimethylformamide or acetonitrile is refluxed for 1-4 hours. The solvent is then removed in vacuo. The residue is dissolved in a solvent such as, but not limited to, dichloromethane or ethyl acetate. The resulting solution is washed with water, brine, and then dried over MgSO₄. The organic phase was concentrated in vacuo to afford the compound of formula (104).

Compound 106. To a stirred solution of the compound of formula (104) (1 equivalent) in a solvent such as, but not limited to, dichloromethane, toluene or THF is added the solution of a chloride or bromide of formula (105) (1 equivalent) in the presence of a base such as, but not limited to, triethylamine or Hunigs base at 0° C. The resulting mixture is stirred at ambient temperature for 6-18 hours and then quenched with water. The organic phase is washed with water, brine, dried over MgSO₄ and then concentrated in vacuo to afford the product of formula (106) which is further purified by chromatography or crystallization.

Compound 107. A solution of a compound of formula (106) obtained above is dissolved in an adequate solvent and the ester is converted to a carboxylic acid under a standard condition known to one skilled in the art to obtain the carboxylic acid of formula (107).

Compound of formula (I) or formula (Ia). To a solution of a compound of formula (107) (1 equivalent) in a solvent such as, but not limited to dichloromethane, toluene or THF is added a base such as, but not limited to, triethylamine or Hunigs base (2.5 equivalent), followed by the addition of a coupling agent such as N-(3-dimethylaminopropyl)-N'-ethylcarbodiimide (1.1 equivalent). The resulting mixture is stirred for 15 minutes to an hour and an amine of formula (108) (1.1 equivalent) is added. The mixture is stirred for 8-24 hours, then washed with water, dried over MgSO₄ and concentrated in vacuo. Purification by column chromatography or crystallization from a suitable solvent affords the compound of formula (I) or formula (Ia).

Alternatively, compounds of formula (I) or formula (Ia) of this invention where W is —N(R¹)C(O)— can be synthesized following the general procedure as described in Reaction Scheme 2.

REACTION SCHEME 2

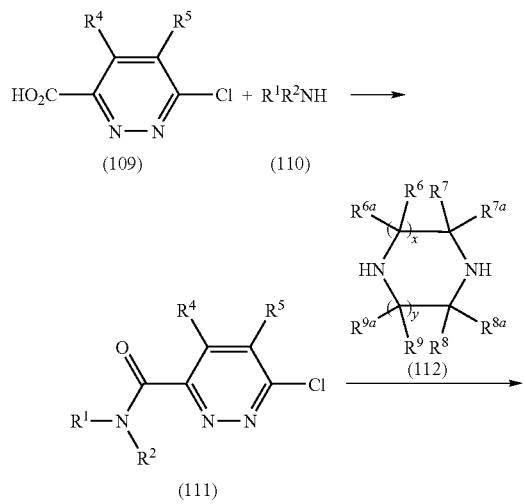

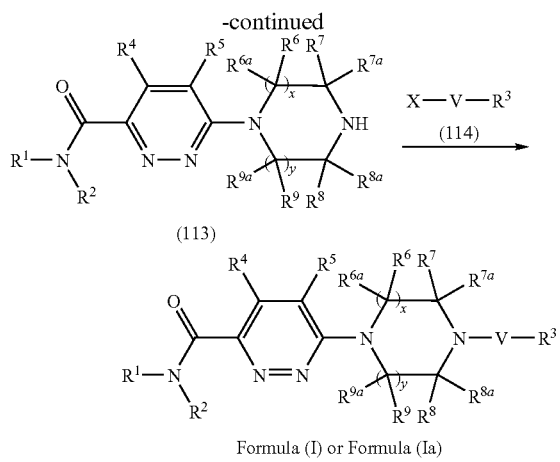

Formula (I) or Formula (Ia)

The starting materials for the above reaction scheme are commercially available or can be prepared according to methods known to one skilled in the art or by methods disclosed herein. In general, the compounds of the invention are prepared in the above reaction scheme as follows:

Compound 111. To a solution of substituted 6-chloropyridazinyl-3-carboxylic acid of formula (109) (1 equivalent) in a solvent such as, but not limited to, dichloromethane, toluene or THF is added a base such as, but not limited to, triethylamine or Hunigs base (2.5 equivalent), followed by the addition of a coupling agent such as N-(3-dimethylaminopropyl)-N'-ethylcarbodiimide (1.1 equivalent). The resulting mixture is stirred for 15 minutes to an hour and an amine of formula (110) (1.1 equivalent) is added. The mixture is stirred for 8-24 hours, then washed with water, dried over MgSO₄ and concentrated in vacuo. Purification by column chromatography or crystallization from a suitable solvent affords the compound of formula (111).

Compound 113. A mixture of the compound of formula (111) (1 equivalent) and the compound of formula (112) (3 equivalent) in a solvent such as, but not limited to, N,N-dimethylformamide or acetonitrile is refluxed for 1-4 hours. The solvent is then removed in vacuo. The residue is dissolved in a solvent such as dichloromethane or ethyl acetate but not limited to. The resulting solution is washed with water, brine, and then dried over MgSO₄. The organic phase was concentrated in vacuo to afford the compound of formula (113).

Compound of Formula (I) or Formula (Ia). To a stirred solution of the compound of formula (113) (1 equivalent) in a solvent such as, but not limited to, dichloromethane, toluene or THF is added the solution of a chloride or bromide of formula (114) (1 equivalent) in the presence of a base such as, but not limited to, triethylamine or Hunigs base at 0° C. The resulting mixture is stirred at ambient temperature for 6-18 hours and then quenched with water. The organic phase is washed with water, brine, dried over MgSO₄ and then concentrated in vacuo to afford the compound of formula (I) or formula (Ia) which is further purified by chromatography or crystallization.

Alternatively, compounds of formula (I) or formula (Ia) of this invention where W is —C(O)N(R¹)— and PG is a nitrogen protecting group can be synthesized following the general procedure as described in Reaction Scheme 3.

REACTION SCHEME 3

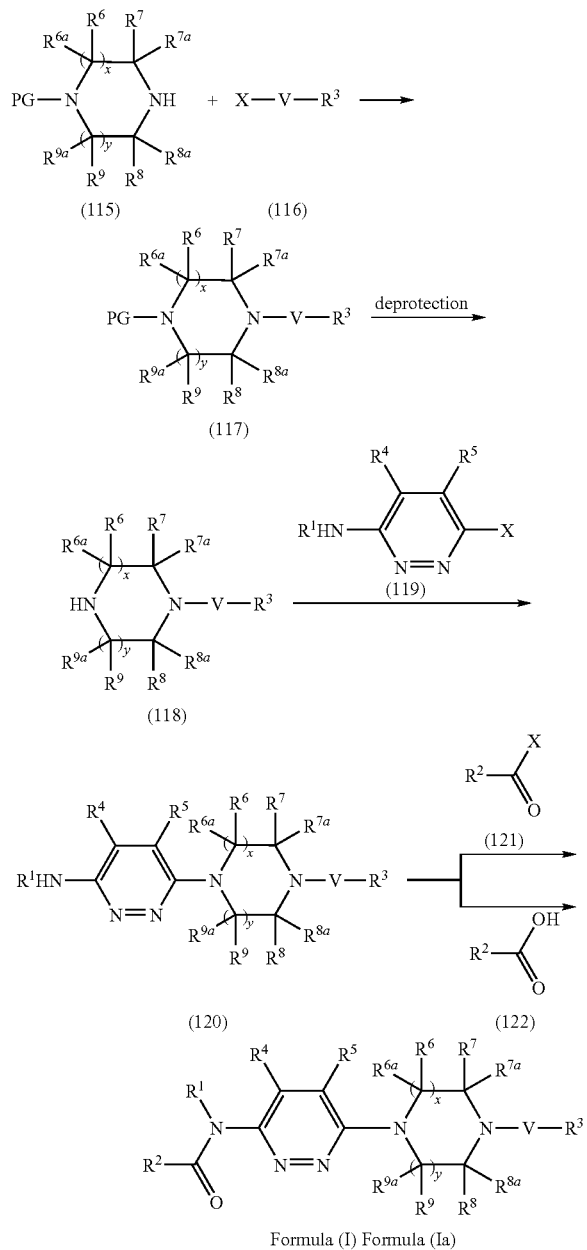

Formula (I) Formula (Ia)

The starting materials for the above reaction scheme are commercially available or can be prepared according to methods known to one skilled in the art or by methods disclosed herein. In general, the compounds of the invention are prepared in the above reaction scheme as follows:

Compound 117. To a stirred solution of the amine of formula (115) (1 equivalent) in a solvent such as, but not limited to, dichloromethane or toluene is added the solution of a chloride or bromide of formula (116) (1 equivalent) in a solvent such as, but not limited to, dichloromethane or toluene in the presence of a base such as, but not limited to, triethylamine or Hunigs base. The resulting mixture is stirred at ambient temperature for an adequate time period and then quenched with water. The organic phase is washed with water, brine, dried over $MgSO_4$ and then concentrated in vacuo to afford the product of formula (117).

Compound 118. A solution of compound of formula (117) obtained above is dissolved in an adequate solvent and the protecting group PG is removed under standard deprotection conditions such as hydrolysis or hydrogenation to obtain the amine of formula (118).

Compound 120. A mixture of a chloropyridazine of formula (119) (1 equivalent) and the amine of formula (118) obtained above (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (120).

Compound of Formula (I) or Formula (Ia).

Method A. To a stirred solution of compound of formula (120) (1 equivalent) in a solvent such as, but not limited to, dichloromethane, acetonitrile or toluene is added the solution of a compound of formula (121) (1 equivalent) in the presence of a base such as, but not limited to, triethylamine or Hunigs base (1 equivalent) at 0° C. The resulting mixture is stirred at ambient temperature for 8-24 hours and then quenched with water. The organic phase is washed with water, brine, dried and then concentrated in vacuo. Further purification by column chromatography or crystallization from a suitable solvent affords the compound of formula (I).

Method B. To a solution of a carboxylic acid of formula (122) (1 equivalent) in a solvent such as, but not limited to, dichloromethane, toluene or THF is added a base such as, but not limited to, triethylamine or Hunigs base (2.5 equivalent), followed by the addition of a coupling agent such as, but not limited to, (3-dimethylaminopropyl)ethyl carbodiimide (1.1 equivalent). The resulting mixture is stirred for 15 minutes to an hour and an amine of formula (120) (1.1 equivalent) is added. The mixture is stirred at ambient temperature for 8-24 hours, then washed with water, dried and concentrated in vacuo. Purification by column chromatography or crystallization from a suitable solvent affords the compound of formula (I).

Alternatively, compounds of formula (Ia) of this invention where W is —N($R^1$)C(O)— and V is —C(=NH)— can be synthesized following the general procedure as described in Reaction Scheme 4.

REACTION SCHEME 4

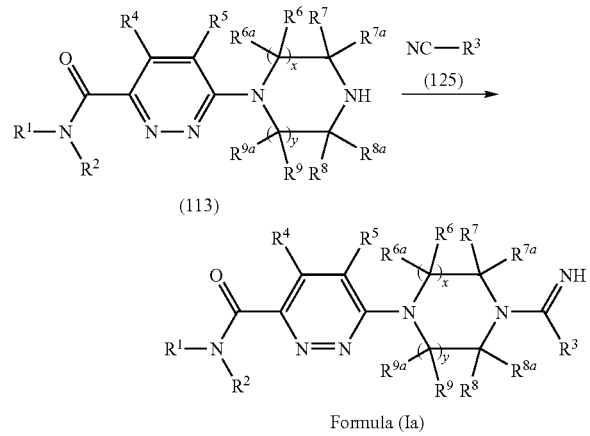

Formula (Ia)

The starting materials for the above reaction scheme are commercially available or can be prepared according to methods known to one skilled in the art or by methods disclosed herein. In general, the compounds of the invention are prepared in the above reaction scheme as follows:

Compound of formula (Ia): A Lewis acid such as, but not limited to, trimethylaluminum in a solvent such as, but not limited to, benzene or toluene (1 equivalent) is added to a solution of (113) (1 equivalent) in a solvent such as 1,4-dioxane at a reduced temperature. After the addition is complete, the reaction mixture is allowed to warm to ambient temperature, and the stirring is continued. Compound of formula (125) (1.1 equivalent) is then added and the reaction mixture is heated to reflux for 8-24 hours, then cooled to ambient temperature and poured into slurry of silica gel in chloroform. Filtration and evaporation of solvents afford the crude product which is purified by crystallization or column chromatography.

Alternatively, the compound of formula (Ia) of the invention where W is —N(H)C(=NH)— can be synthesized following the general procedure as described in Reaction Scheme 5.

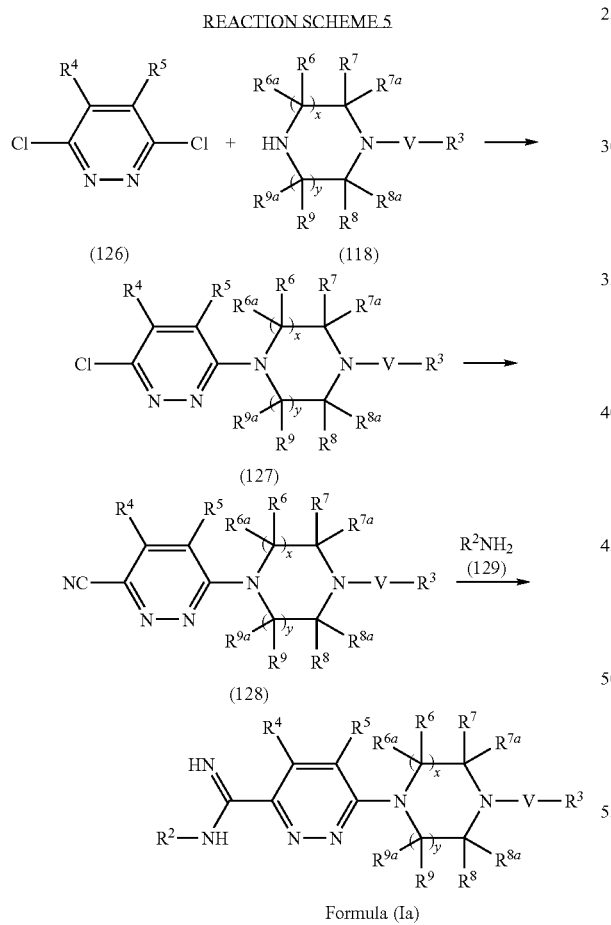

The starting materials for the above reaction scheme are commercially available or can be prepared according to methods known to one skilled in the art or by methods disclosed herein. In general, the compounds of the invention are prepared in the above reaction scheme as follows:

Compound 127: A degassed mixture of (118) (1 equivalent), (126) (1 equivalent), a base such as $K_2CO_3$ (2 equivalent), a ligand such as, but not limited to, 8-hydroquinoline and CuI in a solvent such as, but not limited to, DMSO is heated at 120° C. for 12-24 h under nitrogen. The reaction mixture is cooled to ambient temperature and filtered. The compound of formula (127) is obtained after purification.

Compound 128: A degassed mixture of (127) (1.2 equivalent), a cyanide reagent such as, but not limited to, $Zn(CN)_2$ (1 equivalent), a ligand such as, but not limited to, 1,1'-bis (diphenylphosphino)ferrocene (DPPF) and a palladium catalyst such as, but not limited to, $Pd_2$ $dba_3$ in a solvent mixture such as, but not limited to, DMF and water is heated to 120° C. for 12-24 h under nitrogen. The reaction mixture is cooled to ambient temperature and filtered. The compound of formula (128) is obtained after purification.

Compound of formula (Ia): A Lewis acid such as, but not limited to, trimethylaluminum in solvent such as benzene or toluene (1 equivalent) is added to a solution of (129) (1 equivalent) in a solvent such as, but not limited to, 1,4-dioxane at a reduced temperature. After the addition is complete, the reaction mixture is allowed to warm to ambient temperature, and the stirring is continued. Compound of formula (128) (1.1 equivalent) is then added and the reaction mixture is heated to reflux for 8 to 24 hours, then cooled to ambient temperature and poured into slurry of silica gel in chloroform. Filtration and evaporation of solvents afford the compound of formula (Ia) as the crude product which is purified by crystallization or column chromatography.

Alternatively, the compound of formula (Ia) of the invention where W is —N(R¹)C(=NH)N(H)— or —N(R¹)C(=S)N(H)— can be synthesized following the general procedure as described in Reaction Scheme 6.

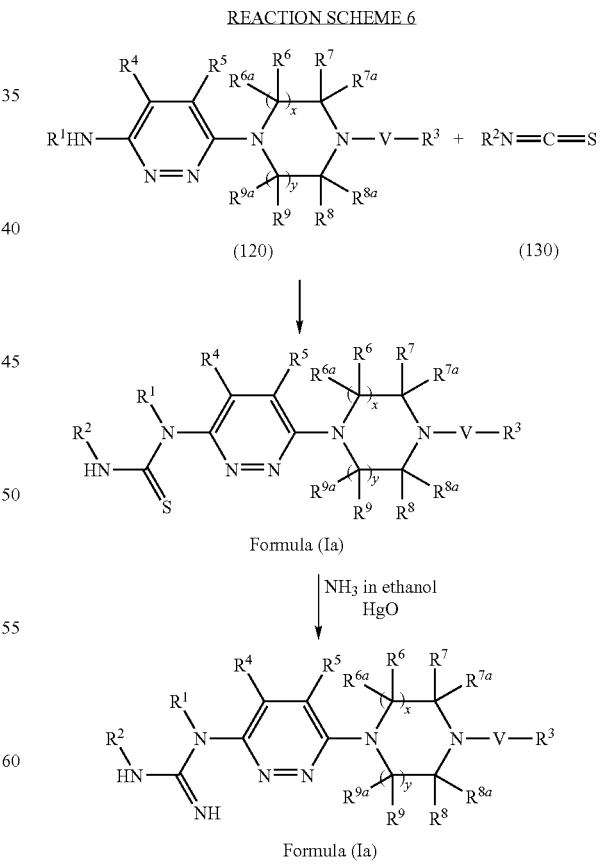

The starting materials for the above reaction scheme are commercially available or can be prepared according to methods known to one skilled in the art or by methods disclosed herein. In general, the compounds of the invention are prepared in the above reaction scheme as follows:

Compounds of Formula (Ia) where W is —N(R$^1$)C(=S)N(H)—: A mixture of the compound of formula (120) (1 equivalent), a base such as, but not limited to, triethylamine (1 equivalent), and the isothiocyanate (130) (2 equivalent) in a solvent such as, but not limited to, N,N-dimethylformamide or N-methyl-2-pyrrolidinone is stirred for 10-16 h. The solvent is then removed in vacuo. The residue is dissolved in a solvent such as, but not limited to, dichloromethane or ethyl acetate. The resulting solution is washed with water, brine, dried, and then purified by flash chromatography to afford the compound of formula (Ia).

Compounds of Formula (Ia) where W is —N(R$^1$)C(=NH)N(H)—: Mercury oxide and ammonium hydroxide is added to a stirred solution of the compound of formula (Ia) where W is —N(R$^1$)C(=S)N(H)— in ethanol, and the mixture is stirred at ambient temperature for 8-24 h. The resulting mixture is diluted with ethyl acetate, and filtered through a pad of celite. The filtrate is then dried, concentrated, and purified by flash chromatography to give compound of formula (Ia) where W is —N(R$^1$)C(=NH)N(H)—.

Alternatively, the compound of formula (I) of the invention where W is —N(R$^1$)C(=NR$^{1a}$)N(H)— can be synthesized following the general procedure as described in Reaction Scheme 7.

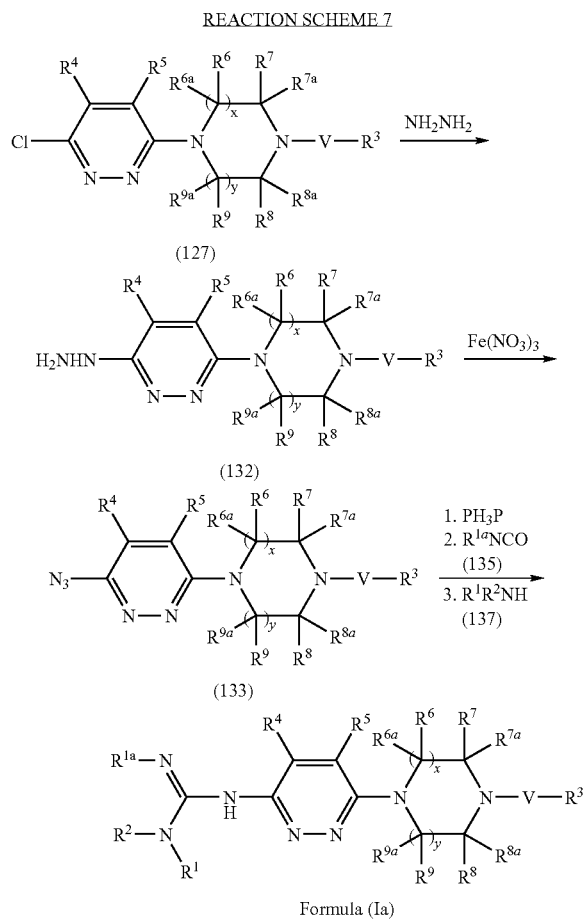

The starting materials for the above reaction scheme are commercially available or can be prepared according to methods known to one skilled in the art or by methods disclosed herein. In general, the compounds of the invention are prepared in the above reaction scheme as follows:

Compound 132. A mixture of the compound of formula (127) (1 equivalent) and hydrazine (5 equivalent) in a solvent such as, but not limited to, N,N-dimethylformamide or N-methyl-2-pyrrolidinone or dioxane is heated to 90° C. for 5-16 hours. The solvent is then removed in vacuo. The residue is dissolved in a solvent such as, but not limited to, dichloromethane or ethyl acetate. The resulting solution is washed with water, brine, dried, and then purified to afford the compound of formula 132.

Compound 133. A mixture of the compound of formula (132) and Fe(NO$_3$)$_3$ in a solvent such as, but not limited to, chloromethane is refluxed for 5 hours. The mixture is diluted with chloromethane, the resulting solution is washed with water, brine, dried, and then purified to afford the compound of formula (133).

Compound of formula (Ia). To a solution of the compound of formula (133) (1 equivalent) in a solvent such as, but not limited to, THF is added triphenylphosphine (1.2 equivalent) at ambient temperature. After 10 minutes, isocyanate compound (135) (1.2 equivalent) is added, and the solution is heated at 70° C. for 12-24 h. The amine (137) (2.0 equivalent) is added, and the mixture is further heated at 70° C. for 1-4 h. The resulting mixture is diluted with ethyl acetate, and the resulting solution is washed with water, brine, dried over sodium sulfate, and then purified by flash chromatography to afford the compound of formula (Ia) where W is —N(R$^1$)C(=NR$^{1a}$)N(H)—.

Alternatively, the compound of formula (Ia) of the invention where W is —N(R$^1$)C(=N—CN)N(R$^1$)— can be synthesized following the general procedure as described in Reaction Scheme 8.

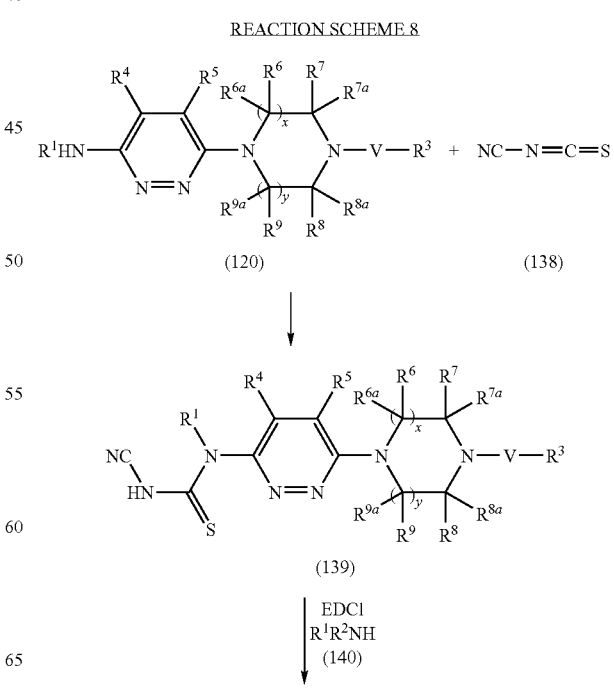

-continued

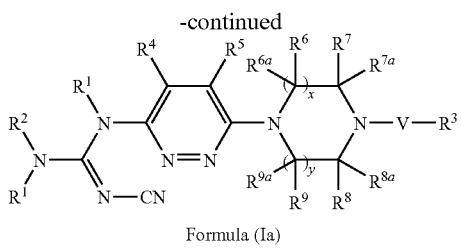

Formula (Ia)

The starting materials for the above reaction scheme are commercially available or can be prepared according to methods known to one skilled in the art or by methods disclosed herein. In general, the compounds of the invention are prepared in the above reaction scheme as follows:

Compound 139. A mixture of the compound of formula 120 (1 equivalent), cyanogens isothiocyanate (2 equivalent) in a solvent such as, but not limited to, N,N-dimethylformamide or N-methyl-2-pyrrolidinone or THF is heated to 50-90° C. for 5 to 16 h. The solvent is then removed in vacuo. The residue is dissolved in a solvent such as, but not limited to, dichloromethane or ethyl acetate. The resulting solution is washed with water, brine, dried, and then purified by flash chromatography to afford the compound of formula (139).

Compound of formula (Ia). To a stirred solution of the compound (139) (1 equivalent) and amino compound (140) (1.2 equivalent) in N,N-dimethylformamide or N-methyl-2-pyrrolidinone is treated with EDCl (1-(3-dimethylaminopropyl)-3-ethylcarbodiimide hydrochloride) (1.2 equivalent) or other coupling reagents, and the mixture was stirred at ambient temperature for 1-4 h. The resulting mixture is diluted with ethyl acetate, and the resulting solution is washed with water, brine, dried over sodium sulfate, and then purified by flash chromatography to afford the compound of formula (Ia) where W is —N($R^1$)C(=N—CN)N($R^1$)—.

Alternatively, compounds of formula (IV) of this invention can be synthesized following the general procedure as described in Reaction Scheme 9.

REACTION SCHEME 9

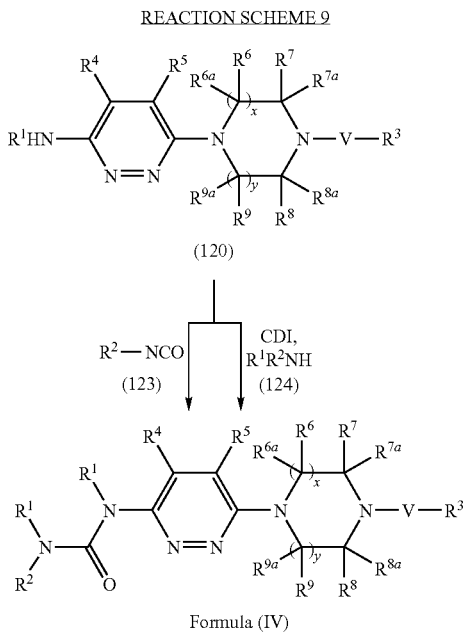

Formula (IV)

The starting materials for the above reaction scheme are commercially available or can be prepared according to methods known to one skilled in the art or by methods disclosed herein. In general, the compounds of the invention are prepared in the above reaction scheme as follows:

Compound of Formula (IV):

Method C. To a stirred solution of the compound of formula of (120) (1 equivalent) in an anhydrous solvent such as DMF but not limited to is added an isocyanate of formula (123) (3 equivalent), and the mixture is then heated to 60-80° C. for 4-24 hours. The mixture is concentrated in vacuo. Purification of the crude product by column chromatography or crystallization from a suitable solvent affords the compound of Formula (IV).

Method D. A compound of formula (120) (1 equivalent) is slowly added to an ice cold solution of 1,1'-carbonyldiimidazole (1.5 to 2.5 equivalent) in an anhydrous solvent such as dichloromethane. The temperature is then raised to ambient temperature and the reaction mixture is stirred for another 2-8 hours. An amine of formula (124) (1 equivalent) is then added to the reaction mixture which is stirred at ambient temperature overnight under nitrogen atmosphere. The reaction mixture is then washed with saturated sodium bicarbonate and brine solution, concentrated and purified by flash column chromatography to afford the compound of formula (IV).

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

Preparation 1

Synthesis Of 2-Cyclopropylethylamine

Concentrated sulfuric acid (20.66 mL) was added dropwise to a vigorously stirred suspension of lithium aluminum hydride (764.4 mmol) in 800 mL of anhydrous ethyl ether (40 mL) at 0° C. for at least 2 hour period. The reaction mixture was warmed to ambient temperature and stirred for 1 hour, and a solution of cyclopropylacetonitrile (246.5 mmol) in 100 mL of anhydrous ethyl ether was added dropwise. The resulting mixture was heated to reflux for 2 hours, then cooled to 0° C., cautiously quenched with crushed ice. A solution of 38 g of NaOH in 350 mL of water was added, and the organic layer was decanted from the resulting aluminum hydroxide precipitate. The precipitate was washed thoroughly with ethyl ether (3×600 mL). All ethereal extracts were combined, dried over anhydrous $Na_2SO_4$ and the solvent was distilled off to afford 172.5 mmol of 2-cyclopropylethylamine as a colorless liquid (bp~100-108° C.). Yield 70%.

Preparation 2

Synthesis of 6-Chloropyridazine-3-Carboxylic Acid

To a mechanically stirred solution of 3-chloro-6-methylpyridazine (155.6 mmol) in 140 mL of concentrated sulfuric acid, finely powdered potassium dichromate (55.40 g) was added slowly, the temperature being kept below 50° C. When the addition was complete, stirring was continued for another 4 hours at 50° C. The viscous, dark green liquid was then cooled and crushed ice was added cautiously. The reaction mixture was extracted with ethyl acetate (6×400 mL). The ethyl acetate extracts were combined, dried over anhydrous $Na_2SO_4$. The solvent was concentrated in vacuo to yield slightly red colored 6-chloropyridazine-3-carboxylic acid (106.6 mmol). This material was used for next reaction without further purification. Yield 69%. m.p. 145° C. (dec). $^1$H NMR (300 MHz, DMSO-d$_6$) δ 13.1, 8.20, 8.05.

Preparation 3

Synthesis Of 6-Chloropyridazine-3-Carboxylic Acid (2-Cyclopropylethyl)Amide

To a solution of 6-chloropyridazine-3-carboxylic acid (15.8 mmol) in dichloromethane (95 mL) was added diisopropylethylamine (46.7 mmol), 1-hydroxybenzotriazole monohydrate (23.7 mmol) and 1-(3-dimethylaminopropyl)-3-ethylcarbodiimide (23.7 mmol) under nitrogen atmosphere at ambient temperature. The resulting mixture was stirred for 15 minutes and 2-cyclopropylethylamine (20.2 mmol) was added. After stirring for 36 hours at ambient temperature, the reaction mixture was diluted with dichloromethane (100 mL), then washed with water and dried over anhydrous Na$_2$SO$_4$. The solvent was removed in vacuo. Purification via column chromatography (30% ethyl acetate in hexanes) afforded the title compound (8.70 mmol). Yield 55%.

Preparation 4

Synthesis Of 6-Chloropyridazine-3-Carboxylic Acid (3-Methylbutyl)Amide

The mixture of 6-oxo-1,6-dihydropyridazine-3-carboxylic acid monohydrate (3.16 g; 20.0 mmol), dimethylformamide (0.5 mL) and thionyl chloride (5-7 mL) in chloroform (70 mL) was kept at 50-60° C. overnight. The reaction mixture was evaporated in vacuo to dryness. The solid residue was dissolved in dichloromethane (70 mL) and added dropwise to the mixture of 3-methylbutylamine (30 mmol, 2.7 mL) and triethylamine (5 mL) in dichloromethane (150 mL) at ambient temperature. The mixture was stirred for 30 min, washed sequentially with 10% HCl solution, saturated NaHCO$_3$ and water, and then dried over MgSO$_4$. The final compound was isolated by recrystallization from ether:hexanes (5:1) (19.76 mmol). Yield: 98%.

Preparation 5

Synthesis of [4-(6-Aminopyridazin-3-Yl)Piperazin-1-Yl](2-Trifluoromethyl-Phenyl)Methanone A. To a stirred solution of 1-Boc-piperazine (1.96 g, 10.5 mmol) in dichloromethane (50 mL) was added 2-trifluoromethylbenzoyl chloride (2.09 g, 10.0 mmol) as a dichloromethane solution in the presence of triethylamine (3 mL) at 0° C. The resulting mixture was stirred at ambient temperature for 18 hours and then quenched with water (25 mL). The organic phase was washed with water, saturated NaCl, dried over MgSO$_4$ and then concentrated in vacuo to afford the desired product as a pall yellow solid used for next step reaction without further purification.

B. A solution of the compound obtained above (10 mmol) in 50 mL of a 1:4 mixture of trifluoroacetic acid and dichloromethane was stirred at ambient temperature for 5 h. After concentration in vacuo the residue was dissolved in dichloromethane (100 mL) and washed sequentially with 1 N NaOH (10 mL), water, saturated NaCl, and then dried over MgSO$_4$, filtered and concentrated in vacuo to yield piperazin-1-yl-(2-trifluoromethylphenyl)methanone as a light yellow oil. This oil was converted into HCl salt by the addition of 10 mL of 2 N HCl in ether and 100 mL of anhydrous ether to the solution of the compound in 10 mL of dichloromethane. The white solid formed was filtered and dried to yield the HCl salt.

C. A mixture of 3-amino-6-chloropyridazine (0.648 g, 5.00 mmol) and the HCl salt obtained above (7.5 mmol) was heated at 150° C. for 24 hours. To the reaction mixture was added 10 mL of 1 N NaOH and 100 mL of dichloromethane, and the aqueous layer was extracted twice with 100 mL of dichloromethane. The combined organic phase was dried over Na$_2$SO$_4$, evaporated to dryness. The crude compound was purified by flash chromatography to give the title compound as a yellow solid.

Preparation 6

Synthesis of (5-Fluoro-2-Trifluoromethylphenyl) Piperazin-1-Ylmethanone

A. To a solution 1-benzylpiperazine (4.65 g, 4.58 mL, 26.4 mmol) in dichloromethane (200 mL) was added diisopropylethylamine (4.65 g, 6.2 mL, 36.0 mmol) followed by 5-fluoro-2-(trifluoromethyl)benzoyl chloride (5.43 g, 3.63 mL, 23.9 mmol) at 0° C. The reaction solution was stirred at ambient temperature for 16 hours then diluted with dichloromethane (100 mL) and washed with water (3×100 mL). After the solvent was removed in vacuo, the product (9.81 g, quantitative yield) was obtained as a viscous oil which was used for next step reaction without further purification.

B. The viscous oil was diluted in methanol (100 mL) and Pd/C (981 mg) was added. The mixture was stirred under H$_2$ for 16 hours. After filtration, the filtrate was concentrated in vacuo to yield 6.98 g (94%) of the product.

Preparation 7

Synthesis of 6-Piperazin-1-Yl-Pyridazine-3-Carboxylic Acid (2-Cyclopropylethyl)Amide A mixture of piperazine (1.48 g, 17.2 mmol) and 6-chloropyridazine-3-carboxylic acid (2-cyclopropylethyl)amide (1.29 g, 5.73 mmol) in acetonitrile (60 mL) was heated at reflux for 16 hours. After the reaction mixture was cooled, the gummy material was diluted with dichloromethane (50 mL), washed with water (2×20 mL), dried over MgSO$_4$. After filtration, the filtrate was concentrated in vacuo. The crude material was purified by column chromatography eluting with dichloromethane (100%) then with methanol:dichloromethane (1:9) to obtain 1.18 g (75%) of the product as a solid.

Preparation 8

Synthesis of 2-Amino-1-Cyclopropylethanol

A. To a stirred mixture of cyclopropanecarboxyaldehyde (1.00 g, 14.3 mmol) and nitromethane (0.765 g, 14.3 mmol) in MeOH at OC was added dropwise a solution of NaOH (0.57 g) in water. The reaction mixture was kept stirring for 1 hour and a white solid was precipitated. Glacial acetic acid (0.807 mL) was then added to this mixture dropwise. The organic layer was extracted with ether (3×7 mL) and dried over MgSO$_4$ to yield 2-nitro-1-cyclopropylethanol which was used for the next step reaction without further purification.

B. The nitro compound obtained above was dissolved in 4 mL of dry ether and then added dropwise to a stirred slurry of lithium aluminum hydride (0.997 g, 26.3 mmol) in dry ether (30 mL) under refluxing over 1 hour. The reflux was maintained for 2 more hours and then 2-propanol (9 mL) was added and followed by the addition of saturated NaCl solution (3 mL). The mixture was stirred for another 20 minutes and then extracted with mixture of 2-propanol:ether (1:3). 2-Amino-1-cyclopropylethanol was obtained after removal of the solvents and used for next step reaction without further purification.

Preparation 9

Synthesis of 6-Chloropyridazine-3-Carboxylic Acid (2-Cyclopropyl-2-Hydroxyethyl)Amide To the solution of 6-chloropyridazine-3-carboxylic acid (375 mg, 2.37 mmol) in 5 mL of dioxane was added thionyl chloride (420 mg, 3.56 mmol). The mixture was refluxed for 4 hours and the solvent was removed in vacuo. 2-Amino-1-cyclopropylethanol (479 mg, 4.73 mmol) in 5 mL of dioxane was added to the residue and followed by the addition of triethylamine (0.2 mL). The mixture was stirred at ambient temperature overnight. Water was added to the mixture and then extracted with ethyl acetate. The organic extract was separated, washed with water and brine; dried over $Na_2SO_4$. The residue after removal of solvent was purified by column chromatography eluted with ethyl acetate:hexane (70:30) to yield 58 mg of the white desired product.

Preparation 10

Synthesis of Piperazine-1-Yl-(2-Trifluoromethylphenyl)Methanone

A. 2-Trifluoromethylbenzoyl chloride was added dropwise to a cooled (0° C.) and stirred solution of 1-Boc-piperazine (0.100 mol) and triethylamine (0.12 mol) in dichloromethane (250 mL) over 15 minutes. The resulting mixture was stirred at ambient temperature for 6 hours. Water (100 mL) was then added to the mixture and the aqueous phase was extracted with dichloromethane (2×100 mL), the combined organic phase was washed with water and brine; dried over $Na_2SO_4$ and then concentrated in vacuo to afford the product in quantitative yield.

B. A solution of 4-(2-trifluoromethylbenzoyl)piperazine-1-carboxylic acid t-butyl ester obtained above (10 mmol) in a mixture of trifluoroacetic acid and dichloromethane (1:4, 50 mL) was stirred at ambient temperature for 5 hours. After concentration in vacuo, the residue was dissolved in dichloromethane (100 mL) and washed sequentially with saturated sodium bicarbonate, water, and brine; dried over anhydrous $Na_2SO_4$ and concentrated to give piperazine-1-yl-(2-trifluoromethylphenyl)-methanone in 97% yield.

Preparation 11

Synthesis of 6-Piperazin-1-Ylpyridazine-3-Carboxylic Acid (3-Methylbutyl)Amide

A solution of 6-chloropyridazine-3-carboxylic acid (3-methylbutyl)amide (2.52 g, 11.0 mmol) and piperazine (2.83 g, 32.8 mmol) in acetonitrile (30 mL) was heated to refluxed for 2 hours. The solvent was removed by evaporation, the residue was dissolved in water (50 mL) and extracted with dichloromethane (3×100 mL). The organic extract was dried over anhydrous $Na_2SO_4$ and then evaporated. The residue was passed through a pad of silica gel and concentrated to give 6-piperazin-1-yl-pyridazine-3-carboxylic acid (3-methylbutyl)amide (2.68 g, 88% yield). MS (ES+) m/z 278 (M+1).

Preparation 12

Synthesis of 6-Piperazin-1-Ylpyridazine-3-Carboxylic Acid (2-Cyclopropylethyl)Amide A solution of 6-chloropyridazine-3-carboxylic acid (2-cyclopropylethyl)amide (7.8 g, 34 mmol) and piperazine (8.93 g, 103 mmol) in acetonitrile (100 mL) was heated to refluxed for 2 hours. The solvent was removed by evaporation and the residue was dissolved in water (100 mL). The aqueous solution was extracted with dichloromethane (5×100 mL) and the organic extract was dried over anhydrous $Na_2SO_4$, filtered through a pad of silica gel and concentrated to give 6-piperazin-1-ylpyridazine-3-carboxylic acid (2-cyclopropylethyl)amide (8.2 g, 88%). $^1$H NMR (300 MHz, $CDCl_3$) δ 7.90-7.87, 6.89, 3.78-3.50, 3.12-2.90, 1.77-1.49, 0.83-0.60, 0.51-0.36, 0.15-0.01.

Preparation 13

Synthesis of 6-Chloropyridazine-3-Carboxylic Acid [2-(3-Fluorophenyl)Ethyl]Amide To a solution of 6-chloropyridazine-3-carboxylic acid (0.31 g, 1.94 mmol) in dichloromethane (15.5 mL) was added diisopropylethylamine (0.73 mL, 4.19 mmol), followed by 1-hydroxybenzotriazole monohydrate (0.28 g, 2.1 mmol) and 1-(3-dimethylamino)propyl-3-ethylcarbodiimide (0.37 mL, 2.1 mmol). The resulting mixture was stirred for 15 minutes, followed by the addition of 3-fluorophenethylamine (0.28 mL, 2.1 mmol). After stirring for 27 hours at ambient temperature, the reaction mixture was diluted with dichloromethane (200 mL), washed with water (4×25 mL), dried over $Na_2SO_4$ and concentrated in vacuo. Purification by column chromatography eluted with dichloromethane:ethyl acetate (2:1) afforded the product as a white powder (0.205 g). $^1$H NMR (400 MHz, $CDCl_3$) δ 8.26, 8.12, 7.67, 7.28-7.23, 6.95-6.89, 3.80-3.75, 2.95.

Preparation 14

Synthesis of (E)-2-Trifluoromethylcyclopropanecarboxylic Acid

A. To a stirred solution of trimethylsulfoxonium iodide (4.85 g, 22.0 mmol) in DMSO (20 mL) under nitrogen at 25-30° C. was added a dispersion of sodium hydride in mineral oil (0.88 g, 22 mmol) in portions. Upon completion of hydrogen evolution (30 minutes), a solution of ethyl 4,4,4-trifluorocrotonate (3.36 g, 3 mL, 20 mmol) in DMSO (10 mL) was added dropwise so that the temperature did not exceed 35° C. The resulting mixture was stirred at 25-30° C. for 30 minutes and then at 55-60° C. for 1 hour. The mixture was poured into 150 mL of aqueous solution of ammonium chloride (4 g). The solution was extracted with ether and ethereal extract was dried over $Na_2SO_4$ and concentrated to give a crude product.

B. To a solution of the crude product obtained above was added tetrahydrofuran (75 mL), water (38 mL) and lithium hydroxide (3.36 g, 80 mmol). The mixture was stirred and heated to 80° C. for 5.5 hours and then evaporated to remove tetrahydrofuran. The aqueous layer was extracted with hexanes (2×30 mL), acidified with concentrated HCl and then extracted with dichloromethane (3×100 mL). The organic layer was dried over Na$_2$SO$_4$. Removal of the solvent afforded 2-trifluoromethylcyclopropane-carboxylic acid (1.53 g).

Preparation 15

Synthesis of 6-Chloropyridazine-3-Carboxylic Acid Pentylamide

To a flask containing 6-chloropyridazine-3-carboxylic acid (375 mg, 2.37 mmol) in dioxane (5 mL) was added thionyl chloride (420 mg, 0.26 mL, 3.56 mmol). The brown mixture was refluxed for 6 hours under nitrogen with stirring. After cooling to ambient temperature, the solvent was removed by rotary evaporator. The gummy black material was diluted with dioxane (5 mL) and the resulting solution was cooled in an ice-water bath. To the cooled solution was added amyl amine (410 mg, 0.55 mL, 4.74 mmol). The resulting black reaction solution was stirred at ambient temperature for 16 hours under nitrogen. The solvent was removed in vacuo and the residue was dissolved in dichloromethane (25 mL). The solution was washed with water (2×10 mL) and the organic layer was dried over MgSO$_4$, filtered-off the solid and concentrated to afford a gummy material which was purified by column chromatography eluted with dichloromethane to yield 310 mg (57%) of the product as a colourless solid. m.p. 98-101° C. $^1$H NMR (300 MHz, CDCl$_3$) δ 8.28, 8.05, 7.68, 3.51, 1.69-1.63, 0.90. MS (ES+) m/z 228 (M+1).

Preparation 16

Synthesis of 3-Cyclopropylpropylamine

A. p-Toluenesulfonyl chloride (7.20 g, 37.8 mmol) was added to a cooled (0° C.) solution of 2-cyclopropylethanol (4.00 g, 46.4 mmol) in pyridine (10 mL) and dichloromethane (60 mL). The reaction mixture was stirred at ambient temperature overnight, then diluted with ether (200 mL) and washed sequentially with water, 10% HCl, water and brine and then dried over anhydrous Na$_2$SO$_4$. Toluene-4-sulfonic acid 2-cyclopropylethyl ester (8.1 g, 89%) was obtained after removal of solvent and used for next step reaction without further purification.

B. A mixture of toluene-4-sulfonic acid 2-cyclopropylethyl ester (8.1 g, 33.7 mmol), sodium cyanide (5.0 g, 102 mmol) and tetrabutylammonium iodide (0.5 g) in DMF (30 mL) was heated at 90° C. overnight. The reaction mixture was then cooled to ambient temperature, diluted with ether (200 mL), washed with water and brine, and dried over anhydrous Na$_2$SO$_4$. 3-Cyclopropylpropionitrile (3.2 g, 99%) was obtained after removal of solvent.

C. Concentrated sulfuric acid (2.73 mL) was added drop wise to a vigorously stirred ethereal solution of lithium aluminum hydride (3.792 g, 99.43 mmol) in 40 mL of ether at 0° C. The reaction mixture was then warmed to ambient temperature and stirred for 1 hour. A solution of 3-cyclopropylpropionitrile (3.085 g, 32.47 mmol) in ether (10 mL) was added drop wise. The resulting mixture was heated at reflux for 2 hours, then cooled to 0° C., and subsequently slowly quenched with water. A solution of NaOH (2 g in 18 mL of H$_2$O) was added and organic phase was decanted from the resulting aluminum hydroxide precipitate, which was washed with ether (3×20 mL). All ethereal portions were combined, and the solvent was distilled off and 3-cyclopropylproylamine was obtained as a light yellow liquid (2.01 g, 62.5%).

Preparation 17

Synthesis of 6-(3,5-Dimethyl-Piperazin-1-Yl)Pyridazine-3-Carboxylic Acid (2-Cyclopropylethyl) Amide To a solution of 6-chloropyridazine-3-carboxylic acid (2-cyclopropylethyl)amide (0.57 g, 2.52 mmol) and Bu$_4$NBr (0.16 g, 0.50 mmol) in dioxane (20 mL) was added 1,8-diazabicylco[5.4.0]undec-7-ene (DBU) (0.75 mL, 0.77 g, 5.04 mmol). The brown reaction mixture was heated at reflux for 16 hours, then cooled to ambient temperature. The solvent was removed in vacuo. The crude material was diluted with ethyl acetate (50 mL). The solution was washed with water (3×20 mL), dried over MgSO$_4$. After filtration, the solvent of the filtrate was removed in vacuo. The product was isolated as a brown gummy material (0.72 g, 74%) that was directly used for the next step without further purification.

Preparation 18

Synthesis of 6-[1,4]Diazepan-1-Yl-Pyridazine-3-Carboxylic Acid (2-Cyclopropylethyl)Amide A. A mixture of 6-chloropyridazine-3-carboxylic acid (2-cyclopropylethyl)amide (0.15 g, 0.665 mmol), [1,4]diazepane-1-carboxylic acid tert-butyl ester (0.133 g, 0.665 mmol) and triethylamine (0.093 mL, 0.665 mmol) was heated to reflux in toluene for 18 h. The solvent was removed in vacuo, and the residue was purified by flash column chromatography to yield the product (0.226 g, 87%) which was used for the next step reaction without further purification.

B. The product obtained above was dissolved in a 2:1 mixture of dichloromethane/trifluoroacetic acid, and the mixture was stirred for 15 minutes. The solvent was then removed in vacuo. The residue was diluted with dichloromethane, and the resulting solution was washed with 10% aqueous sodium hydroxide solution, dried and concentrated to yield 6-[1,4] diazepan-1-yl-pyridazine-3-carboxylic acid (2-cyclopropylethyl)amide.

Preparation 19

Synthesis of 6-Chloropyridazine-3-Carboxylic Acid (2-Cyclobutylethyl)Amide

A. To a solution of cyclobutanemethanol (4.00 g, 46.4 mmol) in dichloromethane (60 mL) was added pyridine (10 mL), followed by the addition of p-toluenesulfuryl chloride (7.20 g, 37.8 mmol) at 0° C. The reaction mixture was stirred for 23 h at ambient temperature, and then diluted with diethyl ether (350 mL), washed sequentially with water, 1% aqueous HCl solution, water and brine. The organic layer was dried over Na$_2$SO$_4$ and concentrated in vacuo to give the product (9.00 g, 80.7%).

B. To a solution of toluene-4-sulfonic acid cyclobutylmethyl ester (9.00 g, 37.5 mmol) in DMF (34 mL) was added sodium cyanide (5.62 g, 114.6 mmol) and tetra-n-butylammonium iodide (0.56 g, 1.41 mmol). The reaction mixture was stirred at 90 to 95° C. for 6.5 h. After cooled down to ambient temperature, the reaction mixture was diluted with diethyl ether (450 mL), washed with water and brine. The organic layer was dried over Na$_2$SO$_4$ and concentrated at atmosphere pressure to give a product (3.50 g).

C. Concentrated sulfuric acid (1.71 mL, 32.6mmol) was added dropwise to a vigorously stirred solution of lithium aluminum hydride (2.47 g, 65.1 mmol) in 65 mL of ether at 0° C. The reaction mixture was warmed to ambient temperature and stirred for 1 h, and a solution of cyclobutylacetonitrile (2 g, 21.03 mmol) in 9 mL of ether was added dropwise. The resulting mixture was heated at reflux for 3.5 h and then stirred at ambient temperature for 21 h. The reaction mixture was cooled to 0° C., and slowly quenched with water (16 mL). A solution of sodium hydroxide (7.85 g) in water (69 mL) was added, and the organic phase was decanted from the resulting aluminum hydroxide precipitate, which was rinsed with three 50-mL portions of ether. All ethereal portions were combined, and the solvent was distilled off to leave of 2-cyclobutylethylamine as a colorless liquid (1.9 g, 91%).

D. To a 100-mL round bottom flask, 6-oxo-1,6-dihydropyridazine-3-carboxylic acid monohydrate (0.64 g, 3.6 mmol), chloroform (14 mL), dimethylformamide (0.1 mL) and thionyl chloride (1.2 mL) were added. The reaction mixture was stirred at 60° C. for 16 h. The reaction mixture was evaporated in vacuo to dryness. The solid residue was dissolved in dichloromethane (13 mL) and added dropwise to the mixture of cyclobutylethylamine (0.47 g, 4.74 mmol) and triethylamine (0.8 mL) in dichloromethane (25 mL) at ambient temperature. After stirred for 1 h, the reaction mixture was diluted with dichloromethane (100 mL) and washed sequentially with 10% aqueous HCl solution, saturated $NaHCO_3$ and water. The organic layer was dried over $Na_2SO_4$ and evaporated in vacuum. Purification by column chromatography (silica gel, hexane/EtOAc (2:1)) afforded the product as a white powder (0.572 g, 59%).

$^1$H NMR (300 MHz, $CDCl_3$) δ 8.25, 7.97, 7.65, 3.42, 2.36, 2.08, 1.91-1.59.

Preparation 20

Synthesis of 3-Cyclobutylpropylamine

A. A solution of trimethylphosphine in toluene (1 M, 60 mL, 60 mmol) at 0° C. under nitrogen was diluted with toluene (30 mL) and tetrahydrofuran (30 mL). Iodoacetonitrile (4.2 mL, 9.69 g, 58 mmol) was then added dropwise while stirring vigorously, whereby a colorless solid precipitated. When the addition was finished, the ice-bath was removed and stirring was continued at ambient temperature for 51 h. The mixture was filtered, and the solid was washed with toluene and dried under reduced pressure. Recrystallization from acetonitrile (37.5 mL) to give the compound as colorless crystals (9.89 g, yield: 70%).

B. To a mixture of cyclobutanemethanol (0.861 g, 10 mmol) and (cyanomethyl)-trimethylphosphonium iodide (6.20 g, 25.5 mmol) were added propionitrile (20 mL) and diisopropylethylamine (5.5 mL, 32 mmol), and the mixture was stirred at 97° C. for 48 h. Water (1 mL, 55.5 mmol) was added, and stirring at 97° C. was continued for another 18 h. Water (125 mL) and concentrated hydrochloric acid (5 mL, 60 mmol) were added, and the mixture was extracted with dichloromethane (3×100 mL). The combined extracts were washed once with brine, dried with magnesium sulfate, and concentrated at atmosphere pressure to give the product (1.09 g).

C. Concentrated sulfuric acid (3.15 mL, 60.05 mmol) was added dropwise to a vigorously stirred solution of lithium aluminum hydride (4.35 g, 113.8 mmol) in 114 mL of ethyl ether at 0° C. The reaction mixture was warmed to ambient temperature and stirred for 1 h, and a solution of cyclobutylpropionitrile (1.09 g, 10 mmol) in 15 mL of ether was added dropwise. The resulting mixture was heated at reflux for 2 h and then stirred at ambient temperature for 48 h. The reaction mixture was cooled to 0° C., and slowly quenched with water (12 mL). A solution of sodium hydroxide (5.89 g) in water (52 mL) was added, and the organic phase was decanted from the resulting aluminum hydroxide precipitate, which was rinsed with three 50-mL portions of ether. All ethereal portions were combined, and the solvent was distilled off to leave 0.36 g (32%) of 2-cyclobutylpropylamine as a colorless liquid.

Preparation 21

Synthesis of
6-Piperazin-1-Ylpyridazine-3-Carboxylic Acid
(2-Cyclobutylethyl)Amide To a solution of 6-chloropyridazine-3-carboxylic acid (2-cyclobutylethyl)-amide (1.2 g, 5.00 mmol) in acetonitrile (40 mL) was added piperazine (1.29 g, 15.00 mmol). The reaction mixture was heated to reflux overnight. The mixture was evaporated and the solid residue was taken in ethyl acetate (100 mL) and water (100 mL). The organic layer was separated and the aqueous layer was extracted with ethyl acetate (2×100 mL). The combined ethyl acetates were dried over $Na_2SO_4$ and concentrated in vacuo to give the title compound as yellow solid (1.14 g, 78.4% yield).

Preparation 22

Synthesis of 2,2-(Dimethylcyclopropyl)Methylamine

Lithium aluminum hydride (7.77 g, 0.194 mmol) was added to a solution of 2,2-dimethylcyclopropanecarboxamide (10.0 g, 88.3 mmol) in THF (200 mL) at 0° C. The reaction mixture was heated to reflux for 5 h, then cooled to 0° C., quenched with water, and extracted with diethyl ether. The combined ether layer was dried over anhydrous $Na_2SO_4$, and distilled to yield the title compound in 36% yield (3.2 g). b.p. 94-96° C. $^1$H NMR (300 MHz, $CDCl_3$) δ 2.68-2.53, 1.13, 1.03, 1.00, 0.70-0.61, 0.38-0.34, −0.02-0.05.

Preparation 23

Syhthesis of 6-[4-(2-Trifluoromethylbenzoyl)Piperazin-1-Yl]Pyridazine-3-Carboxylic Acid A. To a methanol solution of 6-oxo-1,6-dihydropyridazine-3-carboxylic acid monohydrate (5.00 g, 31.6 mmol) was added thionyl chloride (0.36 mL, 0.59 g, 4.94 mmol). The reaction mixture was heated to reflux at 80° C. for 16 h. The product crystallized after the reaction mixture was cooled down to ambient temperature. The crystals were collected and washed with methanol and the mother liquor was concentrated and crystallized again. The total amount of product isolated was 4.954 g (100% yield).

B. A mixture of 6-hydroxypyridazine-3-carboxylic acid methyl ester obtained above and phosphorous oxychloride were carefully heated to reflux temperature and maintained there for 2.5 h. The reaction mixture was then cooled and evaporated in vacuo to remove excess phosphorylchloride, and the residue was then poured into ice water. The precipitate was collected by filtration, washed with saturated $NaHCO_3$ and water, and dried under vacuum to yield the product as a yellow solid (4.359 g, 79% yield).

C. To a solution of 6-chloropyridazine-3-carboxylic acid methyl ester obtained above (4.359 g, 25.3 mmol) in dioxane (145 mL) was treated with 1-(2-trifluoromethyl-benzoyl)piperazine hydrochloric acid salt (7.80 g, 26.5 mmol) in the presence of $K_2CO_3$ (10.14 g, 73.4 mmol) and tetra-n-butylammonium iodide (0.071 g, 0.192 mmol). The reaction mixture was heated to reflux for 24 h and evaporated to remove dioxane. The residue was purified by column chromatography to afford the desired product (8.666 g, 87% yield).

D. To a solution of 6-[4-(2-trifluoromethylbenzoyl)piperazin-1-yl]pyridazine-3-carboxylic acid methyl ester (4.436 g, 11.25 mmol) in tetrahydrofuran (50 mL) and water (25 mL) was added lithium hydroxide monohydrate (2.30 g, 54.81 mmol). The reaction mixture was stirred at ambient temperature for 23 h and the pH of the solution was adjusted to ~3 with concentrate hydrochloric acid (5.3 mL) at 0° C. The mixture was concentrated. Ethyl acetate (100 mL) was added to the residue and the product was precipitated. The solid was collected by filtration, washed with ethyl acetate and dried in vacuo to afford the title compound (3.60 g). The aqueous layer was extracted with ethyl acetate, dried over $Na_2SO_4$ and concentrated to give the second portion of title compound (0.463 g). The total amount of product was 4.063 g (95% yield).

Preparation 24

Synthesis of
6-Piperazin-1-Ylpyridazine-3-Carboxylic Acid
Pent-4-Enylamide

A. To a solution of 4-penten-1-ol (4.8 mL, 4.00 g, 46.4 mmol) in dichloromethane (60 mL) was added pyridine (10 mL), followed by the addition of p-toluenesulfuryl chloride (7.2 g, 37.8 mmol) at 0° C. The reaction mixture was stirred for 21 h at ambient temperature. The reaction mixture was then diluted with diethyl ether (350 mL), washed sequentially with water, 1% HCl, water and brine. The organic layer was dried over $Na_2SO_4$ and concentrated to affors the product in 93% yield (8.48 g) which was used for the next step reaction without further purification.

B. To a solution of toluene-4-sulfonic acid pent-4-enyl ester obtained above (3.42 g, 14.3 mmol) in THF (55 mL) was added ammonium hydroxide (ammonia content 28.0-30.0%) (100 mL, 1532.6 mmol). The reaction mixture was stirred at ambient temperature for 5 days. The reaction mixture was extracted with diethyl ether. The combined ether solution was dried over $Na_2SO_4$ and distilled under atomophere at 50° C. to yield a THF solution of pent-4-enylamine, which was used for next step reaction without further purification.

C. 6-Oxo-1,6-dihydropyridazine-3-carboxylic acid monohydrate (1.60 g, 10.1 mmol), chloroform (36 mL), dimethylformamide (0.25 mL) and thionyl chloride (3.05 mL) were added to a 100-mL round bottom flask. The reaction mixture was stirred at 69° C. for 43 h and then evaporated to dryness. The solid residue was dissolved in dichloromethane and the solution was added dropwise to the mixture of pent-4-enylamine in THF prepared above and triethylamine at ambient temperature. After stirred for 1 h, the reaction mixture was diluted with dichloromethane and washed with 10% HCl, saturated $NaHCO_3$ and water. The organic layer was dried over $Na_2SO_4$ and evaporated in vacuum. Purification by column chromatography afforded the product as a white powder (1.08 g, 61.6% yield).

D. To a solution of 6-chloropyridazine-3-carboxylic acid pent-4-enylamide synthesized above (1.08 g, 4.79 mmol) in acetonitrile (39 mL) was added piperazine (1.25 g, 14.5 mmol). The reaction mixture was heated to reflux overnight (TLC indicated the reaction was complete). The mixture was evaporated and the solid residue was dissolved in a mixture of ethyl acetate (100 mL) and water (100 mL). The organic layer was separated and the aqueous layer was extracted with ethyl acetate. The combined ethyl acetate layer were dried over $Na_2SO_4$ and concentrated to yield the title compound as a yellow solid (1.169 g, 88.6% yield).

The syntheses of compounds of this invention are illustrated by, but not limited to the following examples.

EXAMPLE 1

Synthesis of 4-Methylpentanoic Acid {6-[4-(2-Trifluoromethylbenzoyl)-Piperazin-1-Yl]Pyridazin-3-Yl}Amide To a stirred solution of [4-(6-aminopyridazin-3-yl)piperazin-1-yl](2-trifluoromethyl-phenyl)methanone (0.226 g, 0.645 mmol) in tetrahydrofuran (10.0 mL) was added 4-methylpentanoic acid (0.500 g, 4.30 mmol) followed by (3-dimethylaminopropyl)-ethyl carbodiimide (1.0 mL). The mixture was stirred at ambient temperature overnight. Water was added and the mixture was extracted with ethyl acetate. The combined organic layer was dried with $Na_2SO_4$, concentrated, and the residue was dissolved again in a small amount of ethyl acetate. The solid, which precipitated by dropwise addition of hexane was filtered off and dried in vacuum to give the title product (0.070 g) as a white solid in 24% yield. $^1$H NMR (300 MHz, $CDCl_3$) δ 9.15, 8.36, 7.74, 7.63, 7.56, 7.36, 7.05, 4.03-3.98, 3.93-3.89, 3.69-3.62, 3.55-3.53, 3.33-3.31, 2.51, 1.63-1.61, 0.91.

EXAMPLE 1.1

4-Phenyl-N-{6-[4-(2-Trifluoromethylbenzoyl)Piperazin-1-Yl]Pyridazin-3-Yl}Butyramide Following the procedure of Example 1, making variations only as required to use 4-phenylbutyric acid in place of 4-methylpentanoic acid to react with [4-(6-aminopyridazin-3-yl)piperazin-1-yl](2-trifluoromethylphenyl)methanone, the title compound was obtained as a white powder (9% yield). $^1$H NMR (300 MHz, $CDCl_3$) δ 9.13, 8.36, 7.74, 7.62, 7.56, 7.36, 7.28-7.25, 7.19-7.16, 7.05, 4.03-3.98, 3.93-3.88, 3.69-3.60, 3.54-3.52, 3.33-3.31, 2.70, 2.52, 2.06.

EXAMPLE 1.2

4-(4-Methoxyphenyl)-N-{6-[4-(2-Trifluoromethylbenzoyl)Piperazin-1-Yl]Pyridazin-3-Yl}Butyramide Following the procedure of Example 1, making variations only as required to use 4-(4-methoxyphenyl)butyric acid in place of 4-methylpentanoic acid to react with [4-(6-aminopyridazin-3-yl)piperazin-1-yl](2-trifluoromethylphenyl)-methanone, the title compound was obtained as a white powder (20% yield). $^1$H NMR (300 MHz, $CDCl_3$) δ 9.14, 8.29, 7.67, 7.55, 7.49, 7.30, 7.01, 6.98, 6.73, 3.95-3.91, 3.86-3.81, 3.70, 3.61-3.55, 3.48-3.45, 3.26-3.24, 2.57, 2.45, 1.96.

EXAMPLE 2

Synthesis of 2-Benzyloxy-N-{6-[4-(2-Trifluoromethylbenzoyl)Piperazin-1-Yl]-Pyridazin-3-Yl}Acetamide To a stirred solution of [4-(6-aminopyridazin-3-yl)piperazin-1-yl]-(2-trifluoromethylphenyl)methanone (1.30 g, 3.7 mmol) in dichloromethane (60 mL) was added diisopropylethylamine (1.5 g), followed by 1-hydroxybenzotriazole monohydrate (1.1 g) and N-(3-dimethylaminopropyl)-N'- ethylcarbodiimide (2 mL). The resulting mixture was stirred for 15 minutes and then benzyloxyacetic acid (1.2 mL) was added. After stirring for 2 hours the reaction mixture was washed with 10% HCl, 1 N NaOH and water, dried over anhydrous $Na_2SO_4$ and concentrated in vacuo to afford the final amide as a dark yellow oil. The oil was purified by column chromatography (dichloromethane:MeOH=98:2) providing 1.64 g of pure final compound as a white solid in 89% yield. $^1$H NMR (300 MHz, $CDCl_3$) δ 9.12, 8.29, 7.72, 7.63-7.49, 7.35-7.33, 6.99, 4.65, 4.10, 4.05-3.83, 3.66-3.54, 3.33-3.29. MS (ES+) m/z 500.2 (M+1).

EXAMPLE 2.1

4-Cyclohexyl-N-{6-[4-(2-Trifluoromethylbenzoyl) Piperazin-1-Yl]Pyridazin-3-Yl}Butyramide Following the procedure of Example 2, making variations only as required to use 4-cyclohexylbutyric acid in place of benzyloxyacetic acid to react with [4-(6-aminopyridazin-3-yl)piperazin-1-yl](2-trifluoromethylphenyl)methanone, the title compound was obtained as a white powder (18% yield). $^1$H NMR (300 MHz, $CDCl_3$) δ 9.04, 8.32, 7.68, 7.56, 7.49, 7.30, 7.04-7.00, 3.99-3.23, 2.40, 1.89-1.83, 1.69-0.84.

EXAMPLE 2.2

2-Ethoxy-N-{6-[4-(2-Trifluoromethylbenzoyl)Piperazin-1-Yl]Pyridazin-3-Yl}-Acetamide Following the procedure of Example 2, making variations only as required to use ethoxyacetic acid in place of benzyloxyacetic acid to react with [4-(6-aminopyridazin-3-yl)piperazin-1-yl](2-trifluoromethylphenyl)methanone, the title compound was obtained as a yellow solid (67% yield). $^1$H NMR (300 MHz, $CDCl_3$) δ 9.18, 8.35, 7.75, 7.63, 7.56, 7.37, 7.04, 4.08, 4.04-3.88, 3.70-3.64, 3.60-3.58, 3.35-3.33, 1.31. MS (ES+) m/z 438.4 (M+1).

EXAMPLE 2.3

2-Cyclopropylmethoxy-N-{6-[4-(2-Trifluoromethylbenzoyl)Piperazin-1-Yl]-Pyridazin-3-Yl}Acetamide Following the procedure of Example 2, making variations only as required to use cyclopropylmethoxyacetic acid in place of benzyloxyacetic acid to react with [4-(6-aminopyridazin-3-yl)piperazin-1-yl](2-trifluoromethylphenyl) methanone, the title compound was obtained as a white powder (41% yield). $^1$H NMR (300 MHz, $CDCl_3$) δ 9.17, 8.32, 7.72, 7.61, 7.54, 7.35, 4.10, 4.01-3.88, 3.69-3.61, 3.57-3.55, 3.43, 3.33-3.30, 1.14-1.08, 0.61-0.57, 0.27-0.24. MS (ES+) m/z 464.5 (M+1).

EXAMPLE 2.4

2-(2-Methoxyethoxy)-N-{6-[4-(2-Trifluoromethylbenzoyl)Piperazin-1-Yl]-Pyridazin-3-Yl}Acetamide Following the procedure of Example 2, making variations only as required to use (2-methoxyethoxy)acetic acid in place of benzyloxyacetic acid to react with [4-(6-aminopyridazin-3-yl)piperazin-1-yl](2-trifluoromethylphenyl)methanone, the title compound was obtained as a white powder (72% yield). $^1$H NMR (300 MHz, $CDCl_3$) δ 9.53, 8.34, 7.74, 7.63, 7.56, 7.34, 7.02, 4.16, 4.04-3.89, 3.80-3.77, 3.69-3.65, 3.63-3.61, 3.59-3.56, 3.46, 3.34-3.32. MS (ES+) m/z 468.3 (M+1).

EXAMPLE 2.5

2,2,3,3-Tetramethylcyclopropanecarboxylic Acid {6-[4-(2-Trifluoromethylbenzoyl)Piperazin-1-Yl] Pyridazin-3-Yl}Amide Following the procedure of Example 2, making variations only as required to use 2,2,3,3-tetramethylcyclopropanecarboxylic acid in place of benzyloxyacetic acid to react with [4-(6-aminopyridazin-3-yl)piperazin-1-yl](2-trifluoromethylphenyl)-methanone, the title compound was obtained as a white powder (48% yield). $^1$H NMR (300 MHz, $CDCl_3$) δ 8.77, 8.28, 7.72, 7.60, 7.53, 7.34, 6.99, 4.01-3.85, 3.63-3.60, 3.52-3.45, 3.31-3.27, 1.78-1.74, 1.28, 1.20. MS (ES+) m/z 476.3 (M+1).

EXAMPLE 2.6

Cyclopropanecarboxylic Acid {6-[4-(2-Trifluoromethylbenzoyl)Piperazin-1-Yl]Pyridazin-3-Yl}Amide Following the procedure of Example 2, making variations only as required to use cyclopropanecarboxylic acid in place of benzyloxyacetic acid to react with [4-(6-aminopyridazin-3-yl)piperazin-1-yl](2-trifluoromethylphenyl)methanone, the title compound was obtained as a white powder (32% yield). $^1$H NMR (300 MHz, $CDCl_3$) δ 10.07, 8.40, 7.72, 7.61, 7.53, 7.34, 7.03, 4.02-3.82, 3.67-3.55, 3.49-3.46, 3.30-3.27, 2.09-2.01, 1.09-1.04, 0.88-0.82. MS (ES+) m/z 420.2 (M+1).

EXAMPLE 2.7

1-Trifluoromethylcyclopropanecarboxylic Acid {6-[4-(2-Trifluoromethylbenzoyl)Piperazin-1-Yl]Pyridazin-3-Yl}Amide Following the procedure of Example 2, making variations only as required to use 1-trifluoromethylcyclopropanecarboxylic acid in place of benzyloxyacetic acid to react with [4-(6-aminopyridazin-3-yl)piperazin-1-yl](2-trifluoromethylphenyl)-methanone, the title compound was obtained as a white powder (16% yield). $^1$H NMR (300 MHz, $CDCl_3$) δ 8.62, 8.18, 7.74, 7.63, 7.56, 7.34, 7.01, 4.03-3.89, 3.71-3.62, 3.60-3.58, 3.34-3.32, 1.54-1.52, 1.39-1.36. MS (ES+) m/z 487.9 (M+1).

EXAMPLE 2.8

N-{6-[4-(2-Trifluoromethylbenzoyl)Piperazin-1-Yl] Pyridazin-3-Yl}-2-(3,3,3-Trifluoropropoxy)Acetamide Following the procedure of Example 2, making variations only as required to use (3,3,3-trifluoropropoxy)acetic acid in place of benzyloxyacetic acid to react with [4-(6-aminopyridazin-3-yl)piperazin-1-yl](2-trifluoromethylphenyl) methanone, the title compound was obtained as a white powder (50% yield). $^1$H NMR (300 MHz, $CDCl_3$) δ 9.03, 8.32, 7.75, 7.63, 7.56, 7.37, 7.03, 4.13, 4.03-3.98, 3.94-3.89, 3.84, 3.71-3.63, 3.60-3.58, 3.35-3.32, 2.56-2.48. MS (ES+) m/z 506.5 (M+1).

EXAMPLE 2.9

3-Methoxy-N-{6-[4-(2-Trifluoromethylbenzoyl) Piperazin-1-Yl]Pyridazin-3-Yl}Propionamide Following the procedure of Example 2, making variations only as required to use 3-methoxypropionic acid in place of benzyloxyacetic acid to react with [4-(6-aminopyridazin-3- yl)piperazin-1-yl](2-trifluoromethylphenyl)methanone, the title compound was obtained as a white powder (11% yield). $^1$H NMR (300 MHz, CDCl$_3$) δ 9.44, 8.31, 7.74, 7.63, 7.55, 7.36, 7.02, 4.02-3.98, 3.94-3.89, 3.73, 3.70-3.61, 3.57-3.54, 3.43, 3.33-3.31, 2.73. MS (ES+) m/z 438.1 (M+1).

EXAMPLE 2.10

3-Phenoxy-N-{6-[4-(2-Trifluoromethylbenzoyl)Piperazin-1-Yl]Pyridazin-3-Yl}Propionamide Following the procedure of Example 2, making variations only as required to use 3-phenoxypropionic acid in place of benzyloxyacetic acid to react with [4-(6-aminopyridazin-3-yl)piperazin-1-yl](2-trifluoromethylphenyl)methanone, the title compound was obtained as a white powder (52% yield). $^1$H NMR (300 MHz, CDCl$_3$) δ 10.08, 8.40, 7.74, 7.61, 7.55, 7.34, 7.26-7.22, 7.05, 6.93, 6.88, 4.34, 4.01-3.96, 3.92-3.86, 3.68-3.60, 3.55-3.53, 3.29-3.27, 3.08. MS (ES+) m/z 500.3 (M+1).

EXAMPLE 2.11

3-(4-Fluorophenyl)-N-{6-[4-(2-Trifluoromethylbenzoyl)Piperazin-1-Yl]Pyridazin-3-Yl}Propionamide Following the procedure of Example 2, making variations only as required to use 3-(4-fluorophenyl)propionic acid in place of benzyloxyacetic acid to react with [4-(6-aminopyridazin-3-yl)piperazin-1-yl](2-trifluoromethylphenyl)methanone, the title compound was obtained as a white solid (58.5% yield). $^1$H NMR (300 MHz, CDCl$_3$) δ 10.33, 8.40, 7.78, 7.67, 7.60, 7.36, 7.14, 7.08, 6.85, 3.90, 3.51, 3.20, 3.02, 2.92. MS (ES+) m/z 502.7 (M+1).

EXAMPLE 2.12

2-Butoxy-N-{6-[4-(2-Trifluoromethylbenzoyl)Piperazin-1-Yl]Pyridazin-3-Yl}Acetamide Following the procedure of Example 2, making variations only as required to use butoxyacetic acid in place of benzyloxyacetic acid to react with [4-(6-aminopyridazin-3-yl)piperazin-1-yl](2-trifluoromethylphenyl)methanone, the title compound was obtained as a white powder (40.8% yield). $^1$H NMR (300 MHz, CDCl$_3$) δ 9.19, 8.35, 7.72, 7.55, 7.33, 7.03, 4.05, 3.94, 3.60, 3.31, 1.64, 1.43, 0.93. MS (ES+) m/z 465.6 (M+1).

EXAMPLE 2.13

2-Methyl-1-{6-[4-(2-Trifluoromethylbenzoyl)Piperazin-1-Yl]Pyridazin-3-Ylcarbamoyl}Propylammonium Chloride Following the procedure of Example 2, making variations only as required to use 2-amino-3-methylbutyric acid in place of benzyloxyacetic acid to react with [4-(6-aminopyridazin-3-yl)piperazin-1-yl](2-trifluoromethylphenyl)methanone and then treated with HCl, the title compound was obtained as a white powder of HCl salt (48% yield). $^1$H NMR (300 MHz, DMSO-d$_6$) δ 11.53, 8.50, 8.12, 7.84, 7.76, 7.68, 7.62, 7.54, 3.90, 3.36, 3.25, 2.20, 0.98. MS (ES+) m/z 451.2 (M+1).

EXAMPLE 2.14

5-[1,2]Dithiolan-3-Yl-Pentanoic Acid {6-[4-(2-Trifluoromethylbenzoyl)Piperazin-1-Yl]Pyridazin-3-Yl}Amide Following the procedure of Example 2, making variations only as required to use lipoic acid in place of benzyloxyacetic acid to react with [4-(6-aminopyridazin-3-yl)piperazin-1-yl](2-trifluoromethylphenyl)methanone, the title compound was obtained as a white solid (yield 8%). $^1$H NMR (300 MHz, CDCl$_3$) δ 10.11, 8.37, 7.72, 7.61, 7.53, 7.35, 7.04, 4.08-3.84, 3.70-3.57, 3.56-3.46, 3.33-3.30, 3.17-3.02, 2.59, 2.39, 1.84, 1.78-1.56, 1.51-1.37. $^{13}$C NMR (300 MHz, CDCl$_3$): 172.52, 167.57, 157.94, 150.00, 134.42, 132.38, 129.45, 127.79, 127.29, 127.14, 126.93, 126.88, 126.82, 121.92, 116.27, 56.34, 46.47, 45.65, 45.33, 41.25, 40.26, 38.49, 37.05, 34.74, 28.85, 25.14. MS (ES+) m/z 540.1 (M+1).

EXAMPLE 2.15

2-(2-Cyclopropylethoxy)-N-{6-[4-(2-Trifluoromethylbenzoyl)Piperazin-1-Yl]-Pyridazin-3-Yl}Acetamide Following the procedure of Example 2, making variations only as required to use 5-(2-cyclopropylethoxy)acetic acid in place of benzyloxyacetic acid to react with [4-(6-aminopyridazin-3-yl)piperazin-1-yl](2-trifluoromethylphenyl)methanone, the title compound was obtained as a white solid (0.056 g, 41% yield). $^1$H NMR (300 MHz, CDCl$_3$) δ 9.15, 8.32, 7.73-7.7, 7.61-7.53, 7.35-7.33, 7.0, 4.07, 3.97-3.89, 3.64, 3.57-3.54, 3.32-3.29, 1.57-1.51, 0.85-0.75, 0.52-0.48, 0.09-0.07. $^{13}$C NMR (75 MHz, CDCl$_3$) δ 168.8, 167.5, 158.3, 148.3, 134.4, 132.3, 129.3, 127.7, 127.5, 127.2, 127.1, 126.8, 126.7, 126.3, 125.4, 121.8, 120.9, 115.5, 72.2, 70.2, 46.4, 45.5, 45.1, 41.2, 34.5, 7.8, 4.2. MS (ES+) m/z 478.3 (M+1).

EXAMPLE 3

Synthesis of 6-[4-(Isoxazole-5-Carbonyl)Piperazin-1-Yl]Pyridazine-3-Carboxylic Acid (3-Methylbutyl)Amide To a stirred solution of 6-piperazin-1-yl-pyridazine-3-carboxylic acid (3-methylbutyl)amide (277 mg, 1 mmol) in dichloromethane (15 mL) was added isoxazole-5-carbonyl chloride (1.0 mmol) as a dichloromethane solution in the presence of triethylamine (0.4 mL) at ambient temperature. After 1 hour the mixture was evaporated and the residue was subjected to column chromatography. Final product was isolated as a solid (0.107 g, yield 29%). $^1$H NMR (300 MHz, CDCl$_3$) δ 8.34, 8.05, 7.83, 7.00, 6.86, 3.90-3.84, 3.51-3.45, 1.75-1.62, 1.53-1.46, 0.92. MS (ES+) m/z 373.3 (M+1).

EXAMPLE 3.1

6-[4-(1-Methyl-5-Trifluoromethyl-1H-Pyrazole-4-Carbonyl)Piperazin-1-Yl]-Pyridazine-3-Carboxylic Acid (3-Methylbutyl)Amide Following the procedure of Example 3, making variations only as required to use 1-methyl-5-trifluoromethyl-1H-pyrazole-4-carbonyl chloride in place of isoxazole-5-carbonyl chloride to react with 6-piperazin-1-yl-pyridazine-3-carboxylic acid (3-methylbutyl)amide, the title compound was obtained as a white powder (47% yield). $^1$H NMR (300 MHz, CDCl$_3$) δ 8.04, 7.82, 7.54, 6.99, 3.97, 3.90-3.54, 3.51-3.44, 1.75-1.62, 1.53-1.46, 0.92. MS (ES+) m/z 454.3 (M+1).

EXAMPLE 3.2

6-[4-(4-Methylpiperazine-1-Carbonyl)Piperazin-1-Yl]Pyridazine-3-Carboxylic Acid (3-Methylbutyl) Amide Following the procedure of Example 3, making variations only as required to use 4-methylpiperazine-1-carbonyl chloride in place of isoxazole-5-carbonyl chloride to react with 6-piperazin-1-yl-pyridazine-3-carboxylic acid (3-methylbutyl)amide, the title compound was obtained as a white powder (79% yield). $^1$H NMR (300 MHz, CDCl$_3$) δ 8.01, 7.83, 6.96, 3.77-3.73, 3.51-3.44, 3.42-3.38, 3.36-3.33, 2.44-2.41, 2.31, 1.75-1.62, 1.48, 0.92. MS (ES+) m/z 404.4 (M+1).

EXAMPLE 3.3

6-(4-Benzoylpiperazin-1-Yl)Pyridazine-3-Carboxylic Acid (2-Cyclopropylethyl)Amide Following the procedure of Example 3, making variations only as required to use benzoyl chloride in place of isoxazole-5-carbonyl chloride to react with 6-piperazin-1-yl-pyridazine-3-carboxylic acid (2-cyclopropylethyl)amide, the title compound was obtained as a white solid (92% yield). $^1$H NMR (300 MHz, CDCl$_3$) δ 8.04, 7.97, 7.44, 6.98, 3.99-3.62, 3.55, 1.50, 0.80-0.66, 0.48-0.42, 0.11-0.06. MS (ES+) m/z 380.2 (M+1).

EXAMPLE 3.4

6-[4-(2-Ethylbutyryl)Piperazin-1-Yl]Pyridazine-3-Carboxylic Acid (2-Cyclopropylethyl)Amide Following the procedure of Example 3, making variations only as required to use 2-ethylbutyryl chloride in place of isoxazole-5-carbonyl chloride to react with 6-piperazin-1-yl-pyridazine-3-carboxylic acid (2-cyclopropylethyl)amide, the title compound was obtained as a white solid (71% yield). $^1$H NMR (300 MHz, CDCl$_3$) δ 8.07, 8.00, 7.00, 3.86-3.90, 3.76, 3.68, 3.57, 2.57, 1.70, 1.50-1.55, 0.90, 0.45, 0.10. MS (ES+) m/z 374 (M+1).

EXAMPLE 3.5

6-(4-Cyclohexanecarbonylpiperazin-1-Yl)Pyridazine-3-Carboxylic Acid (2-Cyclopropylethyl) Amide Following the procedure of Example 3, making variations only as required to use cyclohexanecarbonyl chloride in place of isoxazole-5-carbonyl chloride to react with 6-piperazin-1-yl-pyridazine-3-carboxylic acid (2-cyclopropylethyl)-amide, the title compound was obtained as a white solid (58% yield). $^1$H NMR (300 MHz, CDCl$_3$) δ 8.06, 7.99, 6.99, 3.88, 3.79, 3.68, 3.56, 2.50, 1.67-1.84, 1.48-1.60, 1.24-1.34, 0.76, 0.47, 0.10. MS (ES+) m/z 386 (M+1).

EXAMPLE 3.6

6-[4-(2-Trifluoromethoxybenzoyl)Piperazin-1-Yl] Pyridazine-3-Carboxylic Acid (3-Methylbutyl) Amide Following the procedure of Example 3, making variations only as required to use 2-trifluoromethoxybenzoyl chloride in place of isoxazole-5-carbonyl chloride to react with 6-piperazin-1-yl-pyridazine-3-carboxylic acid (3-methylbutyl) amide, the title compound was obtained as a white solid (83% yield). $^1$H NMR (400 MHz, CDCl$_3$) δ 8.06, 7.85, 7.53-7.32, 7.01, 4.12-3.36, 1.75-1.66, 1.54-1.48, 0.98. MS (ES+) m/z 466.2 (M+1).

EXAMPLE 3.7

6-[4-(5-Chloro-2-Trifluoromethylbenzoyl)Piperazin-1-Yl]Pyridazine-3-Carboxylic Acid (3-Methylbutyl) Amide Following the procedure of Example 3, making variations only as required to use 5-chloro-2-trifluoromethylbenzoyl chloride in place of isoxazole-5-carbonyl chloride to react with 6-piperazin-1-yl-pyridazine-3-carboxylic acid (3-methylbutyl)amide, the title compound was obtained as a white solid (80%). m.p. 148-151° C. $^1$H NMR (400 MHz, CDCl$_3$) δ 8.06, 7.85, 7.67, 7.54-7.50, 7.35, 7.01, 4.05-3.34, 1.73-1.46, 0.98. MS (ES+) m/z 484.3 (M+1).

EXAMPLE 3.8

6-[4-(2-Trifluoromethylbenzoyl)Piperazin-1-Yl]Pyridazine-3-Carboxylic Acid (2-Cyclopropylethyl) Amide Following the procedure of Example 3, making variations only as required to use 2-trifluoromethylbenzoyl chloride in place of isoxazole-5-carbonyl chloride to react with 6-piperazin-1-yl-pyridazine-3-carboxylic acid (2-cyclopropylethyl) amide, the title compound was obtained as a white solid (92%). m.p. 95-98° C. $^1$H NMR (300 MHz, CDCl$_3$) δ 8.05, 7.96, 7.74, 7.65-7.52, 7.35, 6.99, 4.08-3.22, 1.55-1.46, 0.80-0.67, 0.48-0.42, 0.10-0.07. $^{13}$C NMR (75 MHz, CDCl$_3$) δ 167.6, 162.9, 160.0, 145.4, 134.2, 132.3, 129.5, 127.2, 127.1, 126.9, 121.8, 118.2, 112.5, 46.3, 44.5, 44.4, 41.2, 39.6, 34.5, 8.6, 4.2. MS (ES+) m/z 448.2 (M+1).

EXAMPLE 3.9

6-[4-(2-CHLORO-5-FLUOROBENZOYL)PIPERAZIN-1-Yl]Pyridazine-3-Carboxylic Acid (2-Cyclopropylethyl)Amide Following the procedure of Example 3, making variations only as required to use 2-chloro-5-fluorobenzoyl chloride in place of isoxazole-5-carbonyl chloride to react with 6-piperazin-1-yl-pyridazine-3-carboxylic acid (2-cyclopropylethyl) amide, the title compound was obtained as a white solid (94% yield). m.p. 194-196° C. $^1$H NMR (300 MHz, CDCl$_3$) δ 8.05, 7.96, 7.41-7.37, 7.11-7.03, 7.00, 4.07-3.34, 1.55-1.46, 0.79-0.68, 0.48-0.42, 0.11-0.06. $^{13}$C NMR (75 MHz, CDCl$_3$) 6165.7, 163.0, 160.0, 159.7, 145.5, 136.7, 131.5, 127.1, 125.3, 117.8, 115.2, 112.5, 46.0, 44.8, 44.6, 41.2, 39.6, 34.5, 8.6, 4.2. MS (ES+) m/z 432.2 (M+1).

EXAMPLE 3.10

6-[4-(3,3,3-TRIFluoro-2-Methyl-2-TRIFLUOROMETHYLPROPIONYL)PIPERAZIN-1-Yl]Pyridazine-3-CARBOXYLIC ACID (2-Cyclopropylethyl)Amide Following the procedure of Example 3, making variations only as required to use (3,3,3-trifluoro-2-methyl-2-trifluoromethylpropionyl chloride in place of isoxazole-5-carbonyl chloride to react with 6-piperazin-1-yl-pyridazine-3-carboxylic acid (2-cyclopropylethyl)amide, the title compound was obtained as a white solid (35% yield). $^1$H NMR (300 MHz, CDCl$_3$) δ 8.02, 7.96, 6.80, 3.91-3.75, 3.58, 1.58-1.48, 0.78-0.63, 0.48-0.43, 0.11-0.04. MS (ES+) m/z 468.2 (M+1).

EXAMPLE 3.11

6-[4-(2,2-DIMETHYLPROPIONYL)PIPERAZIN-1-Yl]Pyridazine-3-CARBOXYLIC ACID (2-Cyclopropylethyl)Amide Following the procedure of Example 3, making variations only as required to use 2,2-dimethylpropionyl chloride in place of isoxazole-5-carbonyl chloride to react with 6-piperazin-1-yl-pyridazine-3-carboxylic acid (2-cyclopropylethyl)amide, the title compound was obtained as a white solid (64% yield). $^1$H NMR (300 MHz, CDCl$_3$) δ 8.05, 8.01, 6.98, 3.86-3.73, 3.57, 1.57-1.48, 0.79-0.70, 0.52-0.45, 0.16-0.12. MS (ES+) m/z 360.0 (M+1).

EXAMPLE 3.12

6-[4-(5-CHLORO-2-Trifluoromethylbenzoyl)Piperazin-1-Yl]Pyridazine-3-CARBOXYLIC AC ID (2-Cyclopropylethyl)Amide Following the procedure of Example 3, making variations only as required to use 5-chloro-2-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white solid (58% yield). m.p. 164-166° C. $^1$H NMR (300 MHz, CDCl$_3$) δ 8.07, 7.96, 7.69, 7.54, 7.02, 4.07-3.35, 1.52, 0.79-0.68, 0.48-0.43, 0.14-0.08. MS (ES+) m/z 482.1 (M+1).

EXAMPLE 3.13

6-[4-(5-Fluoro-2-Trifluoromethylbenzoyl)Piperazin-1-Yl]Pyridazine-3-Carboxylic Acid (2-Cyclopropylethyl)Amide Following the procedure of Example 3, making variations only as required to use 5-fluoro-2-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white powder (65% yield). $^1$H NMR (400 MHz, CDCl$_3$) δ 8.05, 7.98, 7.74, 7.27-7.24, 7.09-7.06, 7.00, 4.08-3.96, 3.94-3.68, 3.55, 3.36, 1.50, 0.79-0.69, 0.48-0.42, 0.11-0.09.

EXAMPLE 3.14

6-[4-(2,6-DIFLUOROBENZOYL)PIPERAZIN-1-Yl]Pyridazine-3-CARBOXYLIC ACID (2-Cyclopropylethyl)Amide Following the procedure of Example 3, making variations only as required to use 2,6-difluorobenzoyl chloride in place of isoxazole-5-carbonyl chloride to react with 6-piperazin-1-yl-pyridazine-3-carboxylic acid (2-cyclopropylethyl)amide, the title compound was obtained as a white powder (44% yield). $^1$H NMR (400 MHz, CDCl$_3$) δ 8.07, 8.07-7.99, 7.44-7.38, 7.02-6.96, 4.0-3.99, 3.86-3.83, 3.58-3.50, 3.39-3.38, 1.52, 1.15-1.10, 0.77-0.74, 0.49-0.45, 0.11-0.08.

EXAMPLE 3.15

6-[4-(PYRROLIDINE-1-CARBONYL)PIPERAZIN-1-Yl]Pyridazine-3-CARBOXYLIC ACID (2-Cyclopropylethyl)Amide Following the procedure of Example 3, making variations only as required to use pyrrolidine-1-carbonyl chloride in place of isoxazole-5-carbonyl chloride to react with 6-piperazin-1-yl-pyridazine-3-carboxylic acid (2-cyclopropylethyl)amide, the title compound was obtained as a white powder (54% yield). $^1$H NMR (400 MHz, CDCl$_3$) δ 8.04, 7.98, 6.99, 3.79, 3.56, 3.47-3.45, 3.40, 1.87-1.85, 1.52, 0.80-0.72, 0.48-0.46, 0.10-0.09.

EXAMPLE 3.16

6-[4-(2,5-BIS-Trifluoromethylbenzoyl)Piperazin-1-Yl]Pyridazine-3-Carboxylic Acid (2-Cyclopropylethyl)Amide Following the procedure of Example 3, making variations only as required to use 2,5-bis-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white powder (50% yield). $^1$H NMR (400 MHz, CDCl$_3$) δ 8.08, 7.99, 7.92-7.9, 7.85-7.84, 7.65, 7.02, 4.13-4.08, 3.95-3.71, 3.57-3.55, 3.38-3.36, 1.57-1.44, 0.8-0.7, 0.48-0.46, 0.16-0.08.

EXAMPLE 3.17

6-[4-(2,4-Bis-Trifluoromethylbenzoyl)Piperazin-1-Yl]Pyridazine-3-Carboxylic Acid (2-Cyclopropylethyl)Amide Following the procedure of Example 3, making variations only as required to use 2,4-bis-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white powder (29% yield). $^1$H NMR (400 MHz, CDCl$_3$) δ 8.08, 8.02-7.98, 7.91, 7.54, 7.03, 3.97-3.86, 3.85-3.72, 3.57, 3.36, 1.52, 0.77-0.74, 0.49-0.46, 0.12-0.09.

EXAMPLE 3.18

6-[4-(2,5-Difluorobenzoyl)Piperazin-1-Yl]Pyridazine-3-Carboxylic Acid (2-Cyclopropylethyl)Amide Following the procedure of Example 3, making variations only as required to use 2,5-difluorobenzoyl chloride in place of isoxazole-5-carbonyl chloride to react with 6-piperazin-1-yl-pyridazine-3-carboxylic acid (2-cyclopropylethyl)-amide, the title compound was obtained as a white powder (53% yield). $^1$H NMR (400 MHz, CDCl$_3$) δ 8.08, 8.0, 7.17-7.11, 7.03, 4.02-3.92, 3.85-3.83, 3.59-3.5, 1.52, 0.74-0.69, 0.46-0.40, 0.09-0.04.

EXAMPLE 3.19

6-[4-(5-Fluoro-2-Trifluoromethylbenzoyl)Piperazin-1-Yl]Pyridazine-3-Carboxylic Acid (3-Cyclopropylpropyl)Amide Following the procedure of Example 3, making variations only as required to use 5-Fluoro-2-trifluoromethylbenzoyl chloride in place of isoxazole-5-carbonyl chloride to react with 6-piperazin-1-yl-pyridazine-3-carboxylic acid (3-cyclopopylpropyl)amide, the title compound was obtained as a white powder (28% yield). $^1$H NMR (400 MHz, CDCl$_3$) δ 8.07, 7.89, 7.76, 7.28-7.24, 7.10-7.08, 7.02, 4.06-4.03, 3.90-3.86, 3.82-3.72, 3.51, 3.37, 1.76-1.70, 1.30, 0.70-0.67, 0.44-0.40, 0.03-0.003.

EXAMPLE 3.20

6-[4-(2-Chloro-4-Trifluoromethylpyrimidine-5-Carbonyl)Piperazin-1-Yl]Pyridazine-3-Carboxylic Acid (2-Cyclopropylethyl)Amide Following the procedure of Example 3, making variations only as required to use 2-chloro-4-trifluoromethylpyrimidine-5-carbonyl chloride in place of isoxazole-5-carbonyl chloride to react with 6-piperazin-1-yl-pyridazine-3-carboxylic acid (2-cyclopropylethyl)amide, the title compound was obtained as a white powder (35% yield). $^1$H NMR (300 MHz, CDCl$_3$) δ 8.77, 8.08, 7.97, 7.01, 4.06-3.68, 3.55, 3.39, 1.50, 0.76-0.71, 0.48-0.42, 0.10-0.05.

EXAMPLE 3.21

6-[4-(2-Fluorobenzoyl)Piperazin-1-Yl]Pyridazine-3-Carboxylic Acid (2-Cyclopropylethyl)Amide Following the procedure of Example 3, making variations only as required to use 2-fluorobenzoyl chloride in place of isoxazole-5-carbonyl chloride to react with 6-piperazin-1-yl-pyridazine-3-carboxylic acid (2-cyclopropylethyl)amide, the title compound was obtained as a white powder (20.3% yield). $^1$H NMR (300 MHz, CDCl$_3$) δ 8.04, 7.98, 7.47-7.40, 7.26-7.21, 7.15-7.09, 6.99, 3.95-3.78, 3.58-3.5, 1.54-1.47, 0.78-0.69, 0.48-0.42, 0.11-0.05.

EXAMPLE 3.22

6-[4-(3-Fluoro-2-Trifluoromethylbenzoyl)Piperazin-1-Yl]Pyridazine-3-Carboxylic Acid (2-Cyclopropylethyl)Amide Following the procedure of Example 3, making variations only as required to use 3-fluoro-2-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white powder (31% yield). $^1$H NMR (300 MHz, CDCl$_3$) δ 8.05, 7.97, 7.65-7.59, 7.29, 7.12, 6.99, 4.05-3.99, 3.89-3.72, 3.54, 3.35, 1.50, 0.76-0.71, 0.48-0.42, 0.10-0.05.

EXAMPLE 3.23

6-[4-(4-Fluoro-2-Trifluoromethylbenzoyl)Piperazin-1-Yl]Pyridazine-3-Carboxylic Acid (3-CYCLOPROPYLPROPYL)AMIDE Following the procedure of Example 3, making variations only as required to use 4-fluoro-2-trifluoromethylbenzoyl chloride in place of isoxazole-5-carbonyl chloride to react with 6-piperazin-1-yl-pyridazine-3-carboxylic acid (3-cyclopropylpropyl)amide, the title compound was obtained as a white powder (49% yield). $^1$H NM R (300 MHz, CDCl$_3$) δ 8.04, 7.87, 7.45-7.3, 6.99, 4.09-3.98, 3.89-3.67, 3.49, 3.33, 1.75-1.66, 1.28, 0.69-0.62, 0.43-0.37, 0.04-0.03.

EXAMPLE 3.24

6-[4-(5-CHLORO-2-Trifluoromethylbenzoyl)Piperazin-1-Yl]Pyridazine-3-Carboxylic Acid (3-CYCLOPROPYLPROPYL)AMIDE Following the procedure of Example 3, making variations only as required to use 5-chloro-2-trifluoromethylbenzoyl chloride in place of isoxazole-5-carbonyl chloride to react with 6-piperazin-1-yl-pyridazine-3-carboxylic acid (3-cyclopropylpropyl)amide, the title compound was obtained as a white solid (73% yield). $^1$H NMR (300 MHz, CDCl$_3$) δ 8.05, 7.86, 7.68-7.65, 7.53-7.5, 7.35, 6.99, 4.05-3.99, 3.89-3.67, 3.52-3.46, 3.37-3.34, 1.75-1.6, 1.31-1.24, 0.71-0.62, 0.43-0.37, 0.02-0.03. $^{13}$C NMR (75 MHz, CDCl$_3$) δ 165.9, 162.9, 159.9, 145.4, 138.8, 135.93, 135.9, 129.7, 128.6, 128.4, 121.4, 112.6, 46.3, 44.5, 44.3, 41.3, 39.2, 31.9, 29.5, 10.5, 4.4. MS (ES+) m/z 496.3 (M+1).

EXAMPLE 3.25

6-[4-(5-Fluoro-2-Trifluoromethylbenzoyl)Piperazin-1-Yl]Pyridazine-3-Carboxylic Acid (4-METHYLPENTYL)AMIDE Following the procedure of Example 3, making variations only as required to use 5-fluoro-2-trifluoromethylbenzoyl chloride in place of isoxazole-5-carbonyl chloride to react with 6-piperazin-1-yl-pyridazine-3-carboxylic acid (4-methylpentyl)amide, the title compound was obtained as a white solid (10% yield). $^1$H NMR (300 MHz, CDCl$_3$) δ 8.04, 7.86, 7.75-7.71, 7.26-7.22, 7.08-7.04, 6.98, 4.10-3.98, 3.90-3.70, 3.46-3.40, 3.36-3.33, 1.61-1.50, 1.28-1.20, 0.85. $^{13}$C NMR (75 MHz, CDCl$_3$) δ 166.0, 162.9, 162.6, 159.9, 145.5, 136.8, 129.7, 127.6, 127.7, 127.2, 125.1, 123.3, 121.4, 116.8, 116.5, 114.9, 114.6, 113.9, 112.5, 46.3, 44.5, 44.3, 41.3, 39.7, 36.0, 27.8, 27.4, 22.5. MS (ES+) m/z 482.4 (M+1).

EXAMPLE 3.26

6-[4-(2-Trifluoromethylbenzoyl)Piperazin-1-Yl]Pyridazine-3-Carboxylic Acid (4-METHYLPENTYL)AMIDE Following the procedure of Example 3, making variations only as required to use 2-trifluoromethylbenzoyl chloride in place of isoxazole-5-carbonyl chloride to react with 6-piperazin-1-yl-pyridazine-3-carboxylic acid (4-methylpentyl) amide, the title compound was obtained as a white solid (65.5% yield). $^1$H NMR (300 MHz, CDCl$_3$) δ 8.03, 7.86, 7.74-7.72, 7.62-7.54, 7.36-7.34, 6.98, 4.08-3.98, 3.92-3.65, 3.47-3.4, 3.35-3.31, 1.62-1.53, 1.28-1.21, 0.86. $^{13}$C NMR (75 MHz, CDCl$_3$) δ167.5, 162.9, 159.9, 145.3, 134.2, 132.3, 129.4, 127.0, 126.7, 126.2, 125.4, 121.7, 112.5, 46.3, 44.5, 44.3, 41.2, 39.6, 35.9, 27.7, 27.4, 22.4. MS (ES+) m/z 464.5 (M+1).

EXAMPLE 3.27

6-[4-(4-Fluoro-2-Trifluoromethylbenzoyl)Piperazin-1-Yl]Pyridazine-3-Carboxylic Acid (2-Cyclopropylethyl)Amide Following the procedure of Example 3, making variations only as required to use 4-fluoro-2-trifluoromethylbenzoyl chloride in place of isoxazole-5-carbonyl chloride to react with 6-piperazin-1-yl-pyridazine-3-carboxylic acid (2-cyclopropylethyl)amide, the title compound was obtained as a white solid (83.5% yield). $^1$H NMR (300 MHz, CDCl$_3$) δ 8.05, 7.97, 7.46-7.42, 7.39-7.29, 6.97, 4.07-4.01, 3.89-3.67, 3.58-3.51, 3.36-3.32, 1.53-147, 0.76-0.69, 0.48-0.42, 0.10-0.06. $^{13}$C NMR (75 MHz, CDCl$_3$) 6166.7, 163.9, 162.8, 160.6, 159.9, 145.4, 129.6, 129.5, 127.0, 119.7, 119.4, 114.8, 114.7, 114.4, 114.38, 112.5, 44.4, 44.5, 44.3, 41.3, 39.6, 34.4, 8.6, 4.1. MS (ES+) m/z 466.1 (M+1).

EXAMPLE 3.28

6-[4-(2-Nitrobenzoyl)Piperazin-1-Yl]Pyridazine-3-Carboxylic Acid (3-Methylbutyl)Amide Following the procedure of Example 3, making variations only as required to use 2-nitrobenzoyl chloride in place of isoxazole-5-carbonyl chloride to react with 6-piperazin-1-yl-pyridazine-3-carboxylic acid (3-methylbutyl)amide, the title compound was obtained as a white solid (72% yield). $^1$H NMR (500 MHz, CDCl$_3$) δ 8.24, 8.07, 7.84, 7.76, 7.63, 7.44, 7.01, 4.12-4.26, 3.75-3.95, 3.50, 3.41, 1.65-1.76, 1.52, 0.94. MS (ES+) m/z 427 (M+1).

EXAMPLE 3.29

6-[4-(2-Chlorobenzoyl)Piperazin-1-Yl]Pyridazine-3-Carboxylic Acid (3-Methylbutyl)Amide Following the procedure of Example 3, making variations only as required to use 2-chlorobenzoyl chloride in place of isoxazole-5-carbonyl chloride to react with 6-piperazin-1-yl-pyridazine-3-carboxylic acid (3-methylbutyl)amide, the title compound was obtained as a white solid (94% yield). $^1$H NMR (500 MHz, CDCl$_3$) δ 8.05, 7.85, 7.43-7.46, 7.31-7.40, 7.00, 4.04-4.10, 3.75-3.94, 3.34-3.52, 1.65-1.75, 1.52, 0.94. MS (ES+) m/z 416 (M+1).

EXAMPLE 3.30

6-[4-(2,4-Dichlorobenzoyl)Piperazin-1-Yl]Pyridazine-3-Carboxylic Acid (3-Methylbutyl)Amide Following the procedure of Example 3, making variations only as required to use 2,4-dichlorobenzoyl chloride in place of isoxazole-5-carbonyl chloride to react with 6-piperazin-1-yl-pyridazine-3-carboxylic acid (3-methylbutyl)amide, the title compound was obtained as a white solid (90% yield). $^1$H NMR (500 MHz, CDCl$_3$) δ 8.07, 7.85, 7.47, 7.35, 7.28, 7.01, 4.02-4.09, 3.75-3.93, 3.33-3.52, 1.65-1.75, 1.52, 0.94. MS (ES+) m/z 450 (M).

EXAMPLE 3.31

Acetic Acid 2-{4-[6-(2-Cyclopropylethylcarbamoyl)Pyridazin-3-Yl]-Piperazine-1-Carbonyl}Phenyl Ester Following the procedure of Example 3, making variations only as required to use acetylsalicyloyl chloride in place of isoxazole-5-carbonyl chloride to react with 6-piperazin-1-yl-pyridazine-3-carboxylic acid (2-cyclopropylethyl)amide, the title compound was obtained as a white solid (39% yield). $^1$H NMR (500 MHz, CDCl$_3$) δ 8.06, 8.00, 7.00, 7.47, 7.34-7.29, 7.18, 6.98, 4.00-3.72, 3.60-3.48, 2.28, 1.52, 0.76, 0.48, 0.10. MS (ES+) m/z 438 (M+1).

EXAMPLE 3.32

6-[4-(5-Chloro-2-Trifluoromethylbenzoyl)Piperazin-1-Yl]Pyridazine-3-Carboxylic Acid (2-Cyclobutylethyl)Amide Following the procedure of Example 3, making variations only as required to use 5-chloro-2-(trifluoromethyl)benzoyl chloride in place of isoxazole-5-carbonyl chloride to react with 6-piperazin-1-ylpyridazine-3-carboxylic acid (2-cyclobutyl-ethyl)amide, the title compound was obtained as a white powder (71% yield). $^1$H NMR (300 MHz, CDCl$_3$) δ 8.07, 7.81, 7.66, 7.51, 7.34, 3.86-3.66, 3.40-3.34, 2.33, 2.03, 1.86-1.57. $^{13}$C NMR (75 MHz, CDCl$_3$) δ 166.0, 162.8, 159.8, 145.5, 138.9, 135.9, 129.8, 128.5, 127.5, 127.3, 125.6, 125.2, 112.7, 46.4, 44.6, 44.5, 41.3, 37.6, 36.5, 33.7, 28.3, 18.6. MS (ES+) m/z 496.5 (M+1).

EXAMPLE 3.33

6-[4-(5-Fluoro-2-Trifluoromethylbenzoyl)Piperazin-1-Yl]Pyridazine-3-Carboxylic Acid (2-Cyclobutylethyl)Amide Following the procedure of Example 3, making variations only as required to use 5-fluoro-2-(trifluoromethyl)benzoyl chloride in place of isoxazole-5-carbonyl chloride to react with 6-piperazin-1-yl-pyridazine-3-carboxylic acid (2-cyclobutylethyl)amide, the title compound was obtained as a white powder (71% yield).
$^1$H NMR (300 MHz, CDCl$_3$) δ 8.03, 7.83-7.71, 7.20, 7.06, 6.95, 4.01, 3.88-3.67, 3.40-3.28, 2.35, 1.89-1.57. $^{13}$C NMR (300 MHz, CDCl$_3$) 6166.0, 162.8, 162.6, 159.9, 145.5, 137.0, 19.7, 127.2, 125.1, 121.5, 116.9, 116.6, 115.0, 114.7, 112.6, 46.4, 44.6, 44.4, 41.3, 37.6, 36.5, 33.7, 28.3, 18.6. MS (ES+) m/z 480.5 (M+1).

EXAMPLE 3.34

6-[4-(5-CHLORO-2-Trifluoromethylbenzoyl)Piperazin-1-Yl]Pyridazine-3-Carboxylic Acid Hexylamide Following the procedure of Example 3, making variations only as required to use 5-chloro-2-(trifluoromethyl)benzyl chloride in place of isoxazole-5-carbonyl chloride to react with 6-piperazin-1-yl-pyridazine-3-carboxylic acid hexylamide, the title compound was obtained as a white powder (55% yield). $^1$H NMR (300 MHz, CDCl$_3$) δ 8.07, 7.86, 7.66, 7.51, 7.34, 7.00, 4.00, 3.88-3.66, 3.47-3.33, 1.62-1.53, 1.38-1.27, 0.85. $^{13}$C NMR (75 MHz, CDCl$_3$) δ 166.0, 162.9, 159.9, 145.5, 138.9, 135.9, 129.8, 128.5, 127.5, 127.2, 125.6, 125.1, 121.5, 112.7, 46.4, 44.6, 41.3, 39.5, 31.5, 29.5, 26.6, 22.6, 14.0. MS (ES+) m/z 498.2 (M+1).

EXAMPLE 3.35

6-[4-(5-Fluoro-2-Trifluoromethylbenzoyl)-[1,4]Diazepan-1-Yl]Pyridazine-3-Carboxylic Acid (2-Cyclopropylethyl)Amide Following the procedure of Example 3, making variations only as required to use 5-fluoro-2-trifluoromethylbenzoyl chloride in place of isoxazole-5-carbonyl chloride to react with 6-[1,4]diazepan-1-ylpyridazine-3-carboxylic acid (2-cyclopropylethyl)amide, the title compound was obtained as a white solid (60% yield).

$^1$H NMR (CDCl$_3$, 300 MHz) δ 8.07-7.85, 7.71-7.6, 7.23-7.08, 6.94-6.88, 6.34-6.31, 4.24-4.12, 3.98-3.73, 3.67-3.36, 3.29-3.25, 2.19-1.73, 1.53-1.46, 0.81-0.68, 0.48-0.4, 0.11 0.03. $^{13}$C NMR (CDCl$_3$, 75 MHz) δ 167.3, 167.2, 165.7, 163.1, 162.9, 162.3, 158.9, 158.4, 144.8, 144.6, 137.1, 129.7-129.2, 127.4, 127.2, 125.0, 121.4, 116.7, 116.6, 116.4, 116.3, 114.9, 114.8, 114.6, 114.5, 111.5, 111.3, 48.8, 48.6, 47.6, 47.5, 45.8, 45.7, 44.1, 39.6, 34.5, 26.8, 25.4, 8.6, 4.2. MS (ES+) m/z 480.1 (M+1).

EXAMPLE 4

Synthesis of 6-(4-Benzylpiperazin-1-YL)Pyridazine-3-Carboxylic Acid (3-Methylbutyl)Amide A stirred mixture of 6-chloropyridazine-3-carboxylic acid (3-methylbutyl)amide (0.113 g, 0.5 mmol), 1-benzylpiperazine (90 mg, 0.5 mmol), tetrabutylammonium bromide (27 mg, 0.084 mmol) and 1,8-diazabicylco[5.4.0]undec-7-ene (152 mg, 1.0 mmol) was heated under reflux in dioxane (10 mL) overnight. The solvent was evaporated. Residue was treated with 2% methanol in water (25 mL). The solid, which precipitated, was filtered off and dried in vacuo to give 138 mg (0.376 mmol) of the title compound in 75% yield. $^1$H NMR (300 MHz, CDCl$_3$) δ 7.98, 7.87, 7.36-7.32, 6.94, 3.76-3.74, 3.57, 3.50-3.46, 2.60-2.58, 1.74-1.68, 1.52-1.48, 0.94. MS (ES+) m/z 368.2 (M+1).

EXAMPLE 5

Synthesis of 1-(2-Phenylcyclopropyl)-3-{6-[4-(2-Trifluoromethylbenzoyl)Piperazin-1-Yl]Pyridazin-3-Yl}Urea To a solution of [4-(6-aminopyridazin-3-yl)piperazin-1-yl](2-trifluoromethyl-phenyl)methanone (123 mg, 0.35 mmol) in DMF (20.0 mL) was added (2-isocyanatocyclopropyl)benzene (111 mg, 0.7 mmol). The mixture was stirred at 60° C. overnight. After cooling, the mixture was poured into water (120 mL). The white solid, which precipitated, was filtered off and dried in vacuum to give the title product (162 mg) as a white solid in 90% yield. $^1$H NMR (300 MHz, CDCl$_3$) δ 8.01-7.97, 7.73, 7.60, 7.55, 7.32, 7.22-7.10, 7.06, 4.00-3.95, 3.87-3.86, 3.62-3.52, 3.43-3.41, 3.25-3.22, 2.85-2.82, 2.14-2.10, 0.91-0.86. MS (ES+) m/z 511.2 (M+1).

EXAMPLE 5.1

3-(3-{6-[4-(2-Trifluoromethylbenzoyl)Piperazin-1-Yl]-Pyridazin-3-Yl}-Ureido)Propionic Acid Ethyl Ester Following the procedure of Example 5, making variations only as required to use 3-isocyanatopropionic acid ethyl ester in place of (2-isocyanatocyclopropyl)benzene to react with [4-(6-aminopyridazin-3-yl)piperazin-1-yl](2-trifluoromethylphenyl)methanone, the title compound was obtained as a white powder (37% yield). $^1$H NMR (300 MHz, CDCl$_3$) δ 8.12, 7.92, 7.74, 7.62, 7.55, 7.36, 7.11, 6.65, 3.95-3.90, 3.59, 3.49-3.40, 3.28, 2.36-2.33; 1.63-1.61, 0.94-0.93.

EXAMPLE 5.2

1-Pentyl-3-{6-[4-(2-Trifluoromethylbenzoyl)Piperazin-1-Yl]Pyridazin-3-Yl}Urea Following the procedure of Example 5, making variations only as required to use pentylisocyanate in place of (2-isocyanatocyclopropyl)benzene to react with [4-(6-aminopyridazin-3-yl)piperazin-1-yl](2-trifluoromethylphenyl)methanone, the title compound was obtained as a white solid (45.5% yield). $^1$H NMR (400 MHz, CDCl$_3$) δ 10.60, 7.82, 7.74, 7.13, 7.63, 7.56, 7.52, 7.36, 7.08, 4.29, 4.0-4.09, 3.85-3.95, 3.50-3.70, 3.40-3.47, 3.25-3.36, 1.50-1.60, 1.22-1.36, 0.80-0.92. MS (ES+) m/z 465 (M+1).

EXAMPLE 5.3

1-Benzyl-3-{6-[4-(2-Trifluoromethylbenzoyl)Piperazin-1-Yl]Pyridazin-3-Yl}Urea Following the procedure of Example 5, making variations only as required to use benzylisocyanate in place of (2-isocyanatocyclopropyl)benzene to react with [4-(6-aminopyridazin-3-yl)piperazin-1-yl](2-trifluoromethylphenyl)methanone, the title compound was obtained as a white solid (45.6% yield). $^1$H NMR (500 MHz, CDCl$_3$) δ 12.0, 8.28, 7.80, 7.67, 7.62, 7.32, 7.23, 7.02-7.14, 4.54, 3.85-3.91, 3.69-3.76, 3.28-3.40, 2.94-3.10.

EXAMPLE 5.4

1-(4-Fluorophenyl)-3-{6-[4-(2-Trifluoromethylbenzoyl)Piperazin-1-Yl]-Pyridazin-3-Yl}Urea Following the procedure of Example 5, making variations only as required to use 4-fluorophenylisocyanate in place of (2-isocyanatocyclopropyl)benzene to react with [4-(6-aminopyridazin-3-yl)piperazin-1-yl](2-trifluoromethylphenyl)-methanone, the title compound was obtained as a white solid (32.3% yield). $^1$H NMR (500 MHz, CDCl$_3$) δ 12.0, 8.20, 7.53, 7.64, 7.59, 7.39, 7.33, 7.16, 6.91-6.98, 3.96-4.04, 3.83-3.90, 3.52-3.65, 3.37-3.45, 3.20-3.26. MS (ES+) m/z 489 (M+1).

EXAMPLE 5.5

1-(2-Fluorophenyl)-3-{6-[4-(2-Trifluoromethylbenzoyl)Piperazin-1-Yl]-Pyridazin-3-Yl}Urea Following the procedure of Example 5, making variations only as required to use 2-flurophenylisocyanate in place of (2-isocyanatocyclopropyl)benzene to react with [4-(6-aminopyridazin-3-yl)piperazin-1-yl](2-trifluoromethylphenyl)-methanone, the title compound was obtained as a white solid (32% yield). $^1$H NMR (500 MHz, CDCl$_3$) δ 7.90-8.30, 7.99, 7.75, 7.63, 7.57, 7.34, 7.10-7.17, 7.01-7.07, 3.94-4.01, 3.85-3.92, 3.56-3.66, 3.41-3.49, 3.24-3.29.

EXAMPLE 5.6

1-PHENETHYL-3-{6-[4-(2-TRIFLUOROMETHYLBENZOYL)-PIPERAZIN-1-Yl]-Pyridazin-3-Yl}Urea Following the procedure of Example 5, making variations only as required to use 2-phenylethylisocyanate in place of (2-isocyanatocyclopropyl)benzene to react with [4-(6-aminopyridazin-3-yl)piperazin-1-yl](2-trifluoromethylphenyl)-methanone, the title compound was obtained as a white solid (19% yield). $^1$H NMR (500 MHz, CDCl$_3$) δ 7.92, 7.60, 7.64, 7.58, 7.37, 7.13-7.24, 7.09, 3.96-4.03, 3.82-3.89, 3.40-3.56, 3.22-3.34, 2.86.

EXAMPLE 5.7

1-(4-FLUOROBENZYL)-3-{6-[4-(2-Trifluoromethylbenzoyl)Piperazin-1-Yl]-Pyridazin-3-Yl}Urea Following the procedure of Example 5, making variations only as required to use 4-fluorobezylisocyanate in place of (2-isocyanatocyclopropyl)benzene to react with [4-(6-aminopyridazin-3-yl)piperazin-1-yl](2-trifluoromethylphenyl)-methanone, the title compound was obtained as a white solid (56% yield). $^1$H NMR (500 MHz, CDCl$_3$) δ 8.13, 7.78, 7.66, 7.60, 7.33, 7.21, 7.09, 6.83, 4.50, 3.91-4.00, 3.73-3.80, 3.34-3.48, 3.05-3.22. MS (ES+) m/z 503 (M+1).

EXAMPLE 5.8

1-BUTYL-3-{6-[4-(2-Trifluoromethylbenzoyl)Piperazin-1-Yl]Pyridazin-3-Yl}Urea

Following the procedure of Example 5, making variations only as required to use butylisocyanate in place of (2-isocyanatocyclopropyl)benzene to react with [4-(6-aminopyridazin-3-yl)piperazin-1-yl](2-trifluoromethylphenyl) methanone, the title compound was obtained as a white solid (92% yield). $^1$H NMR (500 MHz, CDCl$_3$) δ 7.84, 7.74, 7.63, 7.56, 7.36, 7.08, 4.00-4.07, 3.88-3.94, 3.54-3.66, 3.42-3.46, 3.27-3.36, 1.51-1.57, 1.30-1.40, 0.89. MS (ES+) m/z 451 (M+1).

EXAMPLE 5.9

1-Cyclopentyl-3-{6-[4-(2-Trifluoromethylbenzoyl)-Piperazin-1-Yl]Pyridazin-3-Yl}Urea Following the procedure of Example 5, making variations only as required to use cyclopentylisocyanate in place of (2-isocyanatocyclopropyl)benzene to react with [4-(6-aminopyridazin-3-yl)piperazin-1-yl](2-trifluoromethylphenyl)-methanone, the title compound was obtained as a white solid (91% yield). $^1$H NMR (500 MHz, DMSO-d$_6$) δ 9.02, 7.82, 7.75, 7.65, 7.58, 7.51, 7.34, 3.91-3.98, 3.67-3.80, 3.46-3.58, 3.36-3.44, 3.11-3.35, 1.80-1.88, 1.46-1.67, 1.30-1.40. MS (ES+) m/z 451 (M+1).

EXAMPLE 5.10

1-Hexyl-3-{6-[4-(2-Trifluoromethylbenzoyl)Piperazin-1-Yl]Pyridazin-3-Yl}Urea

Following the procedure of Example 5, making variations only as required to use hexylisocyanate in place of (2-isocyanatocyclopropyl)benzene to react with [4-(6-aminopyridazin-3-yl)piperazin-1-yl](2-trifluoromethylphenyl) methanone, the title compound was obtained as a white powder (50% yield). $^1$H NMR (300 MHz, CD$_3$OD) δ 7.83, 7.76, 7.69, 7.52, 7.44, 7.39, 3.87-4.00, 3.66, 3.50, 3.25-3.43, 1.53-1.67, 1.28-1.48, 0.84-0.98. MS (ES+) m/z 479 (M+1).

EXAMPLE 5.11

1-Heptyl-3-{6-[4-(2-Trifluoromethylbenzoyl)Piperazin-1-Yl]Pyridazin-3-Yl}Urea

Following the procedure of Example 5, making variations only as required to use heptylisocyanate in place of (2-isocyanatocyclopropyl)benzene to react with [4-(6-aminopyridazin-3-yl)piperazin-1-yl](2-trifluoromethylphenyl) methanone, the title compound was obtained as white powder (46% yield). $^1$H NMR (300 MHz, DMSO-d$_6$) δ 9.12, 7.82, 7.75, 7.65, 7.50-7.57, 7.35, 3.69-3.80, 3.45-3.60, 3.38-3.43, 3.28-3.34, 3.20-3.26, 3.06-3.17, 1.45, 1.15-1.28, 0.85.

EXAMPLE 5.12

1-(3,4-Dichlorobenzyl)-3-{6-[4-(2-Trifluoromethylbenzoyl)Piperazin-1-Yl]-Pyridazin-3-Yl}Urea Following the procedure of Example 5, making variations only as required to use 3,4-dichlorobenzylisocyanate in place of (2-isocyanato-cyclopropyl)benzene to react with [4-(6-aminopyridazin-3-yl)piperazin-1-yl](2-trifluoromethylphenyl)-methanone, the title compound was obtained as white powder (44% yield). $^1$H NMR (300 MHz, DMSO-d$_6$) δ 9.38, 8.30, 7.85, 7.77, 7.67, 7.59, 7.52-7.57, 7.39, 7.29, 4.38, 3.70-3.82, 3.50-3.62, 3.42-3.47, 3.34-3.38, 3.23-3.29, 3.15-3.20. MS (ES+) m/z 553 (M+1).

EXAMPLE 5.13

1-Cyclohexyl-3-{6-[4-(2-Trifluoromethylbenzoyl)Piperazin-1-Yl]-Pyridazin-3-Yl}Urea Following the procedure of Example 5, making variations only as required to use cyclohexylisocyanate in place of (2-isocyanatocyclopropyl)benzene to react with [4-(6-aminopyridazin-3-yl)piperazin-1-yl](2-trifluoromethylphenyl)-methanone, the title compound was obtained as white powder (34% yield). $^1$H NMR (300 MHz, DMSO-d$_6$) δ 9.05, 7.82, 7.74, 7.65, 7.55, 7.52, 7.35, 3.69-3.79, 3.44-3.58, 3.35-3.42, 3.20-3.26, 3.11-3.18, 1.75-1.84, 1.58-1.67, 1.47-1.55, 1.10-1.35.

EXAMPLE 6

Synthesis of 2-Phenoxy-N-{6-[4-(2-Trifluoromethylbenzoyl)Piperazin-1-Yl]Pyridazin-3-Yl}Acetamide To a stirred solution of [4-(6-aminopyridazin-3-yl)-piperazin-1-yl]-(2-trifluoromethyl-phenyl)methanone (105 mg, 0.300 mmol) in dichloromethane (10 mL) was added phenoxyacetyl chloride (56 mg, 0.32 mmol) followed by the addition of triethylamine (0.15 mL) at 0° C. The mixture was stirred at ambient temperature overnight. Water was added and the mixture was extracted with ethyl acetate (2×15 mL). The combined organic layer was washed sequentially with diluted HCl, sodium bicarbonate and brine solution, then dried with Na$_2$SO$_4$, concentrated. The residue was re-dissolved in small amount of dichloromethane and purified by column chromatography. The title compound was isolated as a white solid in 34% yield (50 mg). $^1$H NMR (300 MHz, CDCl$_3$) δ 9.28, 8.38, 7.75, 7.64, 7.56, 7.35, 7.04, 4.65, 4.01, 3.68, 3.34.

EXAMPLE 6.1

2-Phenylcyclopropanecarboxylic Acid (2-Phenylcyclopropanecarbonyl){6-[4-(2-Trifluoromethylbenzoyl)Piperazin-1-Yl]Pyridazin-3-Yl}Amide and 2-Phenylcyclopropanecarboxylic Acid {6-[4-(2-Trifluoromethylbenzoyl)Piperazin-1-Yl]Pyridazin-3-Yl}Amide Following the procedure of Example 6, making variations only as required to use 2-phenylcyclopropanecarbonyl chloride in place of phenoxyacetyl chloride to react with [4-(6-aminopyridazin-3-yl)piperazin-1-yl](2-trifluoromethylphenyl)-methanone, both compounds were obtained from the reaction. 2-Phenylcyclopropanecarboxylic acid (2-phenylcyclopropanecarbonyl){6-[4-(2-trifluoromethylbenzoyl)piperazin-1-yl]pyridazin-3-yl}amide was isolated by column chromatography eluting with EtOAc:hexane=40:60 and obtained as a white powder (20% yield). $^1$H NMR (300 MHz, CDCl$_3$) δ 7.73, 7.62, 7.54, 7.34, 7.22, 7.16, 7.04, 6.84, 3.99, 3.82, 3.63, 3.28, 2.62, 2.31, 1.76, 1.38. MS (ES+) m/z 640.3 (M+1). 2-Phenylcyclopropanecarboxylic acid {6-[4-(2-trifluoromethyl-benzoyl)piperazin-1-yl]pyridazin-3-yl}amide was isolated by column chromatography eluting with EtOAc: hexane=50:50 and obtained as a white powder (16% yield). $^1$H NMR (300 MHz, CDCl$_3$) δ 10.36, 8.39, 7.76, 7.64, 7.57, 7.34, 7.18, 7.12, 3.92, 3.52, 3.37, 3.18, 2.64, 2.30, 1.34. MS (ES+) m/z 496.3 (M+1).

EXAMPLE 6.2

Hexanoic Acid {6-[4-(2-Trifluoromethylbenzoyl)Piperazin-1-Yl]Pyridazin-3-Yl}AMIDE Following the procedure of Example 6, making variations only as required to use hexanoyl chloride in place of phenoxyacetyl chloride to react with [4-(6-aminopyridazin-3-yl)piperazin-1-yl](2-trifluoromethylphenyl)methanone, the title compound was obtained as a white solid (30% yield). $^1$H NMR (300 MHz, CDCl$_3$) δ 11.65, 8.62, 7.75, 7.65, 7.58, 7.46-7.53, 7.37, 4.08, 3.88, 3.52-3.78, 3.30-3.40, 2.63, 1.72-1.79, 1.24-1.40, 0.90. MS (ES+) m/z 449.7 (M+1).

EXAMPLE 6.3

4-Fluoro-N-{6-[4-(2-Trifluoromethylbenzoyl)Piperazin-1-Yl]-Pyridazin-3-Yl}Benzamide Following the procedure of Example 6, making variations only as required to use 4-fluorobenzoyl chloride in place of phenoxyacetyl chloride to react with [4-(6-aminopyridazin-3-yl)piperazin-1-yl](2-trifluoromethylphenyl)methanone, the title compound was obtained as a light yellow solid (62% yield). $^1$H NMR (400 MHz, DMSO-d$_6$) δ 7.78-7.85, 7.77, 7.66, 7.52, 7.44, 7.25-7.35, 3.10-3.80.

EXAMPLE 7

Synthesis of {6-[4-(2-Trifluoromethylbenzoyl)Piperazin-1-Yl]Pyridazin-3-Yl}Carbamic Acid Butyl Ester To a stirred solution of [4-(6-aminopyridazin-3-yl)piperazin-1-yl](2-trifluoromethyl-phenyl)methanone (100 mg, 0.285 mmol) in dichloromethane (5 mL) was added n-butyl chloroformate (0.285 mmol) in the presence of triethylamine (0.313 mmol) at 0° C. The resulting mixture was stirred at ambient temperature for 24 h and then quenched with water (10 mL). The organic phase was washed with water, saturated NaCl, dried over MgSO$_4$ and then concentrated in vacuo to afford the desired product as a white solid (0.095 g, 74% yield). $^1$H NMR (500 MHz, CDCl$_3$) δ 8.10, 7.73, 7.63, 7.55, 7.36, 7.04, 4.19, 3.96-4.02, 3.89-3.95, 3.61-3.66, 3.52-3.56, 3.32, 1.64-1.70, 1.38-1.46, 0.95.

EXAMPLE 7.1

{6-[4-(2-Trifluoromethylbenzoyl)Piperazin-1-Yl] Pyridazin-3-Yl}Carbamic Acid Propyl Ester Following the procedure of Example 7, making variations only as required to use propyl chloroformate in place of n-butyl chloroformate to react with [4-(6-aminopyridazin-3-yl)piperazin-1-yl](2-trifluoromethylphenyl)methanone, the title compound was obtained as a white solid (72% yield). $^1$H NMR (500 MHz, CDCl$_3$) δ 8.10, 7.73, 7.62, 7.55, 7.37, 7.04, 4.14, 3.96-4.02, 3.88-3.94, 3.61-3.66, 3.52-3.56, 3.32, 1.66-1.75, 0.98. MS (ES+) m/z 438 (M+1).

EXAMPLE 7.2

{6-[4-(2-Trifluoromethylbenzoyl)Piperazin-1-Yl] Pyridazin-3-Yl}Carbamic Acid Isobutyl Ester Following the procedure of Example 7, making variations only as required to use 2-methylpropyl chloroformate in place of n-butyl chloroformate to react with [4-(6-aminopyridazin-3-yl)piperazin-1-yl](2-trifluoromethylphenyl) methanone, the title compound was obtained as a white solid (47% yield). $^1$H NMR (500 MHz, CDCl$_3$) δ 8.09, 7.73, 7.65, 7.63, 7.55, 7.36, 7.04, 3.96, 3.95-4.02, 3.88-3.94, 3.61-3.65, 3.52-3.56, 3.32, 1.94-2.04, 0.96. MS (ES+) m/z 452 (M+1).

EXAMPLE 7.3

{6-[4-(2-Trifluoromethylbenzoyl)Piperazin-1-Yl] Pyridazin-3-Yl}Carbamic Acid Ethyl Ester Following the procedure of Example 7, making variations only as required to use ethyl chloroformate in place of n-butyl chloroformate to react with [4-(6-aminopyridazin-3-yl)piperazin-1-yl](2-trifluoromethylphenyl)methanone, the title compound was obtained as a light yellow solid (35% yield). $^1$H NMR (300 MHz, DMSO-d$_6$) δ 10.30, 7.82-7.85, 7.76, 7.67, 7.52, 7.37, 4.15, 3.15-3.85, 1.10. MS (ES+) m/z 424 (M+1).

EXAMPLE 8

Synthesis of 1-(3-Cyclopropylpropyl)-3-{6-[4-(2-Trifluoromethylbenzoyl)Piperazin-1-Yl]Pyridazin-3-Yl}Urea

[4-(6-Aminopyridazin-3-yl)piperazin-1-yl](2-trifluoromethylphenyl)methanone (200 mg, 0.57 mmol) was slowly added to an ice cold solution of 1,1'-carbonyldiimidazole (110 mg, 0.683 mmol) in anhydrous dichloromethane (15 mL). The temperature was then raised to ambient temperature and the reaction mixture was stirred for another 4 hours. 3-Cyclopropylpropylamine (48.5 mg, 0.569 mmol) was then added to the reaction mixture which was stirred at ambient temperature overnight under nitrogen. The reaction mixture was washed by saturated sodium bicarbonate and brine solution, concentrated and purified by flash column chromatography to yield the product as a white solid (23 mg, 8.5% yield). $^1$H NMR (300 MHz, CDCl$_3$) δ 10.2, 7.68-7.83, 7.72, 7.65, 7.63, 7.55, 7.36, 7.04, 3.95-4.02, 3.83-3.95, 3.50-3.68, 3.40-3.50, 3.26-3.38, 1.60-1.72, 1.17-1.30, 0.71-0.80, 0.44-0.50, −0.06-0.013. MS (ES+) m/z 477 (M+1).

EXAMPLE 8.1

1-{6-[4-(2,6-Difluorobenzoyl)Piperazin-1-Yl]Pyridazin-3-Yl}-3-(3-M Ethylbutyl)Urea Following the procedure of Example 8, making variations only as required to use 3-methylbutylamine in place of 3-cyclopropylpropylamine to react with [4-(6-aminopyridazin-3-yl)piperazin-1-yl](2,5-difluorophenyl)methanone, the title compound was obtained as a white solid (27% yield). $^1$H NMR (300 MHz, CDCl$_3$) δ 9.75, 7.68, 7.32-7.43, 7.07, 6.89-7.00, 3.85-4.00, 3.25-3.75, 1.40-1.65, 0.89. MS (ES+) m/z 432.8 (M+1).

EXAMPLE 8.2

1-Cyclopropylmethyl-3-{6-[4-(2-Trifluoromethylbenzoyl)Piperazin-1-Yl]Pyridazin-3-Yl}Urea Following the procedure of Example 8, making variations only as required to use cyclopropylmethylamine in place of 3-cyclopropylpropylamine to react with [4-(6-aminopyridazin-3-yl)piperazin-1-yl](2-trifluoromethylphenyl)methanone, the title compound was obtained as a white solid (50% yield). $^1$H NMR (400 MHz, CDCl$_3$) δ 7.80-7.54, 7.37, 7.09, 4.07-3.18, 1.12-0.98, 0.52-0.46, 0.27-0.22. MS (ES+) m/z 449.9 (M+1).

EXAMPLE 8.3

1-(3,3-Dimethylbutyl)-3-{6-[4-(2-Trifluoromethylbenzoyl)Piperazin-1-Yl]Pyridazin-3-Yl}Urea Following the procedure of Example 8, making variations only as required to use 3,3-dimethylbutylamine in place of 3-cyclopropylpropylamine to react with [4-(6-aminopyridazin-3-yl)piperazin-1-yl](2-trifluoromethylphenyl)methanone, the title compound was obtained as a white solid (56% yield). $^1$H NMR (400 MHz, CDCl$_3$) δ 8.04-7.54, 7.37, 7.09, 4.08-3.16, 1.52-1.44, 0.88. MS (ES+) m/z 479.3 (M+1).

EXAMPLE 8.4

1-(2-Cyclopropylethyl)-3-{6-[4-(2-Trifluoromethylbenzoyl)Piperazin-1-Yl]Pyridazin-3-Yl}Urea Following the procedure of Example 8, making variations only as required to use 2-cyclopropylethylamine in place of 3-cyclopropylpropylamine to react with [4-(6-aminopyridazin-3-yl)piperazin-1-yl](2-trifluoromethylphenyl)methanone, the title compound was obtained as a yellow solid (65% yield). m.p. >300° C. $^1$H NMR (300 MHz, CDCl$_3$) δ 7.73, 7.62, 7.55, 7.36, 7.07, 4.04-7.00, 3.94-3.89, 3.64-3.56, 3.47-3.45, 3.40-3.32, 1.46, 0.69-0.66, 0.47-0.38, 0.06-0.00. MS (ES+) m/z 463 (M+1).

EXAMPLE 8.5

1-(2-Isopropoxyethyl)-3-{6-[4-(2-Trifluoromethylbenzoyl)Piperazin-1-Yl]Pyridazin-3-Yl}Urea Following the procedure of Example 8, making variations only as required to use 2-isopropoxyethylamine in place of 3-cyclopropylpropylamine to react with [4-(6-aminopyridazin-3-yl)piperazin-1-yl](2-trifluoromethylphenyl)methanone, the title compound was obtained as a yellow solid (15% yield). m.p. >300° C. $^1$H NMR (300 MHz, CDCl$_3$) δ 7.69, 7.60-7.56, 7.51, 7.35, 3.98-3.92, 3.74-3.64, 3.45-3.44, 3.38-3.19, 3.09-2.97, 2.95-2.86, 2.84-2.77, 2.00-1.74, 1.77-1.74, 1.38. MS (ES+) m/z 470 (M+1).

EXAMPLE 8.6

1-(3-Hydroxy-4,4-Dimethylpentyl)-3-{6-[4-(2-Trifluoromethylbenzoyl)-1-Yl]Pyridazin-3-Yl}Urea Following the procedure of Example 8, making variations only as required to use 3-hydroxy-4,4-dimethylpentylamine in place of 3-cyclopropylpropylamine to react with [4-(6-aminopyridazin-3-yl)piperazin-1-yl](2-trifluoromethylphenyl)-methanone, the title compound was obtained as a yellow solid (32% yield). m.p. 218-221° C. MS (ES+) m/z 470 (M+1).

EXAMPLE 8.7

1-(2-Cyclopropylethyl)-3-{6-[4-(2-Fluoro-6-Trifluoromethylbenzoyl)-Piperazin-1-Yl]Pyridazin-3-Yl}Urea Following the procedure of Example 8, making variations only as required to use 2-cyclopropylethylamine in place of 3-cyclopropylpropylamine to react with [4-(6-aminopyridazin-3-yl)piperazin-1-yl](2-fluoro-6-trifluoromethylphenyl)-methanone, the title compound was obtained as a white powder (48% yield). $^1$H NMR (400 MHz, CDCl$_3$) δ 8.14, 7.58-7.54, 7.43, 7.38-7.34, 7.10-7.05, 4.01-3.94, 3.58-3.32, 1.46, 0.72-0.67, 0.45-0.39, 0.08-0.02.

EXAMPLE 8.8

1-(2-Cyclopropylethyl)-3-{6-[4-(5-Fluoro-2-Trifluoromethylbenzoyl)-Piperazin-1-Yl]Pyridazin-3-Yl}Urea Following the procedure of Example 8, making variations only as required to use 2-cyclopropylethylamine in place of 3-cyclopropylpropylamine to react with [4-(6-aminopyridazin-3-yl)piperazin-1-yl](5-fluoro-2-trifluoromethylphenyl)-methanone, the title compound was obtained as a white powder (30% yield). $^1$H NMR (400 MHz, CDCl$_3$) δ 8.30, 7.76-7.71, 7.23, 7.10-7.06, 4.00-3.97, 3.91-3.87, 3.65-3.45, 3.88-3.40, 1.26-1.24, 0.74-0.68, 0.44-0.43, 0.05-0.04.

EXAMPLE 8.9

1-(2-Cyclopropylethyl)-3-{6-[4-(2,6-Difluorobenzoyl)Piperazin-1-Yl]-Pyridazin-3-Yl}Urea Following the procedure of Example 8, making variations only as required to use 2-cyclopropylethylamine in place of 3-cyclopropylpropylamine to react with [4-(6-aminopyridazin-3-yl)piperazin-1-yl](2,6-difluorophenyl)methanone, the title compound was obtained as a white powder (14.1% yield). $^1$H NMR (400 MHz, CDCl$_3$) δ 9.16, 7.89, 7.62-7.52, 7.37, 7.26-7.21, 3.81-3.78, 3.58-3.52, 3.44-3.37, 3.32-3.28, 3.24-3.18, 1.36, 0.70-0.65, 0.42-0.37, 0.07-0.03.

EXAMPLE 8.10

1-(3-Cyclopropylpropyl)-3-{6-[4-(5-Fluoro-2-Trifluoromethylbenzoyl)-Piperazin-1-Yl]Pyridazin-3-Yl}Urea Following the procedure of Example 8, making variations only as required to use [4-(6-aminopyridazin-3-yl)piperazin-1-yl](2-trifluoromethylphenyl)methanone in place of [4-(6-aminopyridazin-3-yl)piperazin-1-yl](5-fluoro-2-trifluoromethylphenyl)methanone to react with 3-cyclopropylpropylamine, the title compound was obtained as a white powder (15% yield). $^1$H NMR (400 MHz, CDCl$_3$) δ 8.32-8.31, 7.76-7.73, 7.76-7.73, 7.25-7.22, 7.13-7.06, 4.14-3.98, 3.95-3.85, 3.68-3.52, 3.40-3.32, 1.70-1.60, 1.28-1.21, 0.65-0.62, 0.40-0.36, 0.03-0.02.

EXAMPLE 8.11.

1-(4-Methylpentyl)-3-{6-[4-(2-Trifluoromethylbenzoyl)Piperazin-1-Yl]Pyridazin-3-Yl}Urea Following the procedure of Example 8, making variations only as required to use 4-methylpentylamine in place of 3-cyclopropylpropylamine to react with [4-(6-aminopyridazin-3-yl)piperazin-1-yl](2-trifluoromethylphenyl)methanone, the title compound was obtained as a white solid (0.039 g, 29% yield). $^1$H NMR (300 MHz, CDCl$_3$) δ 10.7-10.2, 7.85-7.77, 7.73, 7.65-7.5, 7.35, 7.1-7.07, 4.08-3.95, 3.94-3.83, 3.64-3.52, 3.48-3.38, 3.35-3.21, 1.6-1.45, 1.25-1.12, 0.83. $^{13}$C NMR (75 MHz, CDCl$_3$) δ 167.5, 156.8, 155.8, 151.7, 134.4, 132.3, 129.4, 127.2, 126.8, 126.7, 125.4, 121.8, 121.3, 118.4, 46.4, 46.02, 45.8, 40.3, 36.1, 28.3, 27.8, 22.5. MS (ES+) m/z 479.4 (M+1).

EXAMPLE 9

Synthesis of 6-[4-(2,5-Dichlorobenzoyl)Piperazin-1-Yl]Pyridazine-3-Carboxylic Acid (3-Methylbutyl)Amide A mixture of 6-piperazin-1-yl-pyridazine-3-carboxylic acid (3-methylbutyl)amide (0.255 mmol), 2,5-dichlorobenzoic acid (0.31 mmol), 1,8-diazabicylco[5.4.0]undec-7-ene (0.51 mmol) and 1-hydroxybenozotriazole hydrate (0.31 mmol) in DMF (2 mL) was stirred at ambient temperature for 15 min. 1-(3-Dimethylaminopropyl)-3-ethylcarbodiimide (0.31 mmol) was then added. The mixture was stirred at ambient temperature overnight, and then diluted with EtOAc (50 mL) and washed with aqueous saturated NaHCO$_3$ (2×20 mL) and brine (2×20 mL). The organic extract was dried over anhydrous Na$_2$SO$_4$, concentrated, and purified by flash chromatography to give the title compound as a white solid (102 mg, 89% yield). $^1$H NMR (500 MHz, CDCl$_3$) δ 8.07, 7.85, 7.32-7.40, 7.01, 4.01-4.08, 3.77-3.93, 3.35-3.55, 1.65-1.75, 1.52, 0.94. MS (ES+) m/z 450 (M+1).

EXAMPLE 9.1

6-[4-(5-Methyl-2-Trifluoromethylfuran-3-Carbonyl)Piperazin-1-Yl]Pyridazine-3-Carboxylic Acid (2-Cyclopropylethyl)Amide Following the procedure of Example 9, making variations only as required to use 5-methyl-2-trifluoromethylfuran-3-carboxylic acid in place of 2,5-dichlorobenzoic acid to react with 6-piperazin-1-yl-pyridazine-3-carboxylic acid (2-cyclopropylethyl)amide, the title compound was obtained as a white solid (53% yield). m.p. 128-130° C. $^1$H NMR (500 MHz, CDCl$_3$) δ 8.08, 7.99, 7.01, 6.15, 3.89-3.94), 3.77-3.82, 3.52-3.60, 2.39, 1.52, 0.71-0.80, 0.45-0.49, 0.08-0.13. MS (ES+) m/z 452 (M+1).

EXAMPLE 9.2

6-[4-(2-Chloropyridine-3-Carbonyl)Piperazin-1-Yl]Pyridazine-3-Carboxylic Acid (2-Cyclopropylethyl)Amide Following the procedure of Example 9, making variations only as required to use 2-chloropyridine-3-carboxylic acid in place of 2,5-dichlorobenzoic acid to react with 6-piperazin-1-ylpyridazine-3-carboxylic acid (2-cyclopropylethyl)amide, the title compound was obtained as a white solid (44% yield). $^1$H NMR (500 MHz, CDCl$_3$) δ 8.50, 8.08, 7.99, 7.71, 7.37, 7.02, 4.05-4.13, 3.78-3.95, 3.34-3.60, 1.51, 0.71-0.80, 0.45-0.49, 0.08-0.12. MS (ES+) m/z 415 (M+1).

EXAMPLE 9.3

6-[4-(2-Methyl-5-Trifluoromethyloxazole-4-Carbonyl)Piperazin-1-Yl]-Pyridazine-3-Carboxylic Acid (2-Cyclopropylethyl)Amide Following the procedure of Example 9, making variations only as required to use 2-methyl-5-trifluoromethyloxazole-4-carboxylic acid in place of 2,5-dichlorobenzoic acid to react with 6-piperazin-1-yl-pyridazine-3-carboxylic acid (2-cyclopropylethyl)amide, the title compound was obtained as a white solid (58% yield). $^1$H NMR (300 MHz, CDCl$_3$) δ 8.05, 7.98, 6.99, 3.75-3.95, 3.50-3.59, 2.55, 1.51, 0.71-0.80, 0.45-0.49, 0.06-0.12. MS (ES+) m/z 453 (M+1).

EXAMPLE 9.4

6-[4-(2,6-Dichloropyridine-3-Carbonyl)Piperazin-1-Yl]Pyridazine-3-Carboxylic Acid (2-Cyclopropylethyl)Amide Following the procedure of Example 9, making variations only as required to use 2,6-dichloropyridine-3-carboxylic acid in place of 2,5-dichlorobenzoic acid to react with 6-piperazin-1-yl-pyridazine-3-carboxylic acid (2-cyclopropylethyl)amide, the title compound was obtained as a white solid (19% yield). $^1$H NMR (300 MHz, CDCl$_3$) δ 8.06, 7.97, 7.65, 7.37, 7.01, 3.70-4.10, 3.29-3.61, 1.52, 0.68-0.80, 0.42-0.49, 0.06-0.13. MS (ES+) m/z 449 (M+1).

EXAMPLE 9.5

6-[4-(1-Benzyl-5-Trifluoromethyl-1H-[1,2,3]Triazole-4-Carbonyl)-Piperazin-1-Yl]Pyridazine-3-Carboxylic Acid (3-Methylbutyl)Amide Following the procedure of Example 9, making variations only as required to use 1-benzyl-5-trifluoromethyl-1H-[1,2,3]triazole-4-carboxylic acid in place of 2,5-dichlorobenzoic acid to react with 6-piperazin-1-yl-pyridazine-3-carboxylic acid (3-methylbutyl)amide, the title compound was obtained as a white powder (32% yield). $^1$H NMR (300 MHz, DMSO-$d_6$) δ 8.03, 7.81, 7.33-7.27, 6.86, 5.92, 5.39, 3.71, 3.47, 3.05, 2.63, 2.43, 1.65, 1.48, 0.92. MS (ES+) m/z 531.2 (M+1).

EXAMPLE 9.6

6-[4-(3-Benzyl-5-Trifluoromethyl-3H-[1,2,3]Triazole-4-Carbonyl)Piperazin-1-Yl]Pyridazine-3-Carboxylic Acid (3-Methylbutyl)Amide Following the procedure of Example 9, making variations only as required to use 3-benzyl-5-trifluoromethyl-3H-[1,2,3]triazole-4-carboxylic acid in place of 2,5-dichlorobenzoic acid to react with 6-piperazin-1-yl-pyridazine-3-carboxylic acid (3-methylbutyl)amide, the title compound was obtained as a white powder (37% yield). $^1$H NMR (300 MHz, DMSO-$d_6$) δ 8.04, 7.83, 7.36, 7.28, 6.99, 5.69, 3.94, 3.84, 3.70, 3.46, 1.75-1.61, 1.49, 0.91. MS (ES+) m/z 531.2 (M+1).

EXAMPLE 9.7

6-[4-(2-Methyl-5-Trifluoromethyl-2H-[1,2,3]Triazole-4-Carbonyl)Piperazin-1-Yl]Pyridazine-3-Carboxylic Acid (3-Methylbutyl)Amide Following the procedure of Example 9, making variations only as required to use 2-methyl-5-trifluoromethyl-2H-[1,2,3]triazole-4-carboxylic acid in place of 2,5-dichlorobenzoic acid to react with 6-piperazin-1-yl-pyridazine-3-carboxylic acid (3-methylbutyl)amide, the title compound was obtained as a white powder (15% yield). $^1$H NMR (300 MHz, DMSO-$d_6$) δ 8.05, 7.83, 7.00, 4.28, 3.97-3.67, 3.51-3.45, 1.75-1.68, 1.49, 0.92. MS (ES+) m/z 455.2 (M+1).

EXAMPLE 9.8

6-[4-(5-Trifluoromethyl-3H-Imidazole-4-Carbonyl)Piperazin-1-Yl]Pyridazine-3-Carboxylic Acid (3-Methylbutyl)Amide Following the procedure of Example 9, making variations only as required to use 5-trifluoromethyl-3H-imidazole-4-carboxylic acid in place of 2,5-dichlorobenzoic acid to react with 6-piperazin-1-ylpyridazine-3-carboxylic acid (3-methylbutyl)amide, the title compound was obtained as a white powder (48% yield). $^1$H NMR (300 MHz, DMSO-$d_6$) δ 8.03, 7.86, 7.70, 6.99, 3.80, 3.46, 1.75-1.62, 1.48, 0.92. MS (ES+) m/z 440.2 (M+1).

EXAMPLE 9.9

6-[4-(2-Methanesulfonylbenzoyl)Piperazin-1-Yl]Pyridazine-3-Carboxylic Acid (3-Methylbutyl)Amide Following the procedure of Example 9, making variations only as required to use 2-methanesulfonylbenzoic acid in place of 2,5-dichlorobenzoic acid to react with 6-piperazin-1-yl-pyridazine-3-carboxylic acid (3-methylbutyl)amide, the title compound was obtained as a white solid (97% yield). $^1$H NMR (400 MHz, CDCl$_3$) δ 8.11, 8.03, 7.85, 7.74-7.62, 7.38, 4.32-3.33, 3.27, 1.73-1.62, 1.52-1.46, 0.94. MS (ES+) m/z 484.3 (M+1).

EXAMPLE 9.10

6-[4-(2,2-Dimethylbutyryl)Piperazin-1-Yl]Pyridazine-3-Carboxylic Acid (2-Cyclopropylethyl)Amide Following the procedure of Example 9, making variations only as required to use 2,2-dimethylbutyric acid in place of 2,5-dichlorobenzoic acid to react with 6-piperazin-1-ylpyridazine-3-carboxylic acid (2-cyclopropylethyl)amide, the title compound was obtained as a white solid (46% yield). $^1$H NMR (300 MHz, CDCl$_3$) δ 8.05, 8.01, 6.98, 3.86-3.73, 3.57, 1.68, 1.52, 0.92, 0.80-0.72, 0.49-0.45, 0.14-0.08. MS (ES+) m/z 374.3 (M+1).

EXAMPLE 9.11

6-[4-(2,2-Dimethylpentanoyl)Piperazin-1-Yl]Pyridazine-3-Carboxylic Acid (2-Cyclopropylethyl)Amide Following the procedure of Example 9, making variations only as required to use 2,2-dimethylpentanoic acid in place of 2,5-dichlorobenzoic acid to react with 6-piperazin-1-yl-pyridazine-3-carboxylic acid (2-cyclopropylethyl)amide, the title compound was obtained as a white solid (61% yield). $^1$H NMR (300 MHz, CDCl$_3$) δ 8.05, 7.96, 6.98, 3.85-3.72, 3.56, 1.64-1.45, 1.23, 0.96, 0.82-0.62, 0.49-0.45, 0.12-0.07. MS (ES+) m/z 388.2 (M+1).

EXAMPLE 9.12

6-[4-(5-Fluoro-2-Methoxybenzoyl)Piperazin-1-Yl]Pyridazine-3-Carboxylic Acid (2-Cyclopropylethyl)Amide Following the procedure of Example 9, making variations only as required to use 5-fluoro-2-methoxybenzoic acid in place of 2,5-dichlorobenzoic acid to react with 6-piperazin-1-yl-pyridazine-3-carboxylic acid (2-cyclopropylethyl)amide, the title compound was obtained as a white solid (61% yield). $^1$H NMR (300 MHz, CDCl$_3$) δ 8.03, 7.96, 7.10-6.98, 6.86-6.84, 4.03-3.37, 1.51, 0.80-0.72, 0.49-0.44, 0.15-0.10. MS (ES+) m/z 428.1 (M+1).

EXAMPLE 9.13

6-[4-(2-Dimethylaminobenzoyl)Piperazin-1-Yl]Pyridazine-3-Carboxylic Acid (2-Cyclopropylethyl)Amide Following the procedure of Example 9, making variations only as required to use 2-dimethylaminobenzoic acid in place of 2,5-dichlorobenzoic acid to react with 6-piperazin-1-yl-pyridazine-3-carboxylic acid (2-cyclopropylethyl)amide, the title compound was obtained as a white solid (61% yield). $^1$H NMR (300 MHz, CDCl$_3$) δ 8.04, 7.96, 7.36-7.25, 7.05-6.94, 4.17-3.40, 2.80, 1.51, 0.80-0.73, 0.47-0.42, 0.12-0.07.

EXAMPLE 9.14

6-[4-(2-Chloro-5-Dimethylaminobenzoyl)Piperazin-1-Yl]Pyridazine-3-Carboxylic Acid (2-Cyclopropylethyl)Amide Following the procedure of Example 9, making variations only as required to use 2-chloro-5-dimethylaminobenzoic acid in place of 2,5-dichlorobenzoic acid to react with 6-piperazin-1-yl-pyridazine-3-carboxylic acid (2-cyclopropylethyl)-amide, the title compound was obtained as a white solid (53% yield). $^1$H NMR (300 MHz, CDCl$_3$) δ 8.04, 7.96, 7.39, 6.94, 6.66, 6.55, 4.14-3.32, 2.93, 1.52, 0.75-0.69, 0.48-0.42, 0.11-0.05. MS (ES+) m/z 457.4 (M+1).

EXAMPLE 9.15

6-[4-(2,5-Dimethylbenzoyl)Piperazin-1-Yl]Pyridazine-3-Carboxylic Acid (2-Cyclopropylethyl)Amide Following the procedure of Example 9, making variations only as required to use 2,5-dimethylbenzoic acid in place of 2,5-dichlorobenzoic acid to react with 6-piperazin-1-yl-pyridazine-3-carboxylic acid (2-cyclopropylethyl)amide, the title compound was obtained as a white solid (56% yield). $^1$H NMR (300 MHz, CDCl$_3$) δ 8.05, 7.96, 7.16-7.11, 7.03-6.97, 4.12-3.67, 2.23, 2.22, 1.52, 0.82-0.69, 0.48-0.42, 0.11-0.05. MS (ES+) m/z 408.3 (M+1).

EXAMPLE 9.16

6-[4-(2,5-Dichlorobenzoyl)Piperazin-1-Yl]Pyridazine-3-Carboxylic Acid (2-Cyclopropylethyl)Amide Following the procedure of Example 9, making variations only as required to use 2,5-dichlorobenzoic acid in place of 2,5-dichlorobenzoic acid to react with 6-piperazin-1-yl-pyridazine-3-carboxylic acid (2-cyclopropylethyl)amide, the title compound was obtained as a white solid (56% yield). $^1$H NMR (300 MHz, CDCl$_3$) δ 8.05, 7.96, 7.38-7.30, 6.97, 4.12-3.23, 1.50, 0.80-0.67, 0.51-0.38, 0.16-0.06. MS (ES+) m/z 448.2 (M+1).

EXAMPLE 9.17

6-[4-(1-Methyl-1H-Pyrrole-2-Carbonyl)Piperazin-1-Yl]Pyridazine-3-Carboxylic Acid (2-Cyclopropylethyl)Amide Following the procedure of Example 9, making variations only as required to use 1-methyl-1H-pyrrole-2-carboxylic acid in place of 2,5-dichlorobenzoic acid to react with 6-piperazin-1-yl-pyridazine-3-carboxylic acid (2-cyclopropylethyl)-amide, the title compound was obtained as a white powder (51.8% yield). $^1$H NMR (500 MHz, CDCl$_3$) δ 8.07, 8.01, 7.00, 6.75, 6.40, 6.12, 4.00-3.80, 3.58, 1.52, 0.76, 0.48, 0.10. MS (ES+) m/z 383 (M+1).

EXAMPLE 9.18

6-[4-(4,4,4-Trifluorobut-2-Enoyl)Piperazin-1-Yl]Pyridazine-3-Carboxylic Acid (2-Cyclopropylethyl)Amide Following the procedure of Example 9, making variations only as required to use 4,4,4-trifluorobut-2-enoic acid in place of 2,5-dichlorobenzoic acid to react with 6-piperazin-1-yl-pyridazine-3-carboxylic acid (2-cyclopropylethyl)amide, the title compound was obtained as a white powder (19.6% yield). $^1$H NMR (500 MHz, CDCl$_3$) δ 8.09, 8.00, 7.00, 6.81, 3.96-3.88, 3.78, 3.57, 1.53, 0.76, 0.48, 0.10. MS (ES+) m/z 398 (M+1).

EXAMPLE 9.19

6-[4-(1-Hydroxycyclopropanecarbonyl)Piperazin-1-Yl]Pyridazine-3-Carboxylic Acid (2-Cyclopropylethyl)Amide Following the procedure of Example 9, making variations only as required to use 1-hydroxycyclopropanecarboxylic acid in place of 2,5-dichlorobenzoic acid to react with 6-piperazin-1-yl-pyridazine-3-carboxylic acid (2-cyclopropylethyl)amide, the title compound was obtained as a white powder (53.4% yield). $^1$H NMR (500 MHz, CDCl$_3$) δ 8.07, 8.03, 7.01, 3.98-3.73, 3.58, 1.53, 1.16, 1.02, 0.76, 0.48, 0.10. MS (ES+) m/z 360 (M+1).

EXAMPLE 9.20

6-[4-(4,4,4-Trifluoro-3-Hydroxy-3-Trifluoromethylbutyryl)Piperazin-1-Yl]Pyridazine-3-Carboxylic Acid (2-Cyclopropylethyl)Amide Following the procedure of Example 9, making variations only as required to use 4,4,4-trifluoro-3-hydroxy-3-trifluoromethylbutyryic acid in place of 2,5-dichlorobenzoic acid to react with 6-piperazin-1-yl-pyridazine-3-carboxylic acid (2-cyclopropylethyl)amide, the title compound was obtained as a white powder (45.6% yield). $^1$H NMR (300 MHz, CDCl$_3$) δ 8.08, 8.03, 7.98, 7.00, 3.95-3.71, 3.56, 2.89, 1.55, 0.75, 0.48, 0.10. $^{13}$C NMR (CDCl$_3$) δ 168.5, 162.8, 159.8, 145.8, 127.3, 112.5, 45.5, 44.5, 44.1, 41.3, 39.7, 34.5, 27.2, 8.6, 4.2. MS (ES+) m/z 484 (M+1).

EXAMPLE 9.21

6-[4-(4,4,4-Trifluoro-3-Hydroxy-3-Methylbutyryl)Piperazin-1-Yl]-Pyridazine-3-Carboxylic Acid (2-Cyclopropylethyl)Amide Following the procedure of Example 9, making variations only as required to use 4,4,4-trifluoro-3-hydroxy-3-methylbutyric acid in place of 2,5-dichlorobenzoic acid to react with 6-piperazin-1-yl-pyridazine-3-carboxylic acid (2-cyclopropylethyl)amide, the title compound was obtained as a white powder (50.1% yield). $^1$H NMR (300 MHz, CDCl$_3$) δ 8.07, 7.96, 6.98, 6.23, 4.05-3.52, 2.90, 2.47, 1.53-1.43, 0.76, 0.46, 0.09. MS (ES+) m/z 430 (M+1).

EXAMPLE 9.22

6-(4-Cyclobutanecarbonylpiperazin-1-Yl)Pyridazine-3-CARBOXYLIC ACID (2-Cyclopropylethyl)Amide Following the procedure of Example 9, making variations only as required to use 4-cyclobutanecarboxylic acid in place of 2,5-dichlorobenzoic acid to react with 6-piperazin-1-yl-pyridazine-3-carboxylic acid (2-cyclopropylethyl)amide, the title compound was obtained as a white powder (45.6% yield). $^1$H NMR (300 MHz, CDCl$_3$) δ 8.03, 7.97, 6.97, 3.82-3.64, 3.57-3.49, 3.26, 2.43-2.27, 2.22-2.05 2.02-1.81, 1.50, 0.75, 0.46, 0.08. MS (ES+) m/z 358 (M+1).

EXAMPLE 9.23

6-[4-(2-Trifluoromethylcyclopropanecarbonyl)Piperazin-1-Yl]-Pyridazine-3-Carboxylic Acid (2-Cyclopropylethyl)Amide Following the procedure of Example 9, making variations only as required to use 2-trifluoromethylcyclopropanecarboxylic acid in place of 2,5-dichlorobenzoic acid to react with 6-piperazin-1-yl-pyridazine-3-carboxylic acid (2-cyclopropylethyl)amide, the title compound was obtained as a white powder (30.9% yield). $^1$H NMR (300 MHz, CDCl$_3$) δ 8.03, 7.98, 7.00, 3.97-3.57, 2.20, 1.65, 1.50, 1.26, 0.75, 0.46, 0.09. MS (ES+) m/z 412 (M+1).

EXAMPLE 9.24

6-[4-(4,4,4-Trifluoro-3-Trifluoromethylbut-2-Enoyl)Piperazin-1-Yl]Pyridazine-3-Carboxylic Acid (2-Cyclopropylethyl)Amide Following the procedure of Example 9, making variations only as required to use 4,4,4-trifluoro-3-trifluoromethylbut-2-enoic acid in place of 2,5-dichlorobenzoic acid to react with 6-piperazin-1-yl-pyridazine-3-carboxylic acid (2-cyclopropylethyl)amide, the title compound was obtained as a white powder (45.4% yield). $^1$H NMR (CDCl$_3$) δ 8.07, 7.97, 7.10, 7.01, 3.87-3.74, 3.58-3.50, 1.54-1.47, 0.78-0.68, 0.48-0.42, 0.10-0.05.

$^{13}$C NMR (CDCl$_3$) δ 162.8, 161.1, 159.8, 145.8, 135.2, 135.1, 127.3, 124.5, 112.7, 45.5, 44.4, 44.3, 40.9, 39.7, 34.5, 8.6, 4.2. MS (ES+) m/z 466 (M+1).

EXAMPLE 9.25

6-[4-(2-Trifluoromethylbenzoyl)Piperazin-1-Yl]Pyridazine-3-Carboxylic Acid Cyclobutylmethylamide Following the procedure of Example 9, making variations only as required to use 2-trifluoromethylbenzoic acid in place of 2,5-dichlorobenzoic acid to react with 6-piperazin-1-yl-pyridazine-3-carboxylic acid cyclobutylmethylamide, the title compound was obtained as a white powder (45.0% yield). $^1$H NMR (CDCl$_3$) δ 8.04, 7.83, 7.72, 7.64-7.51, 7.32, 7.00, 4.10-4.01, 3.90-3.66, 3.49-3.27, 2.63-2.47, 2.11-1.67. $^{13}$C NMR (CDCl$_3$) δ 167.7, 162.9, 159.8, 145.4, 134.2, 132.4, 129.6, 127.4, 126.9, 126.8, 125.4, 121.8, 112.8, 46.4, 44.6, 41.2, 35.1, 25.7, 18.3. MS (ES+) m/z 448 (M+1).

EXAMPLE 9.26

6-{4-[2-(2-Trifluoromethylphenyl)Acetyl]Piperazin-1-Yl}Pyridazine-3-Carboxylic Acid (2-Cyclopropylethyl)Amide Following the procedure of Example 9, making variations only as required to use (2-trifluoromethylphenyl)acetic acid in place of 2,5-dichlorobenzoic acid to react with 6-piperazin-1-ylpyridazine-3-carboxylic acid (2-cyclopropylethyl)amide, the title compound was obtained as a white solid (78.7% yield). $^1$H NMR (300 MHz, CDCl$_3$) δ 8.03, 7.97, 7.67-7.64, 7.53-7.48, 7.39-7.35, 6.96, 3.91, 3.87-3.67, 3.66-3.6, 3.58-3.51, 1.53-1.46, 0.78-0.64, 0.48-0.42, 0.10-0.06. $^{13}$C NMR (75 MHz, CDCl$_3$) δ 168.8, 162.9, 159.9, 145.3, 133.2, 132.0, 131.5, 128.5, 128.2, 127.2, 127.0, 126.3, 126.2, 125.5, 112.3, 45.0, 44.7, 44.2, 41.2, 39.6, 37.13, 37.11, 34.4, 8.6, 4.2. MS (ES+) m/z 462.2 (M+1).

EXAMPLE 9.27

6-[4-(2-Cyanobenzoyl)Piperazin-1-Yl]-Pyridazine-3-Carboxylic Acid (2-Cyclopropylethyl)Amide Following the procedure of Example 9, making variations only as required to use 2-cyanobenzoic acid in place of 2,5-dichlorobenzoic acid to react with 6-piperazin-1-yl-pyridazine-3-carboxylic acid (2-cyclopropylethyl)amide, the title compound was obtained as a white solid (25.8% yield). $^1$H NMR (300 MHz, CDCl$_3$) δ 8.05, 7.97, 7.76-7.72, 7.69-7.66, 7.58-7.55, 7.53-7.43, 6.99, 4.3-3.94, 3.88-3.85, 3.58-3.51, 1.49, 0.78-0.65, 0.48-0.37, 0.16-0.02. $^{13}$C NMR (75 MHz, CDCl$_3$) δ 166.5, 162.8, 159.9, 145.3, 139.3, 133.3, 133.04, 129.9, 127.6, 127.03, 116.8, 112.4, 109.9, 46.4, 44.7, 44.6, 41.6, 39.6, 34.4, 8.6, 4.1. MS (ES+) m/z 405.2 (M+1).

EXAMPLE 9.28

6-[4-(4-Trifluoromethylpyridine-3-Carbonyl)Piperazin-1-Yl]Pyridazine-3-Carboxylic Acid (3-Methylbutyl)Amide Following the procedure of Example 9, making variations only as required to use 4-trifluoromethylpyridine-3-carboxylic acid in place of 2,5-dichlorobenzoic acid to react with 6-piperazin-1-yl-pyridazine-3-carboxylic acid (3-methylbutyl)amide, the title compound was obtained as a white powder (69% yield). $^1$H NMR (300 MHz, CDCl$_3$) δ 8.87, 8.69, 8.05, 7.82, 7.62, 7.00, 4.10-3.69, 3.51-3.44, 3.38-3.35, 1.75-1.61, 1.52-1.45, 0.90. MS (ES+) m/z 451.3 (M+1).

EXAMPLE 9.29

6-[4-(4,4,4-Trifluoro-3-Methylbut-2-Enoyl)Piperazin-1-Yl]-Pyridazine-3-Carboxylic Acid (3-Methylbutyl)Amide Following the procedure of Example 9, making variations only as required to use to use 4,4,4-trifluoro-3-methylbut-2-enoic acid in place of 2,5-dichlorobenzoic acid to react with 6-piperazin-1-yl-pyridazine-3-carboxylic acid (3-methylbutyl)amide, the title compound was obtained as a white powder (62% yield). $^1$H NMR (300 MHz, CDCl$_3$) δ 8.05, 7.83, 7.00, 6.55, 3.86-3.83, 3.80-3.73, 3.62-3.60, 3.48, 2.01, 1.75-1.62, 1.49, 0.92. MS (ES+) m/z 414.4 (M+1).

EXAMPLE 9.30

6-[4-(1-Trifluoromethylcyclopropanecarbonyl)Piperazin-1-Yl]-Pyridazine-3-Carboxylic Acid (3-Methylbutyl)Amide Following the procedure of Example 9, making variations only as required to use 1-trifluoromethylcyclopropanecarboxylic acid to react with 6-piperazin-1-yl-pyridazine-3-carboxylic acid (3-methylbutyl)amide, the title compound was obtained as a white powder (72% yield). $^1$H NMR (300 MHz, CDCl$_3$) δ 8.05, 7.83, 6.98, 3.90-3.80, 3.48, 1.66, 1.48, 1.39-1.35, 1.18-1.14, 0.92. MS (ES+) m/z 414.2 (M+1).

EXAMPLE 9.31

6-[4-(Pyridine-2-Carbonyl)Piperazin-1-Yl]Pyridazine-3-Carboxylic Acid (2-Cyclopropylethyl)Amide Following the procedure of Example 9, making variations only as required to use pyridine-2-carboxylic acid to react with 6-piperazin-1-yl-pyridazine-3-carboxylic acid (2-cyclopropylethyl)amide, the title compound was obtained as a white powder (70% yield). $^1$H NMR (300 MHz, CDCl$_3$) δ 8.60-8.58, 8.03, 7.98, 7.86-7.79, 7.73-7.71, 7.39-7.35, 6.98, 3.96-3.83, 3.54, 1.50, 0.78-0.69, 0.47-0.41, 0.08-0.05. MS (ES+) m/z 381.2 (M+1).

EXAMPLE 9.32

6-[4-(2-Trifluoromethylfuran-3-Carbonyl)Piperazin-1-Yl]Pyridazine-3-Carboxylic Acid (2-Cyclopropylethyl)Amide Following the procedure of Example 9, making variations only as required to use 2-trifluoromethylfuran-3-carboxylic acid to react with 6-piperazin-1-yl-pyridazine-3-carboxylic acid (2-cyclopropylethyl)amide, the title compound was obtained as a white powder (71% yield). $^1$H NMR (300 MHz, CDCl$_3$) δ 8.04, 7.96, 7.56, 7.00, 6.54, 3.9-3.7, 3.6-3.5, 1.49, 0.79-0.66, 0.47-0.41, 0.09-0.04. $^{13}$C NMR (300 MHz, CDCl$_3$) δ 161.78, 160.01, 145.60, 145.05, 138.14, 137.57, 127, 15, 121.74, 120.54, 112.54, 110.88, 46.33, 44.59, 41.43, 39.67, 34.52, 8.64, 4.23. MS (ES+) m/z 438.2 (M+1).

EXAMPLE 10

Synthesis of 6-[4-(5-Trifluoromethyl-3H-[1,2,3]Triazole-4-Carbonyl)Piperazin-1-Yl]-Pyridazine-3-Carboxylic Acid (3-Methylbutyl)Amide 6-[4-(3-Benzyl-5-trifluoromethyl-3H-[1,2,3]triazole-4-carbonyl)piperazin-1-yl]pyridazine-3-carboxylic acid (3-methylbutyl)amide (0.4 g, 0.75 mmol) was dissolved in 10 mL of MeOH with 3 drops of acetic acid and 0.2 g of 10% Pd/C was added. The reaction mixture was kept under normal pressure of H$_2$ at ambient temperature overnight. After filtration the reaction mixture was evaporated under reduced pressure and the residue was recrystallized from 3 mL of EtOH to give 120 mg (36% yield) of 6-[4-(5-trifluoromethyl-3H-[1,2,3]triazole-4-carbonyl)-piperazin-1-yl]pyridazine-3-carboxylic acid (3-methylbutyl)amide as a white powder. $^1$H NMR (500 MHz, Acetone-d$_6$) δ 8.18, 7.91, 7.32, 3.92-3.72, 3.45, 1.67, 1.52, 0.92.

EXAMPLE 11

Synthesis of 6-[4-(2-Trifluoromethylbenzyl)Piperazin-1-Yl]Pyridazine-3-Carboxylic Acid (3-Methylbutyl)Amide A mixture of 6-piperazin-1-yl-pyridazine-3-carboxylic acid (3-methylbutyl)amide (0.255 mmol), 2-trifluoromethylbenzyl chloride (0.255 mmol), and 1,8-diazabicylco[5.4.0]undec-7-ene (0.77 mmol) was stirred and heated at 60° C. overnight. The reaction mixture was then diluted with EtOAc (100 mL) and washed with aqueous saturated NaHCO$_3$ (2×20 mL) and brine (2×20 mL). The organic layer was dried over anhydrous Na$_2$SO$_4$, concentrated, and purified by flash chromatography to give the title compound as a white solid (80 mg, 72% yield). $^1$H NMR (500 MHz, CDCl$_3$) δ 8.00, 7.86, 7.82, 7.65, 7.55, 7.37, 6.95, 3.74-3.79, 3.73, 3.46-3.52, 2.62, 1.65-1.76, 1.52, 0.94. MS (ES+) m/z 436 (M+1).

EXAMPLE 11.1

6-[4-(2-Trifluoromethylbenzyl)Piperazin-1-Yl]Pyridazine-3-Carboxylic Acid (2-Cyclopropylethyl)Amide Following the procedure of Example 11, making variations only as required to use 6-piperazin-1-yl-pyridazine-3-carboxylic acid (2-cyclopropylethyl)amide in place of 6-piperazin-1-yl-pyridazine-3-carboxylic acid (3-methylbutyl)amide to react with 2-trifluoromethylbenzyl chloride, the title compound was obtained as a white solid (32% yield). m.p. 106-108° C. $^1$H NMR (500 MHz, CDCl$_3$) δ 7.97-8.04, 7.83, 7.65, 7.55, 7.37, 6.96, 3.77, 3.73, 3.56, 2.63, 1.52, 0.71-0.80, 0.45-0.49, 0.08-0.13. MS (ES+) m/z 434 (M+1).

EXAMPLE 11.2

6-[4-(5-Fluoro-2-Trifluoromethylbenzyl)Piperazin-1-Yl]Pyridazine-3-Carboxylic Acid (2-Cyclopropylethyl)Amide Following the procedure of Example 11, making variations only as required to use 5-fluoro-2-trifluoromethylbenzyl chloride in place of 2-trifluoromethylbenzyl chloride to react with 6-piperazin-1-yl-pyridazine-3-carboxylic acid (2-cyclopropylethyl)amide, the title compound was obtained as a white solid (40% yield). $^1$H NMR (300 MHz, CDCl$_3$) δ 7.95-8.01, 7.57-7.68, 7.04, 6.95, 3.79, 3.71, 3.56, 2.64, 1.51, 0.68-0.82, 0.43-0.51, 0.06-0.13. MS (ES+) m/z 452 (M+1).

EXAMPLE 11.3

6-[4-(4-Fluoro-2-Trifluoromethylbenzyl)-Piperazin-1-Yl]Pyridazine-3-Carboxylic Acid (2-Cyclopropylethyl)Amide Following the procedure of Example 11, making variations only as required to use 4-fluoro-2-trifluoromethylbenzyl chloride in place of 2-trifluoromethylbenzyl chloride to react with 6-piperazin-1-ylpyridazine-3-carboxylic acid (2-cyclopropylethyl)amide, the title compound was obtained as a white solid (38% yield). $^1$H NMR (300 MHz, CDCl$_3$) δ

7.96-8.04, 7.81, 7.36, 7.20-7.29, 6.96, 3.76, 3.68, 3.56, 2.61, 1.51, 0.68-0.84, 0.43-0.51, 0.06-0.13. MS (ES+) m/z 452 (M+1).

EXAMPLE 11.4

6-[4-(5-Chloro-2-Trifluoromethylbenzyl)Piperazin-1-Yl]Pyridazine-3-Carboxylic Acid (2-Cyclopropylethyl)Amide Following the procedure of Example 11, making variations only as required to use 5-chloro-2-trifluoromethylbenzyl chloride in place of 2-trifluoromethylbenzyl chloride to react with 6-piperazin-1-yl-pyridazine-3-carboxylic acid (2-cyclopropylethyl)amide, the title compound was obtained as a white solid (48% yield).

$^1$H NMR (300 MHz, CDCl$_3$) δ 7.96-8.05, 7.87, 7.58, 7.34, 6.97, 3.80, 3.70, 3.56, 2.64, 1.53, 1.51, 0.70-0.83, 0.43-0.51, 0.07-0.13. MS (ES+) m/z 468 (M+1).

EXAMPLE 11.5

6-[4-(2-Chloro-4-Fluorobenzyl)Piperazin-1-Yl]Pyridazine-3-Carboxylic Acid (2-Cyclopropylethyl) Amide Following the procedure of Example 11, making variations only as required to use 2-chloro-4-fluorobenzyl chloride in place of 2-trifluoromethylbenzyl chloride to react with 6-piperazin-1-yl-pyridazine-3-carboxylic acid (2-cyclopropylethyl)amide, the title compound was obtained as a white solid (26% yield). $^1$H NMR (300 MHz, CDCl$_3$) δ 7.92-8.03, 7.38-7.50, 7.06-7.14, 6.88-7.03, 3.68-3.78, 3.62, 3.46-3.58, 2.55-2.69, 1.42-1.54, 0.68-0.80, 0.40-0.49, 0.02-0.13. MS (ES+) m/z 418 (M+1).

EXAMPLE 11.6

6-[4-(2,5-Dichlorobenzyl)Piperazin-1-Yl]Pyridazine-3-Carboxylic Acid (2-Cyclopropylethyl) Amide Following the procedure of Example 11, making variations only as required to use 2,5-dichlorobenzyl chloride in place of 2-trifluoromethylbenzyl chloride to react with 6-piperazin-1-yl-pyridazine-3-carboxylic acid (2-cyclopropylethyl)amide, the title compound was obtained as a white solid (43% yield). $^1$H NMR (300 MHz, CDCl$_3$) δ 7.96-8.04, 7.53, 7.16-7.33, 6.96, 3.75-3.84, 3.64, 3.56, 2.62-2.70, 1.53, 1.51, 0.70-0.83, 0.43-0.51, 0.06-0.13. MS (ES+) m/z 434 (M+1).

EXAMPLE 11.7

6-[4-(5-Fluoro-2-Trifluoromethylbenzyl)Piperazin-1-Yl]Pyridazine-3-Carboxylic Acid (3-Methylbutyl) Amide Following the procedure of Example 11, making variations only as required to use 5-fluoro-2-trifluoromethylbenzyl chloride in place of 2-trifluoromethylbenzyl chloride to react with 6-piperazin-1-yl-pyridazine-3-carboxylic acid (3-methylbutyl)amide, the title compound was obtained as a white solid (34% yield). $^1$H NMR (300 MHz, CDCl$_3$) δ 8.02, 7.82-7.92, 7.57-7.68, 7.00-7.09, 6.96, 3.79, 3.71, 3.50, 2.64, 1.64-1.78, 1.51, 0.94. MS (ES+) m/z 454 (M+1).

EXAMPLE 11.8

6-[4-(2,4-Dichlorobenzyl)-Piperazin-1-Yl]Pyridazine-3-Carboxylic Acid (2-Cyclopropylethyl) Amide Following the procedure of Example 11, making variations only as required to use 2,4-dichlorobenzyl chloride in place of 2-trifluoromethylbenzyl chloride to react with 6-piperazin-1-yl-pyridazine-3-carboxylic acid (2-cyclopropylethyl)amide, the title compound was obtained as a light yellow solid (75% yield). $^1$H NMR (300 MHz, CDCl$_3$) δ 7.95-8.02, 7.44, 7.38, 7.23, 6.93, 3.70-3.77, 3.60-3.63, 3.54, 2.60-2.65, 1.50, 0.74, 0.45, 0.08. MS (ES+) m/z 434 (M+1).

EXAMPLE 11.9

6-[4-(5-Fluoro-2-Trifluoromethylbenzyl)Piperazin-1-Yl]Pyridazine-3-Carboxylic Acid (3-Cyclopropylpropyl)Amide Following the procedure of Example 11, making variations only as required to use 5-fluoro-2-trifluoromethylbenzyl chloride in place of 2-trifluoromethylbenzyl chloride to react with 6-piperazin-1-yl-pyridazine-3-carboxylic acid (3-cyclopropylpropyl)amide, the title compound was obtained as a light yellow solid (34% yield). $^1$H NMR (300 MHz, CDCl$_3$) δ 7.98, 7.88, 7.55-7.65, 7.2, 6.93, 3.68-3.85, 3.50, 2.60, 1.70, 1.25, 0.65, 0.40, 0.09. MS (ES+) m/z 466 (M+1).

EXAMPLE 11.10

Synthesis of 6-[4-(5-Fluoro-2-Trifluoromethylbenzoyl)Piperazin-1-Yl]Pyridazine-3-Carboxylic Acid Pent-4-Enylamide Following the procedure of Example 11, making variations only as required to use 5-fluoro-2-(trifluoromethyl)benzyl chloride in place of 2-trifluoromethylbenzyl chloride to react with 6-piperazin-1-ylpyridazine-3-carboxylic acid pent-4-enylamide, the title compound was obtained as a white powder (17.3% yield). $^1$H NMR (300 MHz, CDCl$_3$) δ 7.99, 7.92, 7.77, 7.27, 7.11, 7.00, 5.91-5.78, 5.09-4.95, 4.08-3.65, 3.47-3.27, 2.18-2.11, 1.75-1.65. $^{13}$C NMR (75 MHz, CDCl$_3$) δ 166.1, 165.7, 162.9, 162.7, 160.2, 145.5, 138.0, 129.3, 129.6, 129.5, 116.7, 114.9, 114.8, 114.6, 112.4, 46.3, 44.4, 41.2, 38.7, 31.1, 28.9. MS (ES+) m/z 466.3 (M+1).

EXAMPLE 12

Synthesis of 6-[4-(2-Aminobenzoyl)Piperazin-1-Yl] Pyridazine-3-Carboxylic Acid (3-Methylbutyl) Amide 6-[4-(2-Nitrobenzoyl)piperazin-1-yl]pyridazine-3-carboxylic acid (3-methyl-butyl)amide (100 mg, 0.235 mmol) was hydrogenated with 10 mg 10% Pd/C as catalyst at ambient temperature under 1 atm for 24 hours. The mixture was filtered through a celite cake. The filtrate was concentrated and purified by flash chromatography (ethyl acetate) to give a white solid (83% yield). $^1$H NMR (500 MHz, CDCl$_3$) δ 8.05, 7.86, 7.19-7.23, 7.10-7.13, 6.99, 4.40, 3.74-3.88, 3.50, 1.65-1.75, 1.52, 0.94. MS (ES+) m/z 397 (M+1).

EXAMPLE 13

Synthesis of {6-[4-(2-Trifluoromethylbenzoyl)Piperazin-1-Yl]Pyridazin-3-Yl}Carbamic Acid 3,3-Dimethylbutyl Ester To a solution of [4-(6-aminopyridazin-3-yl)piperazin-1-yl](2-trifluoromethyl-phenyl)methanone (200 mg, 0.57 mmol) in 10 mL of dioxane was added trichloromethyl chloroformate (112.7 mg, 0.57 mmol) and stirred at ambient temperature. After 30 minutes 3,3-dimethylbutan-1-ol (175.5 mg, 1.71 mmol) and triethylamine (57.6 mg, 0.57 mmol) were added and the temperature was raised to 80° C. The mixture was stirred for 3 h under $N_2$, and then concentrated. The residue was dissolved in dichloromethane (100 mL), and washed with 1 N HCl (2×20 mL), saturated $NaHCO_3$ (2×20 mL) and finally with brine (2×20 mL). The combined organic extract was dried over anhydrous $Na_2SO_4$, concentrated, and then purified by column chromatography eluted with hexane:ethyl acetate (1:2). The product was obtained as a white solid (30 mg, 11% yield). $^1H$ NMR (300 MHz, DMSO-$d_6$) δ 10.38, 7.89, 7.83, 7.77, 7.67, 7.54, 7.47, 4.14, 3.10-3.90, 1.55, 0.95.

EXAMPLE 13.1

{6-[4-(2-Trifluoromethylbenzoyl)Piperazin-1-Yl]Pyridazin-3-Yl}Carbamic Acid 2-Cyclopropylethyl Ester Following the procedure of Example 13, making variations only as required to use 2-cyclopropylethanol in place of 3,3-dimethylbutan-1-ol to react with [4-(6-aminopyridazin-3-yl)piperazin-1-yl](2-trifluoromethylphenyl)methanone, the title compound was obtained as a white solid (8.3% yield). $^1H$ NMR (500 MHz, CDCl$_3$) δ 8.11, 7.73, 7.65, 7.63, 7.55, 7.36, 7.04, 4.25, 3.95-4.02, 3.88-3.94, 3.61-3.65, 3.52-3.56, 3.32, 1.58, 0.71-0.80, 0.44-0.50, 0.05-0.013. MS (ES+) m/z 464 (M+1).

EXAMPLE 14

Synthesis of 6-[4-(4,4,4-Trifluoro-2-Methylbutyryl)Piperazin-1-Yl]Pyridazine-3-Carboxylic Acid (3-Methylbutyl)Amide A mixture of TFA salt of 6-piperazin-1-yl-pyridazine-3-carboxylic acid (3-methylbutyl)amide (100 mg, 0.25 mmol), 4,4,4-trifluoro-2-methylbutyric acid (47.8 mg, 0.31 mmol), 1,8-diazabicylco[5.4.0]undec-7-ene (77.8 mg, 0.51 mmol) and 1-hydroxy-benozotriazole hydrate (41.4 mg, 0.31 mmol) in DMF (2 mL) was stirred at ambient temperature for 15 minutes. 1-(3-Dimethylaminopropyl)-3-ethylcarbodiimide (47.6 mg, 0.31 mmol) was added to this solution. The reaction mixture was stirred at ambient temperature overnight and then diluted with ethyl acetate (50 mL) and washed with aqueous saturated $NaHCO_3$ (2×20 mL) and finally with brine (2×20 mL). The organic extract was dried over anhydrous $Na_2SO_4$, concentrated, and then purified by column chromatography eluted with hexanes:ethyl acetate (1:2). The product was obtained as a white flaky solid (80 mg, 75% yield). $^1H$ NMR (300 MHz, CDCl$_3$) δ 8.07, 7.85, 7.01, 3.60-4.00, 3.50, 3.15, 2.80, 2.21, 1.70, 1.50, 1.25, 0.95. MS (ES+) m/z 416 (M+1).

EXAMPLE 14.1

6-[4-(4,4,4-Trifluoro-3-Methylbutyryl)Piperazin-1-Yl]Pyridazine-3-Carboxylic Acid (3-Methylbutyl)Amide Following the procedure of Example 14, making variations only as required to use 4,4,4-trifluoro-3-methylbutyric acid in place of 4,4,4-trifluoro-2-methylbutyric acid to react with 6-piperazin-1-yl-pyridazine-3-carboxylic acid (3-methylbutyl)amide, the title compound was obtained as a white flaky solid (63% yield). $^1H$ NMR (300 MHz, CDCl$_3$) δ 8.07, 7.85, 7.00, 3.69-3.98, 3.67, 3.50, 3.00, 2.71, 2.35, 1.70, 1.50, 1.20, 0.95. MS (ES+) m/z 415 (M+1).

EXAMPLE 14.2

6-[4-(4,4,4-Trifluorobutyryl)Piperazin-1-Yl]Pyridazine-3-Carboxylic Acid (3-Methylbutyl)Amide Following the procedure of Example 14, making variations only as required to use 4,4,4-trifluorobutyric acid in place of 4,4,4-trifluoro-2-methylbutyric acid to react with 6-piperazin-1-yl-pyridazine-3-carboxylic acid (3-methylbutyl)amide, the title compound was obtained as a white flaky solid (49% yield). $^1H$ NMR (300 MHz, CDCl$_3$) δ 8.07, 7.85, 7.00, 3.91, 3.82, 3.72, 3.67, 3.50, 2.50-2.67, 1.70, 1.50, 0.95. MS (ES+) m/z 402 (M+1).

EXAMPLE 14.3

6-[4-(6-Chloropyridine-2-Carbonyl)Piperazin-1-Yl]Pyridazine-3-Carboxylic Acid (3-Methylbutyl)Amide Following the procedure of Example 14, making variations only as required to use 6-chloropyridine-2-carboxylic acid in place of 4,4,4-trifluoro-2-methylbutyric acid to react with 6-piperazin-1-yl-pyridazine-3-carboxylic acid (3-methylbutyl)amide, the title compound was obtained as a white flaky solid (12% yield). $^1H$ NMR (300 MHz, CDCl$_3$) δ 8.05, 7.87, 7.82, 7.70, 7.43, 7.00, 3.80-4.00, 3.50, 1.70, 1.53, 0.95. MS (ES+) m/z 417 (M+1).

EXAMPLE 14.4

6-[4-(2-Methylcyclohexanecarbonyl)Piperazin-1-Yl]Pyridazine-3-Carboxylic Acid (2-Cyclopropylethyl)Amide Following the procedure of Example 14, making variations only as required to use 2-methylcyclohexanecarboxylic acid in place of 4,4,4-trifluoro-2-methylbutyric acid to react with 6-piperazin-1-yl-pyridazine-3-carboxylic acid (2-cyclopropylethyl)amide, the title compound was obtained as a white solid (60% yield). $^1H$ NMR (300 MHz, CDCl$_3$) δ 8.08, 8.00, 7.00, 3.50-4.00, 2.70, 2.05, 1.20-1.90, 0.90, 0.75, 0.45, 0.10. MS (ES+) m/z 400 (M+1,).

EXAMPLE 14.5

6-[4-(3-Methylcyclohexanecarbonyl)Piperazin-1-Yl]Pyridazine-3-Carboxylic Acid (2-Cyclopropylethyl)Amide Following the procedure of Example 14, making variations only as required to use 3-methylcyclohexanecarboxylic acid in place of 4,4,4-trifluoro-2-methylbutyric acid to react with 6-piperazin-1-yl-pyridazine-3-carboxylic acid (2-cyclopropylethyl)amide, the title compound was obtained as a white solid (27% yield). $^1$H NMR (300 MHz, CDCl$_3$) δ 8.06, 7.99, 6.99, 3.89, 3.79, 3.65-3.72, 3.56, 2.55, 1.20-1.86, 0.99, 0.92, 0.75, 0.47, 0.10. MS (ES+) m/z 400 (M+1).

EXAMPLE 14.6

6-[4-(4-Methylcyclohexanecarbonyl)Piperazin-1-Yl] Pyridazine-3-Carboxylic Acid (2-Cyclopropylethyl) Amide Following the procedure of Example 14, making variations only as required to use 4-methylcyclohexanecarboxylic acid in place of 4,4,4-trifluoro-2-methylbutyric acid to react with 6-piperazin-1-yl-pyridazine-3-carboxylic acid (2-cyclopropylethyl)amide, the title compound was obtained as a white solid (43% yield). $^1$H NMR (300 MHz, CDCl$_3$) δ 8.07, 7.09, 7.05, 3.89, 3.79, 3.64-3.70, 3.56, 2.40-2.60, 1.65-1.88, 1.50-1.62, 0.99, 0.91, 0.75, 0.48, 0.10. MS (ES+) m/z 400 (M+1).

EXAMPLE 14.7

2-{4-[6-(2-Cyclopropylethylcarbamoyl)Pyridazin-3-Yl]Piperazine-1-Carbonyl}Benzoic Acid Methyl Ester Following the procedure of Example 14, making variations only as required to use phthalic acid monomethyl ester in place of 4,4,4-trifluoro-2-methylbutyric acid to react with 6-piperazin-1-yl-pyridazine-3-carboxylic acid (2-cyclopropylethyl)amide, the title compound was obtained as a light yellow solid (97% yield). $^1$H NMR (300 MHz, CDCl$_3$) δ 8.02-8.06, 7.96, 7.88, 7.60, 7.48, 7.30, 6.98, 3.72-4.02, 3.54, 3.33, 1.49, 0.74, 0.45, 0.08. MS (ES+) m/z 438 (M+1).

EXAMPLE 14.8

6-[4-(3,3,3-Trifluoro-2-Hydroxy-2-Methylpropionyl) Piperazin-1-Yl]Pyridazine-3-Carboxylic Acid (2-Cyclopropylethyl)Amide Following the procedure of Example 14, making variations only as required to use 3,3,3-trifluoro-2-hydroxy-2-methylpropionic acid in place of 4,4,4-trifluoro-2-methylbutyric acid to react with 6-piperazin-1-yl-pyridazine-3-carboxylic acid (3-methylbutyl)amide, the title compound was obtained as a white solid (55% yield). m.p. 181-183° C. $^1$H NMR (300 MHz, CDCl$_3$) δ 8.07, 7.98, 7.01, 4.86, 3.92-3.81, 3.55, 1.74, 1.51, 0.81-0.68, 0.46, 0.09. $^{13}$C NMR (75 MHz, CDCl$_3$) δ 167.2, 163.1, 160.0, 145.4, 127.1, 126.3, 122.5, 112.5. 76.8-75.6 (q, J=117 Hz, C-19F), 44.6, 39.7, 35.3, 20.5, 8.5, 4.8. MS (ES+) m/z 416 (M+1).

EXAMPLE 15

Synthesis of 6-[4-(2-Trifluoromethylbenzoyl)Piperazin-1-Yl]Pyridazine-3-Carboxylic Acid (2-Cyclopropyl-2-Hydroxyethyl)Amide To a solution of 6-chloropyridazine-3-carboxylic acid (2-cyclopropyl-2-hydroxyethyl)amide (58 mg, 0.24 mmol) in 10 mL of DMF was added 1,8-diazabicylco[5.4.0]undec-7-ene (0.109 g), piperazin-1-yl-(2-trifluoromethylphenyl) methanone (86.7 mg, 0.33 mmol) and Bu$_4$NI (4 mg, 0.01 mmol). The mixture was heated at 80° C. overnight. Water was added and the mixture was extracted with ethyl acetate (2×15 mL). The organic extract was washed with diluted HCl, followed by bicarbonate solution and brine, then dried over Na$_2$SO$_4$ and concentrated. The residue was dissolved in small amount of dichloromethane and purified by column chromatography eluted with ethyl acetate to yield the product as a white solid (35.5 mg, 32% yield). $^1$H NMR (300 MHz, CDCl$_3$) δ 8.24, 8.02, 7.73, 7.58, 7.34, 6.98, 4.04, 3.85, 3.52, 3.33, 3.10, 2.60-2.41, 0.95, 0.52, 0.32. MS (ES+) m/z 464.3 (M+1).

EXAMPLE 15.1

4-Methyl-2-({6-[4-(2-Trifluoromethylbenzoyl)Piperazin-1-Yl]-Pyridazine-3-Carbonyl}Amino)Pentanoic Acid Methyl Ester Following the procedure of Example 15, making variations only as required to use 2-[(6-chloropyridazine-3-carbonyl) amino]-4-methylpentanoic acid methyl ester in place of 6-chloropyridazine-3-carboxylic acid (2-cyclopropyl-2-hydroxyethyl)amide to react with piperazin-1-yl-(2-trifluoromethylphenyl)-methanone, the title compound was obtained as a white solid (36% yield). $^1$H NMR (400 MHz, CDCl$_3$) δ 8.16, 8.04, 7.85, 7.66-7.53, 7.28, 7.00, 4.82-4.77, 4.14-3.68, 3.58-3.51, 1.83-1.60, 1.03-0.95.

EXAMPLE 15.2

6-[4-(2-Trifluoromethylbenzoyl)Piperazin-1-Yl]Pyridazine-3-Carboxylic Acid Cyclopropylmethylamide Following the procedure of Example 15, making variation's only as required to use 6-chloropyridazine-3-carboxylic acid cyclopropylmethylamide in place of 6-chloropyridazine-3-carboxylic acid (2-cyclopropyl-2-hydroxyethyl) amide to react with piperazin-1-yl-(2-trifluoromethylphenyl) methanone, the title compound was obtained as a white solid (31% yield). $^1$H NMR (500 MHz, CDCl$_3$) δ 8.16-7.88, 7.75, 7.68-7.46, 7.18, 7.00, 4.17-3.64, 3.21-3.12, 1.07-1.00, 0.61-0.44, 0.26-0.20.

EXAMPLE 15.3

6-[4-(2-Trifluoromethylbenzoyl)Piperazin-1-Yl]Pyridazine-3-Carboxylic Acid [2-(4-Metoxyphenyl) Ethyl]Amide Following the procedure of Example 15, making variations only as required to use 6-chloropyridazine-3-carboxylic acid [2-(4-metoxyphenyl)ethyl]amide in place of 6-chloropyridazine-3-carboxylic acid (2-cyclopropyl-2-hydroxyethyl) amide to react with piperazin-1-yl-(2-trifluoromethylphenyl) methanone, the title compound was obtained as a white solid (12% yield). $^1$H NMR (400 MHz, CDCl$_3$) δ 8.04, 7.93, 7.74, 7.63, 7.56, 7.36, 7.12, 6.92, 6.81, 4.08-3.46, 3.33, 2.87.

EXAMPLE 15.4

6-[4-(2-Trifluoromethylbenzoyl)-Piperazin-1-Yl] Pyridazine-3-Carboxylic Acid (3-Phenylpropyl) Amide Following the procedure of Example 15, making variations only as required to use 6-chloropyridazine-3-carboxylic acid (3-phenylpropyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (15% yield). $^1$H NMR (500 MHz, CDCl$_3$) δ 8.05, 7.93, 7.74, 7.63, 7.56, 7.39, 7.29-7.13, 6.92, 4.12-3.29, 2.68, 2.02-1.83.

EXAMPLE 15.5

6-[4-(2-Trifluoromethylbenzoyl)Piperazin-1-Yl]Pyridazine-3-Carboxylic Acid [2-(4-Chlorophenoxy)Ethyl]Amide Following the procedure of Example 15, making variations only as required to use 6-chloropyridazine-3-carboxylic acid [2-(4-chlorophenoxy)ethyl]amide in place of 6-chloro-pyridazine-3-carboxylic acid (2-cyclopropyl-2-hydroxyethyl)amide to react with piperazin-1-yl-(2-trifluoromethylphenyl)methanone, the title compound was obtained as a white solid (13% yield). $^1$H NMR (400 MHz, CDCl$_3$) δ 8.27, 8.05, 7.74, 7.64, 7.57, 7.37, 7.25-7.20, 7.00, 6.85-6.82, 4.02-3.32.

EXAMPLE 15.6

6-[4-(2-Trifluoromethylbenzoyl)Piperazin-1-Yl]Pyridazine-3-Carboxylic Acid [2-(4-Fluorophenoxy)Ethyl]Amide Following the procedure of Example 15, making variations only as required to use 6-chloropyridazine-3-carboxylic acid [2-(4-fluorophenoxy)ethyl]amide in place of 6-chloropyridazine-3-carboxylic acid (2-cyclopropyl-2-hydroxyethyl)amide to react with piperazin-1-yl-(2-trifluoromethylphenyl)-methanone, the title compound was obtained as a white solid (49% yield). $^1$H NMR (500 MHz, CDCl$_3$) δ 8.28, 8.05, 7.74, 7.63, 7.56, 7.35, 7.03-6.92, 6.87-6.81, 4.02-3.30.

EXAMPLE 15.7

6-[4-(2-Trifluoromethylbenzoyl)Piperazin-1-Yl]Pyridazine-3-Carboxylic Acid [2-(2,4-Difluorophenyl)Ethyl]Amide Following the procedure of Example 15, making variations only as required to use 6-chloropyridazine-3-carboxylic acid [2-(2,4-difluorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (33% yield). m.p. 179-181° C. $^1$H NMR (400 MHz, CDCl$_3$) δ 8.04, 7.91, 7.75, 7.61, 7.37, 7.30-6.89, 4.09-3.66, 3.38-3.32, 2.88. MS (ES+) m/z 520 (M+1).

EXAMPLE 15.8

6-[4-(2-Trifluoromethylbenzoyl)Piperazin-1-Yl]Pyridazine-3-Carboxylic Acid (3,3-Dimethylbutyl)Amide Following the procedure of Example 15, making variations only as required to use 6-chloropyridazine-3-carboxylic acid (3,3-dimethylbutyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (17% yield). $^1$H NMR (400 MHz, CDCl$_3$) δ 8.05, 7.83-7.72, 7.64, 7.57, 7.38, 6.98, 4.09-3.66, 3.50-3.45, 3.37-3.34, 1.57-1.52, 0.96. MS (ES+) m/z 464.6 (M+1).

EXAMPLE 15.9

6-[4-(2-Trifluoromethylbenzoyl)Piperazin-1-Yl]Pyridazine-3-Carboxylic Acid (2-Phenylcyclopropylmethyl)Amide Following the procedure of Example 15, making variations only as required to use 6-chloropyridazine-3-carboxylic acid (2-phenylcyclopropylmethyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (25% yield). $^1$H NMR (400 MHz, CDCl$_3$) δ 8.09-8.03, 7.76, 7.64, 7.57, 7.36, 7.28-7.21, 7.17-7.12, 7.07-6.96, 4.09-3.32, 1.92-1.86, 1.47-1.38, 1.01-0.96. MS (ES+) m/z 510.4 (M+1).

EXAMPLE 15.10

6-[4-(2-Trifluoromethylbenzoyl)Piperazin-1-Yl]Pyridazine-3-Carboxylic Acid (3-Cyclopropylpropyl)Amide Following the procedure of Example 15, making variations only as required to use 6-chloropyridazine-3-carboxylic acid (3-cyclopropylpropyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (28% yield). $^1$H NMR (400 MHz, CDCl$_3$) δ 8.04, 7.89, 7.73, 7.65, 7.58, 7.38, 6.99, 4.08-3.67, 3.54-3.46, 3.39-3.31, 1.77-1.66, 1.34-1.23, 0.72-0.62, 0.45-0.36, 0.06-0.04. MS (ES+) m/z 462.2 (M+1).

EXAMPLE 15.11

4-[6-(2-Cyclopropylethylcarbamoyl)Pridazin-3-Yl]Piperazine-1-Carboxylic Acid T-Butyl Ester Following the procedure of Example 15, making variations only as required to use 6-chloropyridazine-3-carboxylic acid (2-cyclopropylethyl)amide in place of 6-chloropyridazine-3-carboxylic acid (2-cyclopropyl-2-hydroxyethyl)amide to react with piperazine-1-carboxylic acid t-butyl ester, the title compound was obtained as a white solid (47% yield). $^1$H NMR (400 MHz, CDCl$_3$) δ 8.04-7.95, 6.97, 3.62-3.54, 1.59-1.44, 1.34-1.23, 0.72-0.62, 0.45-0.36, 0.06-0.04. MS (ES+) m/z 376.3 (M+1).

EXAMPLE 15.12

6-[4-(Tetrahydrofuran-2-Carbonyl)Piperazin-1-Yl]Pyridazine-3-Carboxylic Acid (2-Cyclopropylethyl)Amide Following the procedure of Example 15, making variations only as required to use 6-chloropyridazine-3-carboxylic acid (2-cyclopropylethyl)amide in place of 6-chloropyridazine-3-carboxylic acid (2-cyclopropyl-2-hydroxyethyl)amide to react with piperazin-1-yl-(tetrahydrofuran-2-yl)methanone, the title compound was obtained as a white solid (47% yield). $^1$H NMR (400 MHz, CDCl$_3$) δ 8.12-7.88, 6.97, 4.64-4.60, 3.93-3.42, 2.56-2.35, 2.10-1.93, 1.52-1.38, 0.84-0.62, 0.50-0.38, 0.17-0.05. MS (ES+) m/z 374.3 (M+1).

EXAMPLE 15.13

6-[4-(2-Trifluoromethylbenzoyl)Piperazin-1-Yl]Pyridazine-3-Carboxylic Acid [2-(3-Fluorophenyl)Ethyl]Amide Following the procedure of Example 15, making variations only as required to use 6-chloropyridazine-3-carboxylic acid [2-(3-fluorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (71% yield). $^1$H NMR (400 MHz, CDCl$_3$) δ 8.05, 7.93, 7.74, 7.64-7.56, 7.37-7.35, 7.26-7.24, 7.01-6.90, 4.10-4.03, 3.89-3.70, 3.36-3.33, 2.92.

EXAMPLE 15.14

6-[4-(2-Trifluoromethylbenzoyl)Piperazin-1-Yl]Pyridazine-3-Carboxylic Acid [2-(4-Fluorophenyl)Ethyl]Amide Following the procedure of Example 15, making variations only as required to use 6-chloropyridazine-3-carboxylic acid [2-(4-fluorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (59.8% yield). $^1$H NMR (400 MHz, CDCl$_3$) δ 8.05, 7.92, 7.72-7.76, 7.66-7.54, 7.38-7.34, 7.20-7.14, 7.0-6.94, 4.10-4.02, 3.92-3.84, 3.80-3.68, 3.37-3.36, 2.90.

EXAMPLE 15.15

6-[4-(2-Trifluoromethylbenzoyl)Piperazin-1-Yl]Pyridazine-3-Carboxylic Acid [2-(2-Fluorophenyl)Ethyl]Amide Following the procedure of Example 15, making variations only as required to use 6-chloropyridazine-3-carboxylic acid [2-(2-fluorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (70.7% yield). $^1$H NMR (400 MHz, CDCl$_3$) δ 8.04, 7.95, 7.75-7.72, 7.63, 7.55, 7.36, 7.22-7.15, 7.05-6.97, 4.07-4.02, 3.89-3.83, 3.79-3.67, 3.35-3.32, 2.96.

EXAMPLE 15.16

6-[4-(2-Trifluoromethylbenzoyl)Piperazin-1-Yl]Pyridazine-3-Carboxylic Acid [2-(4-Chlorophenyl)Ethyl]Amide Following the procedure of Example 15, making variations only as required to use 6-chloropyridazine-3-carboxylic acid [2-(4-chlorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a light yellow powder (46.5% yield). $^1$H NMR (500 MHz, CDCl$_3$) δ 8.10, 7.95, 7.75, 7.65, 7.58, 7.35, 7.25, 7.15, 7.00, 4.10, 3.95-3.66, 3.38, 2.90.

EXAMPLE 15.17

6-[4-(2-Trifluoromethylbenzoyl)Piperazin-1-Yl]Pyridazine-3-Carboxylic Acid [2-(3-Chlorophenyl)Ethyl]Amide Following the procedure of Example 15, making variations only as required to use 6-chloropyridazine-3-carboxylic acid [2-(3-chlorophenyl)ethyl]amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a light yellow powder (59.6% yield). $^1$H NMR (500 MHz, CDCl$_3$) δ 8.05, 7.94, 7.75, 7.64, 7.57, 7.37, 7.26, 7.24-7.19, 7.12, 7.00, 4.10, 3.95-3.66, 3.38, 2.90.

EXAMPLE 15.18

6-[4-(2-Trifluoromethylbenzoyl)Piperazin-1-Yl]Pyridazine-3-Carboxylic Acid (2-Phenylpropyl)Amide Following the procedure of Example 15, making variations only as required to use 6-chloropyridazine-3-carboxylic acid (2-phenylpropyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (63.2% yield). $^1$H NMR (500 MHz, CDCl$_3$) δ 7.97, 7.80, 7.68, 7.57, 7.50, 7.30, 7.24, 7.20-7.12, 6.92, 3.98, 3.80, 3.74-3.60, 3.53, 3.28, 3.00, 1.28.

EXAMPLE 15.19

6-[4-(2-Trifluoromethylbenzoyl)Piperazin-1-Yl]Pyridazine-3-Carboxylic Acid (2-Biphenyl-4-Yl-Ethyl)Amide Following the procedure of Example 15, making variations only as required to use 6-chloropyridazine-3-carboxylic acid (2-biphenyl-4-yl-ethyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (63.2% yield). $^1$H NMR (500 MHz, CDCl$_3$) δ 8.07, 7.98, 7.76, 7.64, 7.60-7.52, 7.44, 7.38-7.30, 7.00, 4.06, 3.88, 3.82-3.68, 3.36, 2.98.

EXAMPLE 15.20

6-[4-(2-Trifluoromethylbenzoyl)Piperazin-1-Yl]Pyridazine-3-Carboxylic Acid (3-Methylbutyl)Amide Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (63.2% yield). $^1$H NMR (500 MHz, CDCl$_3$) δ 8.05, 7.98, 7.75, 7.64, 7.57, 7.37, 7.00, 4.06, 3.89, 3.82-3.64, 3.49, 3.36, 1.70, 1.50, 0.95.

EXAMPLE 15.21

6-[4-(2-Trifluoromethylbenzoyl)Piperazin-1-Yl]Pyridazine-3-Carboxylic Acid (4-Hydroxybutyl)Amide Following the procedure of Example 15, making variations only as required to use 6-chloropyridazine-3-carboxylic acid (4-hydroxybutyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (30% yield). $^1$H NMR (500 MHz, CDCl$_3$) δ 8.05, 7.98, 7.75, 7.63, 7.57, 7.37, 6.99, 4.06, 3.88, 3.82-3.67, 3.52, 3.36, 1.70.

EXAMPLE 15.22

(R)-6-[4-(2-Trifluoromethylbenzoyl)Piperazin-1-Yl]Pyridazine-3-Carboxylic Acid (2-Hydroxy-2-Phenylethyl)Amide Following the procedure of Example 15, making variations only as required to use (R)-6-chloropyridazine-3-carboxylic acid (2-hydroxy-2-phenylethyl)amide in place of 6-chloropyridazine-3-carboxylic acid (2-cyclopropyl-2-hydroxyethyl) amide to react with piperazin-1-yl-(2-trifluoromethylphenyl)methanone, the title compound was obtained as a white powder (64.5% yield). $^1$H NMR (500 MHz, CDCl$_3$) δ 8.28, 8.05, 7.76, 7.64, 7.58, 7.44-7.32, 7.29, 7.00, 4.96, 4.08, 3.92-3.68, 3.61, 3.36.

EXAMPLE 15.23

(S)-6-[4-(2-Trifluoromethylbenzoyl)Piperazin-1-Yl]Pyridazine-3-Carboxylic Acid (2-Hydroxy-2-Phenylethyl)Amide Following the procedure of Example 15, making variations only as required to use (S)-6-chloropyridazine-3-carboxylic acid (2-hydroxy-2-phenylethyl)amide in place of 6-chloropyridazine-3-carboxylic acid (2-cyclopropyl-2-hydroxyethyl) amide to react with piperazin-1-yl-(2-trifluoromethylphenyl)methanone, the title compound was obtained as a white powder (64.5% yield). $^1$H NMR (500 MHz, CDCl$_3$) δ 8.28, 8.05, 7.76, 7.64, 7.58, 7.44-7.32, 7.29, 7.00, 4.96, 4.08, 3.92-3.68, 3.61, 3.36. MS (ES+) m/z 500 (M+1).

EXAMPLE 15.24

4-({6-[4-(2-Trifluoromethylbenzoyl)Piperazin-1-Yl]Pyridazine-3-Carbonyl}Amino)Butyric Acid Ethyl Ester Following the procedure of Example 15, making variations only as required to use 2-[(6-chloropyridazine-3-carbonyl)amino]butyric acid ethyl ester in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (37.8% yield). $^1$H NMR (500 MHz, CDCl$_3$) δ 8.05, 7.96, 7.75, 7.65, 7.57, 7.37, 7.00, 4.16-4.04, 3.92-3.70, 3.56, 3.36, 2.40, 1.25. MS (ES+) m/z 494 (M+1).

EXAMPLE 15.25

6-[4-(2-Trifluoromethylbenzoyl)Piperazin-1-Yl]Pyridazine-3-Carboxylic Acid (3-Hydroxy-4,4-Dimethylpentyl)Amide Following the procedure of Example 15, making variations only as required to use 6-chloropyridazine-3-carboxylic acid (3-hydroxy-4,4-dimethylpentyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (39% yield). $^1$H NMR (500 MHz, CDCl$_3$) δ 8.18, 8.05, 7.74, 7.63, 7.56, 7.36, 6.99, 4.05, 3.92-3.67, 3.45-3.32, 3.26, 1.76, 1.55, 0.88. MS (ES+) m/z 494 (M+1).

EXAMPLE 15.26

6-[4-(2-Trifluoromethylbenzoyl)Piperazin-1-Yl]Pyridazine-3-Carboxylic Acid (3-Hydroxy-3-Methylbutyl)Amide Following the procedure of Example 15, making variations only as required to use 6-chloropyridazine-3-carboxylic acid (3-hydroxy-3-methylbutyl)amide in place of 6-chloropyridazine-3-carboxylic acid (2-cyclopropyl-2-hydroxyethyl) amide to react with piperazin-1-yl-(2-trifluoromethylphenyl) methanone, the title compound was obtained as a white powder (46.4% yield). $^1$H NMR (500 MHz, CDCl$_3$) δ 8.30, 8.05, 7.75, 7.65, 7.57, 7.37, 6.98, 4.06, 3.88, 3.81-3.69, 3.64, 3.40-3.32, 1.80, 1.64, 1.30. MS (ES+) m/z 466 (M+1).

EXAMPLE 15.27

6-[4-(2-Trifluoromethylbenzoyl)Piperazin-1-Yl]Pyridazine-3-Carboxylic Acid (2-Ethoxyethyl)Amide Following the procedure of Example 15, making variations only as required to use 6-chloropyridazine-3-carboxylic acid (2-ethoxyethyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (24.8% yield). $^1$H NMR (500 MHz, CDCl$_3$) δ 8.18, 8.07, 7.76, 7.65, 7.58, 7.38, 7.00, 4.07, 3.90, 3.83-3.65, 3.60, 3.52, 3.36, 1.20. MS (ES+) m/z 452 (M+1).

EXAMPLE 15.28

6-[4-(2-Trifluoromethylbenzoyl)Piperazin-1-Yl]Pyridazine-3-Carboxylic Acid Pentylamide Following the procedure of Example 15, making variations only as required to use 6-chloropyridazine-3-carboxylic acid pentylamide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (94% yield). m.p. 123-125° C. $^1$H NMR (300 MHz, CDCl$_3$) δ 8.03, 7.85, 7.62, 7.54, 7.35, 6.97, 4.06-3.99, 3.91-3.69, 3.44, 3.33, 1.62-1.55, 1.37-1.33, 0.95-0.81. $^{13}$C NMR (75 MHz, CDCl$_3$) δ 167.6, 162.9, 160.0, 145.5, 132.4, 129.5, 127.2, 127.1, 126.9-127.8, 112.5, 77.2, 46.4, 44.6, 44.4, 41.3, 39.4, 29.3, 29.1, 22.4, 14.0. MS (ES+) m/z 450.2 (M+1), 472.2 (M+Na).

EXAMPLE 15.29

6-[4-(2-Trifluoromethylbenzoyl)Piperazin-1-Yl]Pyridazine-3-Carboxylic Acid (2-Hydroxy-3,3-DIMETHYLBUTYL)AMIDE Following the procedure of Example 15, making variations only as required to use 6-chloropyridazine-3-carboxylic acid (2-hydroxy-3,3-dimethylbutyl)amide in place of 6-chloropyridazine-3-carboxylic acid (2-cyclopropyl-2-hydroxyethyl) amide to react with piperazin-1-yl-(2-trifluoromethylphenyl) methanone, the title compound was obtained as a brown solid (75% yield). m.p. 236-240° C. $^1$H NMR (300 MHZ, CDCl$_3$) δ 7.90, 7.83-7.79, 7.75-7.73, 7.69-7.65, 7.54-7.52, 7.30, 4.29, 3.91-3.73, 3.43-3.32, 3.20-3.11, 2.81, 2.77, 0.95. MS (ES+) m/z 480 (M+1).

EXAMPLE 15.30

6-[4-(5-Fluoro-2-Trifluoromethylbenzoyl)Piperazin-1-Yl]Pyridazine-3-Carboxylic Acid (2-Hydroxy-3,3-Dimethylbutyl)Amide Following the procedure of Example 15, making variations only as required to use 6-chloropyridazine-3-carboxylic acid (2-hydroxy-3,3-dimethylbutyl)amide in place of 6-chloropyridazine-3-carboxylic acid (2-cyclopropyl-2-hydroxyethyl) amide to react with piperazin-1-yl-(5-fluoro-2-trifluoromethylphenyl)methanone, the title compound was obtained as a brown solid (51% yield). m.p. 186-189° C. $^1$H NMR (300 MHz, CDCl$_3$) δ 8.20, 8.04, 7.75, 7.22, 7.07, 6.98, 4.06-3.98, 3.91-3.71, 3.47-3.23, 2.45, 0.96. $^{13}$C NMR (75 MHz, CDCl$_3$) δ 166.3, 164.1, 160.1, 160.0, 130.1, 127.2, 116.9, 116.6, 115.0, 114.7, 112.4, 79.4, 46.4, 44.5, 44.3, 41.9, 41.3, 34.4, 25.7. MS (ES+) m/z 498 (M+1).

EXAMPLE 15.31

6-[4-(2-Methylcyclopropanecarbonyl)Piperazin-1-Yl]Pyridazine-3-Carboxylic Acid (2-Cyclopropylethyl)Amide Following the procedure of Example 15, making variations only as required to use 6-chloropyridazine-3-carboxylic acid (2-cyclopropylethyl)amide in place of 6-chloropyridazine-3-carboxylic acid (2-cyclopropyl-2-hydroxyethyl)amide to react with piperazin-1-yl-(2-methylcyclopropyl)methanone, the title compound was obtained as a white solid (88% yield). $^{13}$C NMR (75 MHz, CDCl$_3$) δ 177.1, 163.5, 159.5, 144.9, 131.3, 126.4, 115.1, 49.7, 45.2, 39.5, 37.5, 37.2, 35.3, 34.6, 29.9, 28.5, 26.5, 23.4, 8.6, 4.2. MS (ES+) m/z 360 (M+1).

EXAMPLE 15.32

6-[4-(5-Fluoro-2-Trifluoromethylbenzoyl)Piperazin-1-Yl]Pyridazine-3-Carboxylic Acid Pentylamide Following the procedure of Example 15, making variations only as required to use 6-chloropyridazine-3-carboxylic acid pentylamide in place of 6-chloropyridazine-3-carboxylic acid (2-cyclopropyl-2-hydroxyethyl)amide to react with piperazin-1-yl-(5-fluoro-2-trifluoromethylphenyl)methanone, the title compound was obtained as a white solid (31% yield). m.p. 162-164° C. $^1$H NMR (300 MHz, CDCl$_3$) δ 8.05, 7.87, 7.24, 7.07, 6.99, 4.08-3.99, 3.90-3.66, 3.45, 3.35, 1.65-1.55, 1.37-1.30. $^{13}$C NMR (75 MHz, CDCl$_3$) δ 166.1, 162.9, 160.0, 145.7, 129.7, 127.2, 116.9, 116.6, 115.0, 114.7, 112.6, 77.2, 46.4, 44.6, 44.4, 41.3, 39.4, 29.3, 29.1, 22.4, 14.0.

EXAMPLE 15.33

6-[4-(2-Trifluoromethylbenzoyl)Piperazin-1-Yl]Pyridazine-3-Carboxylic Acid (4-Methylpentyl)Amide Following the procedure of Example 15, making variations only as required to use 6-chloropyridazine-3-carboxylic acid (4-methylpentyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (36% yield). m.p. 43-45° C. $^1$H NMR (300 MHz, CDCl$_3$) δ 7.71, 7.66-7.52, 7.34, 6.96, 4.06-3.98, 3.87-3.68, 3.63, 3.53, 3.19, 3.25, 3.09, 1.65-1.58, 1.36-1.33, 1.26-1.12, 0.85. $^{13}$C NMR (75 MHz, CDCl$_3$) δ167.6, 166.9, 166.2, 159.0, 158.9, 149.5, 149.4, 134.4, 132.4, 129.5, 129.2, 127.2, 126.9, 126.8, 112.6, 112.5, 51.4, 48.8, 46.4, 44.7, 44.4, 41.3, 37.8, 34.8, 34.0, 29.7, 29.0, 28.7, 27.1, 26.7, 22.5, 22.3, 14.0, 13.9. MS (ES+) m/z 464.2 (M+1), 486.2 (M+Na).

EXAMPLE 15.34

6-[4-(5-Fluoro-2-Trifluoromethylbenzoyl)Piperazin-1-Yl]Pyridazine-3-Carboxylic Acid (3-Methylbutyl)Amide Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-yl-(5-fluoro-2-trifluoromethylphenyl) methanone, the title compound was obtained as a white powder (28.3% yield). $^1$H NMR (400 MHz, CDCl$_3$) δ 8.05, 7.86, 7.78-7.75, 7.28-7.22, 7.12-7.08, 7.02, 4.08-4.01, 3.91-3.86, 3.82-3.68, 3.55-3.46, 3.38, 1.73-1.65, 1.56-1.48, 0.94.

EXAMPLE 15.35

6-[4-(4-Fluoro-2-Trifluoromethylbenzoyl)Piperazin-1-Yl]Pyridazine-3-Carboxylic Acid (3-Methylbutyl)Amide Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-yl-(4-fluoro-2-trifluoromethylphenyl) methanone, the title compound was obtained as a white powder (63.8% yield). $^1$H NMR (400 MHz, CDCl$_3$) δ 8.08, 7.85, 7.48-7.46, 7.41-7.32, 7.02, 4.08-4.05, 3.95-3.88, 3.80-3.68, 3.52-3.45, 3.35, 1.73-1.68, 1.51, 0.94.

EXAMPLE 15.36

6-[4-(2-Fluoro-6-Trifluoromethylbenzoyl)Piperazin-1-Yl]Pyridazine-3-Carboxylic Acid (3-Methylbutyl)Amide Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-yl-(6-fluoro-2-trifluoromethylphenyl) methanone, the title compound was obtained as a white powder (16.8% yield). $^1$H NMR (400 MHz, CDCl$_3$) δ 8.06, 7.85, 7.57-7.55, 7.39-7.36, 7.01, 4.04-3.94, 3.86-3.79, 3.49, 3.44-3.36, 1.73-1.68, 1.52, 0.94.

EXAMPLE 15.37

6-[4-(2,6-Difluorobenzoyl)Piperazin-1-Yl]Pyridazine-3-Carboxylic Acid (3-Methylbutyl)Amide Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-yl-(2,6-difluorophenyl)methanone, the title compound was obtained as a white powder (42.2% yield). $^1$H NMR (400 MHz, CDCl$_3$) δ 8.07, 7.85, 7.44-7.38, 7.03-6.97, 4.0-3.99, 3.86-3.83, 3.52-3.48, 1.73-1.67, 1.51, 0.94.

EXAMPLE 15.38

6-[4-(2,2,3,3-Tetramethylcyclopropanecarbonyl) Piperazin-1-Yl]-Pyridazine-3-Carboxylic Acid (2-Cyclopropylethyl)Amide Following the procedure of Example 15, making variations only as required to use 6-chloropyridazine-3-carboxylic acid (2-cyclopropylethyl)amide in place of 6-chloropyridazine-3-carboxylic acid (2-cyclopropyl-2-hydroxyethyl)amide to react with piperazin-1-yl-(2,2,3,3-tetramethylcyclopropyl)methanone, the title compound was obtained as a white solid (35% yield). $^1$H NMR (400 MHz, CDCl$_3$) δ 8.07, 8.01, 7.01, 3.91-3.89, 3.81-3.65, 3.57, 1.21, 1.19, 0.79-0.072, 0.49-0.46, 0.11-0.10. MS (ES+) m/z 400 (M+1).

EXAMPLE 15.39

6-[4-(2-Trifluoromethylbenzoyl)Piperazin-1-Yl]Pyridazine-3-Carboxylic Acid (2-Methylcyclopropylmethyl)Amide Following the procedure of Example 15, making variations only as required to use 6-chloropyridazine-3-carboxylic acid (2-methylcyclopropylmethyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white solid (26% yield). $^1$H NMR (500 MHz, CDCl$_3$) δ 8.06, 7.96, 7.75, 7.65, 7.58, 7.38, 7.01, 4.04-4.10, 3.86-3.93, 3.69-3.83, 3.25-3.42, 1.12, 1.05, 0.71-0.80, 0.64-0.72, 0.39-0.45, 0.25-0.30. MS (ES+) m/z 448 (M+1).

EXAMPLE 15.40

4-[6-(3-Methylbutylcarbamoyl)Pyridazin-3-Yl]Piperazine-1-Carboxylic Acid T-Butyl Ester Following the procedure of Example 15, making variations only as required to use 6-chloropyridazine-3-carboxylic acid (3-methylbutyl)amide in place of 6-chloropyridazine-3-carboxylic acid (2-cyclopropyl-2-hydroxyethyl)amide to react with piperazin-1-carboxylic acid t-butyl ester, the title compound was obtained as a white solid (83% yield). $^1$H NMR (500 MHz, CDCl$_3$) δ 8.03, 7.86, 6.97, 3.75, 3.56-3.63, 3.49, 1.65-1.76, 1.52, 0.94. MS (ES+) m/z 378 (M+1).

EXAMPLE 15.41

6-[4-(2-Trifluoromethylbenzoyl)Piperazin-1-Yl]Pyridazine-3-Carboxylic Acid (2-Cyclobutylethyl) Amide Following the procedure of Example 15, making variations only as required to use 6-chloropyridazine-3-carboxylic acid (2-cyclobutylethyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (47% yield). $^1$H NMR (300 MHz, CDCl$_3$) δ 8.02, 7.74, 7.73, 7.57, 7.35, 6.98, 4.03, 3.89-3.66, 3.40-3.31, 2.36, 2.09-2.00, 1.92-1.57. $^{13}$C NMR (75 MHz, CDCl$_3$) δ 167.6, 134.3, 132.4, 129.5, 127.2, 127.0, 126.9, 126.8, 126.7, 125.5, 121.8, 112.6, 46.4, 44.6, 44.5, 41.3, 37.6, 36.5, 33.7, 28.3, 18.6. MS (ES+) m/z 462.3 (M+1).

EXAMPLE 15.42

6-[4-(2-Trifluoromethylbenzoyl)Piperazin-1-Yl]Pyridazine-3-Carboxylic Acid Hexylamide Following the procedure of Example 15, making variations only as required to use 6-chloropyridazine-3-carboxylic acid hexylamide in place of 6-chloropyridazine-3-carboxylic acid (2-cyclopropyl-2-hydroxyethyl)amide to react with piperazin-1-yl-(2-trifluoromethyl-phenyl)methanone, the title compound was obtained as a white powder (35% yield). $^1$H NMR (300 MHz, CDCl$_3$) δ 8.02, 7.85, 7.72, 7.56, 7.34, 6.97, 4.00, 3.90-3.64, 3.48-3.28, 1.58, 1.29, 0.85. $^{13}$C NMR (75 MHz, CDCl$_3$) 6167.6, 162.9, 160.0, 145.5, 134.3, 132.8, 129.5, 127.6, 127.2, 126.9, 125.4, 46.4, 44.6, 44.4, 41.3, 39.4, 31.5, 29.5, 26.6, 22.6, 14.0. MS (ES+) m/z (%) 464 (M+1).

EXAMPLE 15.43

6-[4-(2-Trifluoromethylbenzoyl)Piperazin-1-Yl]Pyridazine-3-Carboxylic Acid (3-Cyclobutylpropyl) Amide Following the procedure of Example 15, making variations only as required to use 6-chloropyridazine-3-carboxylic acid (3-cyclobutylpropyl)amide in place of 6-chloropyridazine-3-carboxylic acid (2-cyclopropyl-2-hydroxyethyl)amide to react with piperazin-1-yl-(2-trifluoromethylphenyl)methanone, the title compound was obtained as a white powder (28% yield). $^1$H NMR (300 MHz, CDCl$_3$) δ 8.03, 7.85, 7.73, 7.57, 7.34, 6.99, 4.05, 3.89-3.65, 3.45, 3.33, 2.27, 1.99, 1.76, 1.58-1.39. $^{13}$C NMR (75 MHz, CDCl$_3$) δ 167.6, 162.8, 159.9, 145.4, 134.2, 132.4, 129.5, 127.2, 126.9, 126.7, 112.7, 46.4, 44.6, 44.5, 41.2, 39.4, 35.7, 34.1, 28.3, 27.2, 18.4. MS (ES+) m/z 475.9 (M+1).

EXAMPLE 15.44

6-[4-(2-Trifluoromethylbenzoyl)Piperazin-1-Yl]Pyridazine-3-Carboxylic Acid Heptylamide Following the procedure of Example 15, making variations only as required to use 6-chloropyridazine-3-carboxylic acid heptylamide in place of 6-chloropyridazine-3-carboxylic acid (2-cyclopropyl-2-hydroxyethyl)amide to react with piperazin-1-yl-(2-trifluoromethyl-phenyl)methanone, the title compound was obtained as a white powder (41% yield). $^1$H NMR (300 MHz, CDCl$_3$) δ 8.05, 7.85, 7.72, 7.58, 7.34, 6.98, 4.03, 3.94-3.64, 3.47-3.28, 1.58, 1.32-1.25, 0.84. $^{13}$C NMR (75 MHz, CDCl$_3$) δ 167.6, 162.9, 160.0, 145.5, 134.3, 132.4, 129.5, 126.9, 126.3, 125.4, 121.8, 112.6, 46.4, 44.5, 41.3, 39.4, 31.7, 29.6, 29.0, 26.9, 22.6, 14.1. MS (ES+) m/z 478.2 (M+1).

EXAMPLE 15.45

6-[4-(2-Trifluoromethylbenzoyl)Piperazin-1-Yl]Pyridazine-3-Carboxylic Acid (4-Cyclopropylbutyl) Amide Following the procedure of Example 15, making variations only as required to use 6-chloropyridazine-3-carboxylic acid (4-cyclopropylbutyl)amide in place of 6-chloropyridazine-3-carboxylic acid (3-cyclobutylpopyl)amide to react with piperazin-1-yl-(2-trifluoromethyl-phenyl)methanone, the title compound was obtained as a white powder (21% yield). $^1$H NMR (300 MHz, CDCl$_3$) δ 8.03, 7.86, 7.72, 7.58, 7.34, 6.98, 4.05, 3.89-3.62, 3.48-3.31, 1.64-1.41, 1.20, 0.60, 0.39-0.30, −0.04. $^{13}$C NMR (75 MHz, CDCl$_3$) δ 167.6, 162.9, 160.0, 145.4, 134.3, 132.4, 129.5, 127.2, 126.9, 126.7, 125.4, 121.8, 112.6, 46.4, 44.6, 44.4, 41.2, 39.5, 34.4, 29.4, 27.0, 10.7, 4.4. MS (ES+) m/z 476.1 (M+1).

EXAMPLE 16

Synthesis of 4-Methyl-2-({6-[4-(2-Trifluoromethylbenzoyl)Piperazin-1-Yl]Pyridazine-3-Carbonyl}Amino)Pentanoic Acid Lithium hydroxide monohydride (25 mg, 0.595 mmol) was added to a solution of 4-methyl-2-({6-[4-(2-trifluoromethylbenzoyl)piperazin-1-yl]pyridazine-3-carbonyl}-amino)pentanoic acid methyl ester (130 mg, 0.256 mmol) in tetrahydrofuran (3 mL) and water (1.5 mL), the reaction mixture was stirred at ambient temperature for 3 hours, THF was removed by evaporation, the residue was adjusted with 5% citric acid to pH about 6, and diluted with ethyl acetate, washed with water and brine, dried (Na$_2$SO$_4$) and concentrated to afford 4-methyl-2-({6-[4-(2-trifluoromethylbenzoyl)piperazin-1-yl]pyridazine-3-carbonyl}amino)pentanoic acid (94 mg, 74%). $^1$H NMR (400 MHz, CDCl$_3$) δ 8.17, 8.02, 7.78, 7.66-7.53, 7.38, 6.99, 6.72, 4.88-4.73, 4.25-3.60, 3.44-3.21, 1.79-1.06, 1.33-1.19, 1.03, 0.99.

EXAMPLE 17

Synthesis of 6-{4-[1-(2-Trifluoromethylphenyl)Ethyl]Piperazin-1-Yl}-Pyridazine-3-Carboxylic Acid (2-Cyclopropylethyl)Amide Hydrochloride Titanium isopropoxide (0.6 mL, 2.0 mmol) was added to a solution of 6-piperazin-1-yl-pyridazine-3-carboxylic acid 2-(cyclopropylethyl)amide (282 mg, 1.02 mmol) and 2-(trifluoromethyl)acetophenone (0.23 mL, 1.53 mmol) in THF (3 mL). The resulting mixture was stirred at ambient temperature for 4 hours. Sodium cyanoborohydride (130 mg, 1.96 mmol) was added, and stirring was continued for another 13 hours. Aqueous sodium hydroxide (2.0 mL, 1.0 M) was added. After stirred for 5 minutes at ambient temperature, the reaction mixture was diluted with ethyl acetate (50 mL), and then washed with water and brine. The organic layer was dried over anhydrous Na$_2$SO$_4$ and concentrated. Purification via flash chromatography afforded 6-{4-[1-(2-trifluoromethylphenyl)ethyl]piperazin-1-yl}-pyridazine-3-carboxylic acid (2-cyclopropylethyl)amide (126 mg). This product was dissolved in CH$_2$Cl$_2$ (2 mL) and HCl in ether (7 M, 0.2 mL, 1.4 mmol) was then added. This mixture was kept at ambient temperature for 2 hours. The white precipitate was collected by filtration and washed with ether and dried in vacuo to yield the title compound as a white solid (104 mg, 21% yield). m.p. 158-163° C. $^1$H NMR (300 MHz, DMSO-d$_6$) δ 12.10, 8.81, 8.67, 7.90-7.81, 7.64, 7.40, 4.70-2.85, 1.69, 1.38, 0.72-0.58, 0.40-0.32, 0.023-0.02. MS (ES+) m/z 374.3 (M+1-HCl).

EXAMPLE 18

Synthesis of 6-[4-(2-Trifluoromethylbenzoyl)Piperazin-1-Yl]Pyridazine-3-Carboxylic Acid (2-Oxo-2-Phenylethyl)Amide To a solution of 6-[4-(2-trifluoromethylbenzoyl)piperazin-1-yl]pyridazine-3-carboxylic acid (2-hydroxy-2-phenylethyl)amide (0.517 g, 1.03 mmol) in dichloromethane (10 mL), 1,1,1-triacetoxy-1,1-dihydro-1,2-benziodoxol-3(1H)-one (0.53 g) was added in one portion under stirring in a cold water bath. After stirred in a cold water bath for 15 minutes and then at ambient temperature for 2 hours, the reaction mixture was diluted with diethyl ether (20 mL). The mixture was poured into a solution of sodium thiosulfate (1.176 g, 7.44 mmol) in saturated aqueous sodium biocarbonate (29 mL). The mixture was extracted with ethyl acetate (100 mL). The organic layer was washed with saturated aqueous NaHCO$_3$ (2×15 mL) and water (2×15 mL). The combined aqueous washes were then extracted with ethyl acetate (2×80 mL). The combined organic phases were dried over Na$_2$SO$_4$ and filtered, the solvent was then removed in vacuo. The crude product was purified by column chromatography, which was sequentially eluted with hexane:ethyl acetate (1:1), hexane:ethyl acetate (1:2) and pure ethyl acetate. The product was obtained as a white powder (0.261 g, 51% yield). m.p. 196-198° C. $^1$H NMR (300 MHz, CDCl$_3$) δ 8.72, 7.97-8.06, 7.74, 7.47-7.66, 7.36, 6.99, 4.96, 4.02-4.11, 3.70-3.92, 3.27-3.42. $^{13}$C NMR (CDCl$_3$) δ 193.4, 167.7, 163.4, 160.0, 145.1, 134.6, 134.2, 134.0, 132.4, 129.6, 128.9, 128.0, 127.2, 126.9, 126.8, 112.3, 46.4, 44.7, 44.4, 41.3. MS (ES+) m/z 498 (M+1).

EXAMPLE 19

Synthesis of Acetic Acid 1-Phenyl-2-({6-[4-(2-Trifluoromethyl-Benzoyl)Piperazin-1-Yl]Pyridazine-3-Carbonyl}Amino)Ethyl Ester To a solution of 6-[4-(2-trifluoromethylbenzoyl)piperazin-1-yl]pyridazine-3-carboxylic acid (2-hydroxy-2-phenylethyl)amide (50 mg, 0.1 mmol) in chloroform (2 mL), acetic anhydride (0.25 mL), triethylamine (0.25 mL) and 4-dimethylaminopyridine (18 mg) were added. After stirred at ambient temperature for 6 hours, the reaction mixture was diluted with ethyl acetate (100 mL), washed with water (3×10 mL) and dried over Na$_2$SO$_4$. The crude product obtained after removal of the solvent was purified by column chromatography eluted sequentially with hexane:ethyl acetate=1:1 and 1:2 to give a white powder (49.6 mg, 91.5% yield). $^1$H NMR (500 MHz, CDCl$_3$) δ 8.10, 8.04, 7.75, 7.65, 7.57, 7.40-7.28, 7.00, 5.92, 4.07, 3.98, 3.90, 3.82-3.68, 3.36, 2.10. MS (ES+) m/z 508 (M+1).

EXAMPLE 19.1

Acetic Acid 1,1-Dimethyl-3-({6-[4-(2-Trifluoromethylbenzoyl)Piperazin-1-Yl]-Pyridazine-3-Carbonyl}Amino)Propyl Ester Following the procedure of Example 19, making variations only as required to use 6-[4-(2-trifluoromethylbenzoyl)piperazin-1-yl]pyridazine-3-carboxylic acid (3-hydroxy-3-methylbutyl)amide in place of 6-[4-(2-trifluoromethylbenzoyl)piperazin-1-yl]pyridazine-3-carboxylic acid (2-hydroxy-2-phenylethyl)amide to react with acetic anhydride, the title compound was obtained as a white powder (80% yield). $^1$H NMR (500 MHz, CDCl$_3$) δ 8.05, 8.01, 7.75, 7.65, 7.57, 7.37, 6.99, 4.06, 3.88, 3.81-3.67, 3.58, 3.36, 2.06, 2.01, 1.52. MS (ES+) m/z 508 (M+1).

EXAMPLE 20

Synthesis of 6-[4-(2-Trifluoromethylbenzoyl)Piperazin-1-Yl]Pyridazine-3-Carboxylic Acid (2-Methoxy-3,3-Dimethylbutyl)Amide To a solution of 6-[4-(2-trifluoromethylbenzoyl)piperazin-1-yl]pyridazine-3-carboxylic acid (2-hydroxy-3,3-dimethylbutyl)amide (81.6 mg, 0.17 mmol) in THF (1.0 mL) was added sodium hydride (5.0 mg, 0.19 mmol), followed by methyl iodide (15 mL, 0.26 mmol). The reaction mixture was stirred at ambient temperature for 16 hours and then the solvent was removed. The gummy material was diluted with dichloromethane (5 mL), washed with water (2×2 mL), dried over MgSO$_4$ and filtered off the solid. After the solvent was concentrated into dryness, the crude material was subjected to column chromatography eluted sequentially with ethyl acetate:hexane (1:1) and ethyl acetate to obtain 25.3 mg (30%) of the product as solid. m.p. 65-68° C. $^1$H NMR (300 MHz, CDCl$_3$) δ 7.73-7.69, 7.62, 7.53, 7.33, 6.98-6.93, 4.18-3.59, 3.48, 3.41, 3.37-3.26, 3.18, 3.03-2.98, 1.76, 0.98, 0.75. $^{13}$C NMR (75 MHz, CDCl$_3$) δ 167.6, 166.4, 158.9, 149.8, 149.3, 134.3, 132.4, 129.5, 129.4, 129.3, 129.1, 127.2, 126.9-126.7, 112.7, 88.1, 61.7, 61.4, 52.7, 52.0, 46.4, 44.7, 44.6, 44.5, 44.4, 41.3, 41.2, 40.5, 35.8, 35.3, 35.0, 26.0, 25.9, 25.7. MS (ES+) m/z 508 (M+1).

EXAMPLE 21

Synthesis of 6-[3,5-Dimethyl-4-(2-Trifluoromethylbenzoyl)Piperazin-1-Yl]Pyridazine-3-Carboxylic Acid (2-Cyclopropylethyl)Amide To a solution of 6-(3,5-dimethylpiperazin-1-yl)pyridazine-3-carboxylic acid (2-cyclopropylethyl)amide (0.40 g, 1.33 mmol) in dichloromethane (15 mL) was added diisopropyl ethylamine (0.34 g, 0.46 mL, 2.66 mmol) followed by 2-trifluoromethylbenzoyl chloride (0.31 g, 0.22 mL, 1.46 mmol) at ambient temperature. The reaction solution was stirred for 16 hours and poured into cold water (10 mL). The organic layer was extracted with dichloromethane (50 mL) and washed with saturated solution of NaHCO$_3$ (2×10 mL) and dried over MgSO$_4$. After filtration, the filtrate was concentrated in vacuo. The crude material was purified by column chromatography eluting with ethyl acetate (100%) to obtain 0.18 g of colorless solid (28% yield). $^1$H NMR (300 MHz, CDCl$_3$) δ 8.03-7.91, 7.70, 7.63-7.49, 7.32, 6.99-6.95, 5.00, 4.39-4.22, 3.64, 3.55-3.47, 3.39-3.17, 1.51-1.38, 1.24-1.14, 0.76-0.67, 0.42, 0.05. $^{13}$C NMR (75 MHz, CDCl$_3$) δ 168.0, 163.0, 160.9, 144.9, 132.3, 131.9, 129.4, 129.3, 127.2, 127.0, 126.8, 111.5, 50.4, 49.1, 48.7, 48.5, 48.2, 45.5, 45.3, 39.6, 34.6, 20.2, 19.5, 8.6, 4.2.

EXAMPLE 22

Synthesis of 6-[2,5-Dimethyl-4-(2-Trifluoromethylbenzoyl)Piperazin-1-Yl]Pyridazine-3-Carboxylic Acid Pentylamide To a mixture of 6-chloropyridazine-3-carboxylic acid pentylamide (304 mg, 1.00 mmol) in 2-propanol (12 mL) was added 2,5-dimethylpiperazine (1.37 g, 12.0 mmol). The reaction mixture was refluxed for 2 days. Another 0.25 g of 2,5-dimethylpiperazine and 1.0 mL of triethylamine were added to the reaction mixture and heating was continued for another 24 hours. After the reaction mixture was cooled to ambient temperature and the solvent was removed by rotary evaporator. To the dichloromethane solution of the crude material (20 mL) was added the solution of 2-trifluoromethylbenzoyl chloride (0.63 g, 3.00 mmol) in dichloromethane (20 mL) and the reaction mixture was stirred at ambient temperature for 16 hours. The organic layer was diluted with dichloromethane (50 mL) and then washed with 10% HCl, dried over MgSO$_4$. After filtration, the filtrate was concentrated in vacuo. The crude material was purified by column chromatography eluting with ethyl acetate (100%) to afford 300 mg (31% yield) of the product as a colourless solid. $^1$H NMR (300 MHz, CDCl$_3$) δ 7.74-7.43, 7.36-7.24, 5.17-5.04, 4.91-4.79, 4.52, 4.52, 3.68-3.57, 3.54-3.44, 3.39-3.11, 2.93, 2.85-2.71, 1.36-1.31, 1.27-1.15, 1.23-1.05.

EXAMPLE 23

Synthesis of 2-{4-[6-(2-Cyclopropylethylcarbamoyl)Pyridazin-3-Yl]Piperazine-1-Carbonyl}Benzoic Acid Lithium hydroxide monohydrate (0.066 g, 1.57 mmol) was added to a solution of 2-{4-[6-(2-cyclopropylethylcarbamoyl)pyridazin-3-yl]piperazine-1-carbonyl}benzoic acid methyl ester (0.230 g) in tetrahydrofuran (10 mL) and water (5 mL) stirred at ambient temperature overnight. THF was removed in vacuo, the residue was dissolved in ethyl acetate (100 mL), neutralized by addition of 5% HCl solution, washed with brine, dried over anhydrous Na$_2$SO$_4$ and concentrated. The residue was recrystallized from dichloromethane and hexanes to yield 0.107 g of the title compound (42% yield).

$^1$H NMR (300 MHz, CDCl$_3$) δ 8.67, 9.07-7.87, 7.54, 7.41, 7.26-7.24, 6.95, 4.12-3.27, 1.55-1.40, 0.77-0.64, 0.50-0.34, 0.13-0.01; $^{13}$C NMR (75 MHz, CDCl$_3$) δ 170.7, 168.2, 163.2, 159.9, 145.0, 137.7, 133.1, 131.2, 129.2, 127.9, 127.2, 126.6, 112.6, 46.2, 44.1, 41.4, 39.7, 34.4, 8.6, 4.2; MS (ES+) m/z 424.2 (M+1).

EXAMPLE 24

Synthesis of 6-[4-(2-Trifluoromethylbenzoyl)Piperazin-1-Yl]Pyridazine-3-Carboxylic Acid 2,2-(Dimethylcyclopropylmethyl)Amide To a solution of 6-[4-(2-trifluoromethylbenzoyl)piperazin-1-yl]pyridazine-3-carboxylic acid (1.00 mmol) in dichloromethane (20 mL) was added diisopropylethylamine (0.8 mL, 4.60 mmol), 1-hydroxybenzotriazole hydrate (0.203 g, 1.50 mmol) and 1-(3-dimethylamino-propyl)-3-ethylcarbodiimide hydrochloride (0.384 mg, 2.00 mmol). The resulting mixture was stirred for 15 min, then 2,2-(dimethylcyclopropyl)methylamine (0.149 mg, 1.5 mmol) was added. The stirring was continued for another 24 h. The reaction mixture was diluted with dichloromethane (100 mL), washed sequentially with water and brine, then dried over anhydrous $Na_2SO_4$ and concentrated. Purification by flash chromatography over silica gel (ethyl acetate) and recrystallization from ethyl acetate and hexanes afforded the title compound (0.089 g, 19%). m.p. 132-134° C. $^1$H NMR (300 MHz, $CDCl_3$) δ 8.06-8.02, 1.90-7.80, 7.75, 7.64-7.52, 7.34, 6.98, 4.05-3.33, 1.11, 1.04, 0.89-0.79, 0.50-0.46, 0.16-0.13; $^{13}$C NMR (75 MHz, $CDCl_3$) δ 167.6, 162.7, 159.9, 145.4, 134.2, 132.3, 129.5, 127.2, 126.8, 125.4, 121.8, 112.5, 46.3, 44.6, 44.4, 40.5, 27.1, 23.5, 19.9, 18.7, 15.9; MS (ES+) m/z 462 (M+1).

EXAMPLE 24.1

6-[4-(2-Trifluoromethylbenzoyl)Piperazin-1-Yl]Pyridazine-3-Carboxylic Acid (2-Thiophen-2-Yl-Ethyl) Amide Following the procedure of Example 24, making variations only as required to use 2-thiophen-2-yl-ethylamine in place of 2,2-(dimethylcyclopropyl)methylamine to react with 6-[4-(2-trifluoromethylbenzoyl)piperazin-1-yl]pyridazine-3-carboxylic acid, the title compound was obtained as a white powder (40% yield). $^1$H NMR (300 MHz, $CDCl_3$) δ 8.01, 7.73, 7.58, 7.34, 7.12, 6.98, 6.90, 6.84, 4.03, 3.89-3.55, 3.33, 3.12. $^{13}$C NMR (75 MHz, $CDCl_3$) δ 167.6, 163.1, 160.0, 145.2, 141.1, 134.2, 132.4, 129.5, 127.2, 127.0, 126.9, 125.3, 123.9, 121.8, 112.5, 46.4, 44.6, 44.4, 41.3, 40.9, 30.9. MS (ES+) m/z 490.0 (M+1).

EXAMPLE 24.2

6-[4-(2-Trifluoromethylbenzoyl)Piperazin-1-Yl]Pyridazine-3-Carboxylic Acid (6-Chloropyridazin-3-Yl)Amide Following the procedure of Example 24, making variations only as required to use 3-amino-6-chloropyridazine in place of 2,2-(dimethylcyclopropyl)methylamine to react with 6-[4-(2-trifluoromethylbenzoyl)piperazin-1-yl]pyridazine-3-carboxylic acid, the title compound was obtained as a white powder (8% yield). $^1$H NMR (300 MHz, $CDCl_3$) δ 10.75, 8.62, 8.06, 7.75-7.50, 7.36, 7.03, 4.12-3.76, 3.36. $^{13}$C NMR (75 MHz, $CDCl_3$) δ 167.7, 162.2, 160.1, 154.0, 152.3 143.8, 134.1, 132.4, 129.7, 129.6, 127.3, 127.2, 126.94, 126.88, 126.7, 120.7, 112.2, 46.3, 44.6, 44.3, 41.3. MS (ES+) m/z 492.1 (M+1).

EXAMPLE 25

Synthesis of 6-[4-(2-Trifluoromethylbenzoyl)Piperazin-1-Yl]Pyridazine-3-Carboxylic Acid (2-Cyclopropyl-2-Oxoethyl)Amide Dess-Martin periodinane (0.55 g, 1.3 mmol) was added to a solution of 6-[4-(2-trifluoromethylbenzoyl)piperazin-1-yl] pyridazine-3-carboxylic acid (2-cyclopropyl-2-hydroxyethyl)amide (0.50 g, 1.07 mmol), the resulting reaction mixture was stirred at ambient temperature for 2 h, then diluted with ethyl acetate, sequentially washed with 10% $Na_2S_2O_3$ solution, saturated $NaHCO_3$ and brine. The organic layer was dried over anhydrous $Na_2SO_4$ and concentrated. The residue was purified by flash chromatography and recrystallized from ethyl acetate-hexanes to give the title compound in 87% yield (0.43 g). $^1$H NMR (300 MHz, $CDCl_3$) δ 8.45-8.41, 8.02, 7.72, 7.63-7.51, 7.34, 7.00, 4.48, 4.47-3.28, 2.00-1.94, 1.18-1.11, 1.10-0.82. $^{13}$C NMR (75 MHz, $CDCl_3$) δ 204.4, 167.6, 163.1, 159.8, 144.9, 134.2, 132.3, 129.5, 129.0, 127.5, 127.2, 126.9, 121.8, 118.1, 112.4, 49.5, 46.3, 44.6, 44.4, 41.2, 18.7, 11.4. MS (ES+) m/z 462.0 (M+1).

EXAMPLE 26

Synthesis of 6-[4-(2-Sulfamoylbenzoyl)Piperazin-1-Yl]Pyridazine-3-Carboxylic Acid (3-Methylbutyl) Amide To an ice-cold solution of 6-[4-(2-methanesulfonylbenzoyl)piperazin-1-yl]pyridazine-3-carboxylic acid (3-methylbutyl)amide (0.078 g, 0.17 mmol) in 5 mL of THF cooled was added methyl magnesium chloride (0.071 mL, 0.212 mmol). The resulting mixture was stirred for 15 minutes at 0° C., and then 30 minutes at ambient temperature. The reaction mixture was cooled to 0° C. again, then tributylborane (0.255 mL, 0.255 mmol) was added. The mixture was stirred at ambient temperature for 30 minutes, then heated to reflux for 18 h. After the mixture was cooled to 0° C., sodium acetate, water and hydroxylamine-o-sulfonic acid (0.067 g) were added. The mixture was stirred for 3 h, and then diluted with ethyl acetate, washed with saturated sodium bicarbonate, brine, dried and concentrated in vacuo. The residue was purified by flash column chromatography using 20% methanol in ethyl acetate to yield the title product (0.033 g, 42% yield). $^1$H NMR (300 MHz, $CDCl_3$) δ 8.58, 7.98, 7.81, 7.75-7.68, 7.64-7.58, 7.43, 7.19, 4.03-3.88, 3.78-3.59, 3.21-3.20, 3.152-3.147, 1.65-1.50, 1.46-1.35, 0.85. $^{13}$C NMR (75 MHz, $CDCl_3$) δ 170.1, 165.5, 161.7, 146.3, 139.1, 137.3, 135.5, 131.3, 130.9, 128.8, 127.9, 114.4, 45.6, 45.2, 44.96, 42.6, 39.5, 38.8, 27.1, 22.9. MS (ES+) m/z 460.1 (M+1).

EXAMPLE 27

Synthesis of 6-[4-(2-Trifluoromethylbenzoyl)Piperazin-1-Yl]Pyridazine-3-Carboxylic Acid (4-Chlorophenyl)Amide 2-Chloro-4,6-dimethoxy-1,3,5-triazine (0.105 g, 0.60 mmol) was added to a cooled (0° C.) solution of 6-[4-(2-trifluoromethylbenzoyl)piperazin-1-yl]pyridazine-3-carboxylic acid (0.190 g, 0.50 mmol) and methylmorpholine (0.07 mL, 0.63 mmol) in THF (10 mL). The reaction mixture was stirred at 0° C. for 15 min, and then at ambient temperature for 1 h. 4-Chloroaniline (0.0765 g, 0.60 mmol) was then added. After stirring at ambient temperature for 20 h, the reaction mixture was diluted with ethyl acetate (100 mL), washed with water, brine, dried over anhydrous $Na_2SO_4$ and concentrated. Purification by flash chromatography and recrystallization from ethyl acetate/hexanes afforded the title compound in 67% yield (0.164 g). $^1$H NMR (300 MHz, $CDCl_3$) δ 9.79, 8.08, 7.82-7.55, 7.36-7.28, 7.02, 4.10-4.00, 3.93-3.68, 3.35. $^{13}$C NMR (75 MHz, $CDCl_3$) δ 167.6, 160.7, 160.0, 144.8, 136.2, 134.2, 132.4, 129.5, 129.2, 129.1, 127.2, 126.9, 126.8, 126.7, 125.4, 121.8, 120.7, 112.6, 46.3, 44.5, 44.3, 41.2. MS (ES+) m/z 490.1 (M+1).

EXAMPLE 27.1

6-[4-(2-Trifluoromethylbenzoyl)Piperazin-1-Yl]Pyridazine-3-Carboxylic Acid (5-Chloropyridin-2-Yl) Amide Following the procedure of Example 27, making variations only as required to use 2-amino-5-chloropyridine in place of 4-chloroaniline, the title compound was obtained as a white powder (36% yield). $^1$H NMR (300 MHz, CDCl$_3$) δ 10.32, 8.32, 8.27, 8.08, 7.83-7.47, 7.36, 7.02, 4.11-4.03, 3.92-3.71, 3.36. $^{13}$C NMR (75 MHz, CDCl$_3$) δ 167.6, 161.4, 160.0, 149.4, 146.9, 144.4, 137.8, 134.1, 132.4, 129.5, 127.2, 126.9, 126.8, 126.7, 125.4, 121.8, 114.5, 112.2, 46.3, 44.5, 44.3, 41.2. MS (ES+) m/z 491.0 (M+1).

EXAMPLE 27.2

6-[4-(2-Trifluoromethylbenzoyl)Piperazin-1-Yl]Pyridazine-3-Carboxylic Acid (2,2-Difluoro-2-Pyridin-2-Ylethyl)Amide Following the procedure of Example 27, making variations only as required to use 2,2-difluoro-2-pyridin-2-ylethylamine in place of 4-chloroaniline, the title compound was obtained as a white powder (49%). $^1$H NMR (300 MHz, CDCl$_3$) δ 8.65, 8.27, 8.01, 7.81-7.46, 7.38-7.32, 6.96, 4.43-4.31, 4.12-3.64, 3.32. $^{13}$C NMR (75 MHz, CDCl$_3$) δ 167.6, 163.3, 159.9, 153.4, 153.1, 149.4, 144.8, 137.2, 134.2, 132.3, 129.5, 127.4, 127.2, 126.9, 126.8, 126.7, 126.3, 125.4, 125.2, 121.95, 121.81, 120.6, 120.5, 118.7, 115.5, 112.4, 46.3, 44.5, 44.4, 43.4, 43.0, 42.6, 41.2; MS (ES+) m/z 521.2 (M+1).

EXAMPLE 27.3

6-[4-(2-Trifluoromethylbenzoyl)Piperazin-1-Yl]Pyridazine-3-Carboxylic Acid (2,2-Difluoro-2-Phenylethyl)Amide Following the procedure of Example 27, making variations only as required to use 2,2-difluoro-2-phenylethylamine in place of 4-chloroaniline, the title compound was obtained as a white powder (53%). $^1$H NMR (300 MHz, CDCl$_3$) δ 8.17, 8.00, 7.71, 7.64-7.50, 7.41-7.27, 6.97, 4.17-4.01, 3.89-3.66, 3.33. $^{13}$C NMR (75 MHz, CDCl$_3$) δ 167.6, 163.2, 159.9, 144.6, 134.6, 134.1, 132.3, 130.3, 129.5, 128.5, 127.3, 127.2, 126.8, 125.3, 121.8, 120.3, 117.1, 112.4, 46.3, 45.3, 44.5, 44.3; MS (ES+) m/z 520.2 (M+1).

EXAMPLE 27.4

6-[4-(2-Trifluoromethylbenzoyl)Piperazin-1-Yl]Pyridazine-3-Carboxylic Acid [2-(3-Fluorophenyl)-2-Hydroxyethyl]Amide Following the procedure of Example 27, making variations only as required to use 2-amino-1-(3-fluorophenyl)ethanol in place of 4-chloroaniline, the title compound was obtained as a white powder (34%). m.p. 117-119° C. $^1$H NMR (300 MHz, CDCl$_3$) δ 8.25, 8.98, 7.72, 7.64-7.52, 7.35-7.23, 7.14-7.10, 6.97-6.78, 4.93, 4.05-3.31, 3.31. $^{13}$C NMR (75 MHz, CDCl$_3$) 6167.6, 164.5, 164.3, 161.3, 159.9, 144.8, 144.6, 144.5, 134.1, 132.3, 130.0, 129.9, 129.5, 127.5, 127.2, 127.1, 126.9, 126.8, 126.7, 125.4, 121.8, 121.4, 114.7, 114.4, 113.0, 112.7, 112.4, 73.1, 47.5, 47.0, 46.3, 44.5, 44.3, 41.2; MS (ES+) m/z 518.3 (M+1).

EXAMPLE 28

Synthesis of 6-[4-(2-Trifluoromethylbenzoyl) Piperazin-1-Yl]Pyridazine-3-Carboxylic Acid Pyridin-2-Ylamide To a solution of 6-[4-(2-trifluoromethylbenzoyl)piperazin-1-yl]pyridazine-3-carboxylic acid (0.400 g, 1.052 mmol) was added DMF (0.03 mL) and thionyl chloride (0.5 mL). The reaction mixture was refluxed at 70° C. for 17.5 h. The mixture was evaporated and the residue was dried overnight. The dried residue was dissolved in dichloromethane (8 mL) as an acid chloride stock solution for the next step reaction.

To a solution of 2-aminopyridine (0.038 g, 0.395 mmol) and triethylamine (0.1 mL) in dichloromethane (2 mL) was added above acid chloride stock solution (0.1315 M, 2 mL, 0.263 mmol) dropwise at ambient temperature. The reaction mixture was stirred at ambient temperature for 4 h and then diluted with ethyl acetate (100 mL), washed sequentially with water and brine. The organic layer was dried over Na$_2$SO$_4$ and evaporated. The crude product was purified by column chromatography to afford the title compound in 37% yield (0.044 g). $^1$H NMR (300 MHz, CDCl$_3$) δ 10.30, 8.35, 8.09, 7.75-6.69, 7.65-7.52, 7.35, 7.09-6.96, 4.10-4.02, 3.92-3.71, 3.35. $^{13}$C NMR (75 MHz, CDCl$_3$) δ 167.7, 161.5, 160.1, 151.1, 148.3, 144.8, 138.2, 134.2, 132.4, 129.6, 127.2, 126.9, 126.8, 125.5, 121.8, 119.9, 114.0, 112.2, 46.4, 44.6, 44.3, 41.3. MS (ES+) m/z 457.3 (M+1).

EXAMPLE 28.1

6-[4-(2-Trifluoromethylbenzoyl)Piperazin-1-Yl]Pyridazine-3-Carboxylic Acid Pyridazin-3-Ylamide Following the procedure of Example 28, making variations only as required to use pyridazin-3-ylamine in place of 2-aminopyridine to react with 6-[4-(2-trifluoromethylbenzoyl)-piperazin-1-yl]pyridazine-3-carbonyl chloride, the title compound was obtained as a white powder (17.3% yield). $^1$H NMR (300 MHz, CDCl$_3$) δ 10.81, 9.05, 8.70, 8.13, 7.87-7.57, 7.39, 6.95, 4.16-3.80, 3.40. $^{13}$C NMR (300 MHz, CDCl$_3$) δ 167.7, 162.3, 160.1, 148.6, 144.1, 132.4, 129.6, 128.1, 127.2, 126.9, 118.3, 112.1, 43.4, 44.6, 44.3, 41.3. MS (ES+) m/z 458.3 (M+1).

EXAMPLE 28.2

6-[4-(2-Trifluoromethylbenzoyl)Piperazin-1-Yl]Pyridazine-3-Carboxylic Acid (2-Pyridin-2-Ylethyl) Amide Following the procedure of Example 28, making variations only as required to use 2-pyridin-2-ylethylamine in place of 2-aminopyridine to react with 6-[4-(2-trifluoromethyl-benzoyl)piperazin-1-yl]pyridazine-3-carbonyl chloride, the title compound was obtained as a white powder (30%). m.p. 151-154° C. $^1$H NMR (300 MHz, DMSO-d$_6$) δ 9.07, 8.78, 8.43, 7.99-7.61, 7.52, 7.34, 3.79-3.60, 3.35-3.14. MS (ES+) m/z 485.3 (M+1).

EXAMPLE 29

Synthesis of 6-[4-(2-Trifluoromethylbenzoyl)Piperazin-1-Yl]Pyridazine-3-Carboxylic Acid (Benzo[1,3] Dioxol-5-Yl-Methyl)Amide A. A solution of 6-[4-(2-trifluoromethylbenzoyl)piperazin-1-yl]pyridazine-3-carboxylic acid (0.300 g, 0.789 mmol) in dichloromethane (12 mL) and THF (6 mL) was cooled to 0° C. N-Methylmorpholine (0.806 g, 0.789 mmol) was charged, followed by dropwise addition of isobutyl chloroformate (0.109 g, 0.789 mmol). After stirred at 0° C. for 20 min and at ambient temperature for 1.5 h, the mixture was evaporated. The residue was dissolved in dichloromethane (60 mL) and the solution was cooled down to 0° C. Water (5 mL) was added to the solution at stirring. The mixture was soon trasfered into a 100 mL separation funnel. After quickly separated from water, the organic layer was evaporated at 10° C. The dry residue was then dissolved in dry dichloromethane (15 mL) and ready for next step reaction.

B. To the above mixed anhydride stock solution (0.053 M, 5 mL, 0.263 mmol) was added a solution of piperonylamine in dichloromethane (0.5 M, 0.52 mL, 0.26 mmol) drop wise at ambient temperature in 5 min. The reaction was stirred at ambient temperature for 16 h. The mixture was evaporated and dried under reduced pressure to give the title compound in 93% yield (0.136 g).

EXAMPLE 30

Synthesis of 6-[4-(2-Trifluoromethylbenzoyl)Piperazin-1-Yl]Pyridazine-3-Carboxylic Acid (Pyridin-2-Yl-Methyl)Amide A mixture of 6-[4-(2-Trifluoromethylbenzoyl)piperazin-1-yl]pyridazine-3-carboxylic acid methyl ester (0.099 g, 0.25 mmol), pyridin-2-yl-methylamine (0.7 mL) and sodium cyanide (0.245 g, 0.5 mmol) was stirred at ambient temperature overnight and purified by column chromatography to yield the title compound in 48% yield (0.057 g). m.p. 179-181° C. $^1$H NMR (300 MHz, CDCl$_3$) δ 8.81, 8.59, 8.12, 7.78-7.50, 7.37, 7.21-7.13, 6.93, 4.83, 4.17-3.66, 3.37. $^{13}$C NMR (75 MHz, CDCl$_3$) δ 167.6, 163.3, 160.0, 156.5, 149.0, 145.3, 137.0, 134.2, 132.4, 129.5, 127.2, 122.5, 121.9, 112.3, 46.4, 44.6, 44.4, 41.3. MS (ES+) m/z 471 (M+1).

EXAMPLE 30.1

6-[4-(2-Trifluoromethylbenzoyl)Piperazin-1-Yl]Pyridazine-3-Carboxylic Acid (2-Benzo[1,3]Dioxol-5-Yl-Ethyl)Amide Following the procedure of Example 30, making variations only as required to use 2-benzo[1,3]dioxol-5-ylethylamine in place of pyridin-2-ylmethylamine, the title compound was obtained as a white powder (99%). m.p. 162-164° C. $^1$H NMR (300 MHz, CDCl$_3$) δ 8.02, 7.89, 7.72, 7.64-7.51, 7.34, 6.97, 6.72-6.63, 5.89, 4.10-3.63, 3.34-3.31, 2.81. $^{13}$C NMR (75 MHz, CDCl$_3$) δ 167.6, 163, 159.9, 147.7, 146.1, 145.2, 134.2, 132.4, 132.3, 129.5, 127.2, 127.1, 126.9, 126.8, 126.7, 121.6, 112.4, 109.0, 108.4, 100.8, 46.3, 44.5, 44.4, 41.2, 40.8, 35.5. MS (ES+) m/z 528.2 (M+1).

EXAMPLE 31

Synthesis of 6-[4-(2-Trifluoromethylthiobenzoyl)Piperazin-1-Yl]-Pyridazine-3-Carboxylic Acid (2-Cyclopropylethyl)Amide A. A mixture of 4-(2-trifluoromethylbenzoyl)piperazine-1-carboxylic acid tert-butyl ester (3.58 g, 10.0 mmol) and Lawesson's reagents (2.12 g, 5.2 mmol) in toluene was heated to reflux for 4 h, and then concentrated. The residue was purified by flash column chromatography to yield 4-(2-trifluoromethylthiobenzoyl)peperazine-1-carboxylic acid tert-butyl ester (2.87 g, 76%). $^1$H NMR (300 MHz, CDCl$_3$) δ 7.64, 7.54, 7.42, 7.21, 4.53-4.45, 4.27-4.19, 3.71-3.25, 1.42.

B. A solution of 4-(2-trifluoromethylthiobenzoyl)piperazine-1-carboxylic acid tert-butyl ester (2.1 g, 5.61 mmol) in dichloromethane and trifluoroacetic acid (30 mL, 2:1) was stirred at ambient temperature overnight, the solvents were removed by evaporation. The residue was dissolved in ethyl acetate, and washed with aqueous saturated NaHCO$_3$ and brine, dried over anhydrous Na$_2$SO$_4$ and concentrated to give piperazin-1-yl-(2-trifluoromethylphenyl)methanethione (1.47 g, 5.36 mmol) which was used directly for next step without further purification.

C. A mixture of piperazin-1-yl-(2-trifluoromethylphenyl) methanethione (1.1 g, 4.0 mmol), 6-chloropyridazine-3-carboxylic acid (2-cyclopropylethyl)amide (0.98 g, 3.98 mmol), K$_2$CO$_3$ (0.83 g, 6.0 mmol) and n-Bu$_4$NI (0.010 g) in dioxane (10 mL) was heated to reflux for 21 h, and then concentrated. The residue was purified by column chromatography and recrystalization from ethyl acetate and hexanes to afford the title compound in 76% yield (1.42 g). m.p. 117-120° C. $^1$H NMR (300 MHz, CDCl$_3$) δ 8.05-7.93, 7.65, 7.55, 7.44, 7.24, 6.98, 4.61-4.40, 3.98-3.40, 1.51-1.47, 0.73-0.64, 0.44-0.35, 0.07-0.01. $^{13}$C NMR (75 MHz, CDCl$_3$) δ 197.0, 162.8, 159.6, 145.6, 140.2, 132.4, 128.8, 127.2, 127.0, 126.9, 125.5, 124.8, 124.4, 124.0, 121.8, 112.5, 50.4, 47.6, 44.2, 43.6, 40.0, 39.6, 34.4, 8.6, 4.2. MS (ES+) m/z 464.0 (M+1).

EXAMPLE 32

The following compounds are synthesized by the synthetic processes as described above:

6-[4-(2-Trifluoromethylbenzoyl)piperazin-1-yl]pyridazine-3-carboxylic acid (2-phenoxyethyl)amide;

6-[4-(2-Trifluoromethylbenzoyl)piperazin-1-yl]pyridazine-3-carboxylic acid [3-(4-fluorophenyl)propyl]amide;

1-[1-(4-Fluorophenyl)ethyl]-3-{6-[4-(2-trifluoromethylbenzoyl)piperazin-1-yl]pyridazin-3-yl}urea;

1-[3-(4-Fluorophenyl)propyl]-3-{6-[4-(2-trifluoromethylbenzoyl)piperazin-1-yl]pyridazin-3-yl}urea;

3-Cyclopentyl-N-{6-[4-(2-trifluoromethylbenzoyl)piperazin-1-yl]pyridazin-3-yl}propionamide;

6-[4-(2-Trifluoromethylbenzoyl)piperazin-1-yl]pyridazine-3-carboxylic acid phenethylamide;

6-[4-(2-Trifluoromethylbenzoyl)piperazin-1-yl]pyridazine-3-carboxylic acid (5-trifluoromethylpyridin-2-yl)amide;

6-[4-(2-Trifluoromethylbenzoyl)piperazin-1-yl]pyridazine-3-carboxylic acid (4-carbamoylphenyl)amide;

6-[4-(2-Trifluoromethylbenzoyl)piperazin-1-yl]pyridazine-3-carboxylic acid (3-carbamoylphenyl)amide;

6-[4-(2-Trifluoromethylbenzoyl)piperazin-1-yl]pyridazine-3-carboxylic acid m-tolylamide;

6-[4-(2-Trifluoromethylbenzoyl)piperazin-1-yl]pyridazine-3-carboxylic acid p-tolylamide;

6-[4-(2-Trifluoromethylbenzoyl)piperazin-1-yl]pyridazine-3-carboxylic acid o-tolylamide;

6-[4-(2-Trifluoromethylbenzoyl)piperazin-1-yl]pyridazine-3-carboxylic acid (2-propylphenyl)amide;

6-[4-(2-Trifluoromethylbenzoyl)piperazin-1-yl]-pyridazine-3-carboxylic acid (4-propylphenyl)amide;

6-[4-(2-Trifluoromethylbenzoyl)piperazin-1-yl]pyridazine-3-carboxylic acid (4-isopropylphenyl)amide;

6-[4-(2-Trifluoromethylbenzoyl)piperazin-1-yl]pyridazine-3-carboxylic acid (2-isopropylphenyl)amide;

6-[4-(2-Trifluoromethylbenzoyl)piperazin-1-yl]pyridazine-3-carboxylic acid (2-chloro-phenyl)amide;

6-[4-(2-Trifluoromethylbenzoyl)piperazin-1-yl]pyridazine-3-carboxylic acid (2-cyano-3-fluorophenyl)amide;

6-[4-(2-Trifluoromethylbenzoyl)piperazin-1-yl]pyridazine-3-carboxylic acid (2,4-dimethylphenyl)amide;

6-[4-(2-Trifluoromethylbenzoyl)piperazin-1-yl]pyridazine-3-carboxylic acid (2,5-dimethylphenyl)amide;

6-[4-(2-Trifluoromethylbenzoyl)piperazin-1-yl]pyridazine-3-carboxylic acid (2,6-dimethylphenyl)amide;

6-[4-(2-Trifluoromethylbenzoyl)piperazin-1-yl]pyridazine-3-carboxylic acid (2,3-dimethylphenyl)amide;
6-[4-(2-Trifluoromethylbenzoyl)piperazin-1-yl]pyridazine-3-carboxylic acid (3,5-dimethylphenyl)amide;
6-[4-(2-Trifluoromethylbenzoyl)piperazin-1-yl]pyridazine-3-carboxylic acid (3,4-dimethyl-phenyl)amide;
6-[4-(2-Trifluoromethylbenzoyl)piperazin-1-yl]pyridazine-3-carboxylic acid (4-ethyl-phenyl)amide;
6-[4-(2-Trifluoromethylbenzoyl)piperazin-1-yl]pyridazine-3-carboxylic acid (2-ethyl-phenyl)amide;
6-[4-(2-Trifluoromethylbenzoyl)piperazin-1-yl]pyridazine-3-carboxylic acid (3-fluoro-2-methylphenyl)amide;
6-[4-(2-Trifluoromethylbenzoyl)piperazin-1-yl]pyridazine-3-carboxylic acid (2-fluoro-4-methylphenyl)amide;
6-[4-(2-Trifluoromethylbenzoyl)piperazin-1-yl]pyridazine-3-carboxylic acid (4-fluoro-2-methylphenyl)amide;
6-[4-(2-Trifluoromethylbenzoyl)piperazin-1-yl]pyridazine-3-carboxylic acid (2-fluoro-5-methylphenyl)amide;
6-[4-(2-Trifluoromethylbenzoyl)piperazin-1-yl]pyridazine-3-carboxylic acid (3-fluoro-5-methylphenyl)amide;
6-[4-(2-Trifluoromethylbenzoyl)piperazin-1-yl]pyridazine-3-carboxylic acid (3-fluoro-phenyl)amide;
6-[4-(2-Trifluoromethylbenzoyl)piperazin-1-yl]pyridazine-3-carboxylic acid (2-fluoro-phenyl)amide;
6-[4-(2-Trifluoromethylbenzoyl)piperazin-1-yl]pyridazine-3-carboxylic acid (4-fluoro-phenyl)amide;
6-[4-(2-Trifluoromethylbenzoyl)piperazin-1-yl]pyridazine-3-carboxylic acid (2,4-difluorophenyl)amide;
6-[4-(2-Trifluoromethylbenzoyl)piperazin-1-yl]pyridazine-3-carboxylic acid (2,5-difluorophenyl)amide;
6-[4-(2-Trifluoromethylbenzoyl)piperazin-1-yl]pyridazine-3-carboxylic acid (3,4-difluorophenyl)amide;
6-[4-(2-Trifluoromethylbenzoyl)piperazin-1-yl]pyridazine-3-carboxylic acid (2,3-difluorophenyl)amide;
6-[4-(2-Trifluoromethylbenzoyl)piperazin-1-yl]pyridazine-3-carboxylic acid (2,6-difluorophenyl)amide;
6-[4-(2-Trifluoromethylbenzoyl)piperazin-1-yl]pyridazine-3-carboxylic acid (7H-purin-6-yl)amide;
6-[4-(2-Trifluoromethylbenzoyl)piperazin-1-yl]pyridazine-3-carboxylic acid pyrazin-2-ylamide;
6-[4-(2-Trifluoromethylbenzoyl)piperazin-1-yl]pyridazine-3-carboxylic acid indan-1-ylamide;
6-[4-(2-Trifluoromethylbenzoyl)piperazin-1-yl]pyridazine-3-carboxylic acid (1H-tetrazol-5-yl)amide;
6-[4-(2-Trifluoromethylbenzoyl)piperazin-1-yl]pyridazine-3-carboxylic acid (2H-[1,2,4]triazol-3-yl)amide;
6-[4-(2-Trifluoromethylbenzoyl)piperazin-1-yl]pyridazine-3-carboxylic acid (3-methyl-isoxazol-5-yl)amide;
6-[4-(2-Trifluoromethylbenzoyl)piperazin-1-yl]pyridazine-3-carboxylic acid (5-methyl-isoxazol-3-yl)amide;
6-[4-(2-Trifluoromethylbenzoyl)piperazin-1-yl]pyridazine-3-carboxylic acid (1H-pyrazol-3-yl)amide;
6-[4-(2-Trifluoromethylbenzoyl)piperazin-1-yl]pyridazine-3-carboxylic acid (5-methyl-1H-pyrazol-3-yl)amide;
6-[4-(2-Trifluoromethylbenzoyl)piperazin-1-yl]pyridazine-3-carboxylic acid pyrimidin-2-ylamide;
6-[4-(2-Trifluoromethylbenzoyl)piperazin-1-yl]pyridazine-3-carboxylic acid pyrazin-2-ylamide;
6-[4-(2-Trifluoromethylbenzoyl)piperazin-1-yl]pyridazine-3-carboxylic acid (4-methyl-pyrimidin-2-yl)amide;
6-[4-(2-Trifluoromethylbenzoyl)piperazin-1-yl]pyridazine-3-carboxylic acid (2-oxo-2,3-dihydropyrimidin-4-yl)amide;
6-[4-(2-Trifluoromethylbenzoyl)piperazin-1-yl]pyridazine-3-carboxylic acid (6-oxo-1,6-dihydropyrimidin-2-yl)amide;
6-[4-(2-Trifluoromethylbenzoyl)piperazin-1-yl]pyridazine-3-carboxylic acid (2-oxo-1,3-diazabicyclo[3.1.0]hex-3-en-4-yl)amide;
6-[4-(2-Trifluoromethylbenzoyl)piperazin-1-yl]pyridazine-3-carboxylic acid (5-oxo-4,5-dihydro-1H-pyrazol-3-yl)amide;
6-[4-(2-Trifluoromethylbenzoyl)piperazin-1-yl]pyridazine-3-carboxylic acid [1,3,4]thiadiazol-2-ylamide;
6-[4-(2-Trifluoromethylbenzoyl)piperazin-1-yl]pyridazine-3-carboxylic acid thiazol-2-ylamide;
6-[4-(2-Trifluoromethylbenzoyl)piperazin-1-yl]pyridazine-3-carboxylic acid indan-5-ylamide;
6-[4-(2-Trifluoromethyl-benzoyl)piperazin-1-yl]pyridazine-3-carboxylic acid pyridin-2-ylamide;
6-[4-(2-Trifluoromethylbenzoyl)piperazin-1-yl]pyridazine-3-carboxylic acid pyridin-3-ylamide;
6-[4-(2-Trifluoromethylbenzoyl)piperazin-1-yl]pyridazine-3-carboxylic acid pyridin-4-ylamide;
6-[4-(2-Trifluoromethylbenzoyl)piperazin-1-yl]pyridazine-3-carboxylic acid (6-oxo-1,6-dihydro[1,3,5]triazin-2-yl)amide;
6-[4-(2-Trifluoromethylbenzoyl)piperazin-1-yl]pyridazine-3-carboxylic acid (5-fluoro-pyridin-2-yl)amide;
6-[4-(2-Trifluoromethylbenzoyl)piperazin-1-yl]pyridazine-3-carboxylic acid (4-cyano-phenyl)amide;
6-[4-(2-Trifluoromethylbenzoyl)piperazin-1-yl]pyridazine-3-carboxylic acid (2-cyano-phenyl)amide;
6-[4-(2-Trifluoromethylbenzoyl)piperazin-1-yl]pyridazine-3-carboxylic acid (3-cyano-phenyl)amide;
6-[4-(2-Trifluoromethylbenzoyl)piperazin-1-yl]pyridazine-3-carboxylic acid (5-cyano-pyridin-2-yl)amide;
6-[4-(2-Trifluoromethylbenzoyl)piperazin-1-yl]pyridazine-3-carboxylic acid (4,6-dimethylpyrimidin-2-yl)amide;
6-[4-(2-Trifluoromethylbenzoyl)piperazin-1-yl]pyridazine-3-carboxylic acid (2-chloro-pyridin-4-yl)amide;
6-[4-(2-Trifluoromethylbenzoyl)piperazin-1-yl]pyridazine-3-carboxylic acid (1H-indol-6-yl)-amide;
6-[4-(2-Trifluoromethylbenzoyl)piperazin-1-yl]pyridazine-3-carboxylic acid (1H-indol-4-yl)amide;
6-[4-(2-Trifluoromethylbenzoyl)piperazin-1-yl]pyridazine-3-carboxylic acid (1H-indazol-5-yl)amide;
6-[4-(2-Trifluoromethylbenzoyl)piperazin-1-yl]pyridazine-3-carboxylic acid (1H-indazol-6-yl)amide;
6-[4-(2-Trifluoromethylbenzoyl)piperazin-1-yl]pyridazine-3-carboxylic acid (4-methyl-thiazol-2-yl)amide;
6-[4-(2-Trifluoromethylbenzoyl)piperazin-1-yl]pyridazine-3-carboxylic acid (5-methyl-thiazol-2-yl)amide;
6-[4-(2-Trifluoromethylbenzoyl)piperazin-1-yl]pyridazine-3-carboxylic acid (5-thioxo-4,5-dihydro-1H-[1,2,4]triazol-3-yl)amide;
6-[4-(2-Trifluoromethylbenzoyl)piperazin-1-yl]pyridazine-3-carboxylic acid (1H-benzoimidazol-2-yl)amide;
6-[4-(2-Trifluoromethylbenzoyl)piperazin-1-yl]pyridazine-3-carboxylic acid (6-methylpyridazin-3-yl)amide;
6-[4-(2-Trifluoromethylbenzoyl)piperazin-1-yl]pyridazine-3-carboxylic acid (6-methoxypyridazin-3-yl)amide;
6-[4-(2-Trifluoromethylbenzoyl)piperazin-1-yl]pyridazine-3-carboxylic acid (3-chloro-phenyl)amide;
6-[4-(2-Trifluoromethylbenzoyl)piperazin-1-yl]pyridazine-3-carboxylic acid (3-chloro-2-methylphenyl)amide;
6-[4-(2-Trifluoromethylbenzoyl)piperazin-1-yl]pyridazine-3-carboxylic acid (2-chloro-3-methylphenyl)amide;

6-[4-(2-Trifluoromethylbenzoyl)piperazin-1-yl]pyridazine-3-carboxylic acid (2,5-dichlorophenyl)amide;
6-[4-(2-Trifluoromethylbenzoyl)piperazin-1-yl]pyridazine-3-carboxylic acid (2-chloro-5-methylphenyl)amide;
6-[4-(2-Trifluoromethylbenzoyl)piperazin-1-yl]pyridazine-3-carboxylic acid (2-chloro-6-methylphenyl)amide;
6-[4-(2-Trifluoromethylbenzoyl)piperazin-1-yl]pyridazine-3-carboxylic acid (4-chloro-2-methylphenyl)amide;
6-[4-(2-Trifluoromethylbenzoyl)piperazin-1-yl]pyridazine-3-carboxylic acid (4-chloro-3-methylphenyl)amide;
6-[4-(2-Trifluoromethylbenzoyl)piperazin-1-yl]pyridazine-3-carboxylic acid (3-chloro-4-methylphenyl)amide;
6-[4-(2-Trifluoromethylbenzoyl)piperazin-1-yl]pyridazine-3-carboxylic acid (2-chloro-4-methylphenyl)amide;
6-[4-(2-Trifluoromethylbenzoyl)piperazin-1-yl]pyridazine-3-carboxylic acid (2-chloro-5-fluorophenyl)amide;
6-[4-(2-Trifluoromethylbenzoyl)piperazin-1-yl]pyridazine-3-carboxylic acid (5-chloro-2-fluorophenyl)amide;
6-[4-(2-Trifluoromethylbenzoyl)piperazin-1-yl]pyridazine-3-carboxylic acid (2,5-difluorophenyl)amide;
6-[4-(2-Trifluoromethylbenzoyl)piperazin-1-yl]pyridazine-3-carboxylic acid (2,6-dichlorophenyl)amide;
6-[4-(2-Trifluoromethylbenzoyl)piperazin-1-yl]pyridazine-3-carboxylic acid (2-trifluoromethylphenyl)amide;
6-[4-(2-Trifluoromethylbenzoyl)piperazin-1-yl]pyridazine-3-carboxylic acid (4-trifluoromethylphenyl)amide;
6-[4-(2-Trifluoromethylbenzoyl)-piperazin-1-yl]pyridazine-3-carboxylic acid (3-trifluoromethylphenyl)amide;
6-[4-(2-Trifluoromethylbenzoyl)piperazin-1-yl]pyridazine-3-carboxylic acid phenylamide;
6-[4-(2-Trifluoromethylbenzoyl)piperazin-1-yl]pyridazine-3-carboxylic acid (5-chloro-2-methoxyphenyl) amide;
6-[4-(2-Trifluoromethylbenzoyl)piperazin-1-yl]pyridazine-3-carboxylic acid (2,5-dimethoxyphenyl)amide;
6-[4-(2-Trifluoromethylbenzoyl)piperazin-1-yl]pyridazine-3-carboxylic acid (2-chloro-4-methoxyphenyl) amide;
6-[4-(2-Trifluoromethylbenzoyl)-piperazin-1-yl]pyridazine-3-carboxylic acid (4-methoxyphenyl)amide;
6-[4-(2-Trifluoromethylbenzoyl)piperazin-1-yl]pyridazine-3-carboxylic acid (2-methoxyphenyl)amide;
6-[4-(2-Trifluoromethylbenzoyl)piperazin-1-yl]pyridazine-3-carboxylic acid (3-methoxyphenyl)amide;
4-({6-[4-(2-Trifluoromethylbenzoyl)piperazin-1-yl]pyridazine-3-carbonyl}amino)-benzoic acid methyl ester;
4-({6-[4-(2-Trifluoromethylbenzoyl)piperazin-1-yl]pyridazine-3-carbonyl}amino)-benzoic acid;
2-({6-[4-(2-Trifluoromethylbenzoyl)piperazin-1-yl]pyridazine-3-carbonyl}amino)-benzoic acid methyl ester;
2-({6-[4-(2-Trifluoromethylbenzoyl)piperazin-1-yl]pyridazine-3-carbonyl}amino)-benzoic acid;
6-[4-(2-Trifluoromethylbenzoyl)piperazin-1-yl]pyridazine-3-carboxylic acid (3,4-dichlorophenyl)amide;
1-[1-(4-Fluorophenyl)ethyl]-3-{6-[4-(2-trifluoromethylbenzoyl)piperazin-1-yl]-pyridazin-3-yl}urea.

EXAMPLE 33

Measuring Stearoyl-CoA Desaturase Inhibition Activity of a Test Compound Using Mouse Liver Microsomes The identification of compounds of the invention as SCD inhibitors was readily accomplished using the SCD enzymes and microsomal assay procedure described in Brownlie et al, PCT published patent application, WO 01/62954.

Preparation of Mouse Liver Microsomes:

Male ICR mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 1.5 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Reactions are started by adding 2 mg of microsomal protein to pre-incubated tubes containing 0.20 μCi of the substrate fatty acid (1-$^{14}$C palmitic acid) at a final concentration of 33.3 μM in 1.5 ml of homogenization solution, containing 42 mM NaF, 0.33 mM niacinamide, 1.6 mM ATP, 1.0 mM NADH, 0.1 mM coenzyme A and a 10 μM concentration of test compound. The tubes are vortexed vigorously and after 15 min incubation in a shaking water bath (37° C.), the reactions are stopped and fatty acids are analyzed.

Fatty acids are analyzed as follows: The reaction mixture is saponified with 10% KOH to obtain free fatty acids which are further methylated using $BF_3$ in methanol. The fatty acid methyl esters are analyzed by high performance liquid chromatography (HPLC) using a Hewlett Packard 1090, Series II chromatograph equipped with a diode array detector set at 205 nm, a radioisotope detector (Model 171, Beckman, Calif.) with a solid scintillation cartridge (97% efficiency for $^{14}$C-detection) and a reverse-phase ODS (C-18) Beckman column (250 mm×4.6 mm i.d.; 51m particle size) attached to a pre-column with a μBondapak C-18 (Beckman) insert. Fatty acid methyl esters are separated isocratically with acetonitrile/water (95:5 v:v) at a flow rate of 1 mL/min and are identified by comparison with authentic standards. Alternatively, fatty acid methyl esters may be analyzed by capillary column gas-chromatography (GC) or Thin Layer Chromatography (TLC).

Those skilled in the art are aware of a variety of modifications to this assay that can be useful for measuring inhibition of stearoyl-CoA desaturase activity in microsomes by test compounds.

Representative compounds of the invention showed activity as inhibitors of SCD when tested in this assay. The activity was defined in terms of % SCD enzyme activity remaining at the desired concentration of the test compound.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An in vivo method of inhibiting human stearoyl-CoA desaturase (hSCD) activity comprising contacting a source of hSCD with a compound of formula (Ia)

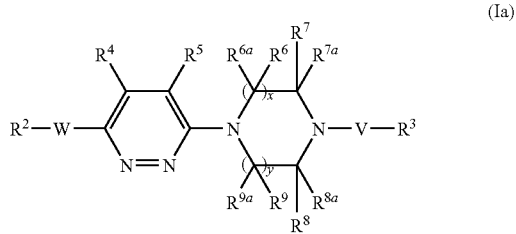

(Ia)

wherein:

x and y are each independently 1, 2 or 3;

W is —C(O)N($R^1$)—; —C(O)N[C(O)$R^{1a}$]—, —N($R^1$)C(O)N($R^1$)— —N($R^1$)C(O)—, —OC(O)N($R^1$)—, —N($R^1$)S(O)$_p$—(where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—, —N($R^1$)C(=N$R^{1a}$)N($R^1$)—, —N($R^1$)C(=S)N($R^1$)—, —N($R^1$)C(=N$R^{1a}$)—, or —C(=N$R^{1a}$)N($R^1$)—;

V is —C(O)—, —C(O)O—, —C(S)—, —C(O)N($R^1$)—, —S(O)$_t$— (where t is 0, 1 or 2), —S(O)$_p$N($R^1$)— (where p is 1 or 2), —C($R^{10}$)H—, or —C(=N$R^{1a}$)—;

each $R^1$ is independently selected from the group consisting of hydrogen; $C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;

$R^{1a}$ is selected from the group consisting of hydrogen, —O$R^1$, cyano, $C_1$-$C_6$alkyl and cycloalkylalkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —N($R^{12}$)$_2$;

or $R^6$ and $R^{6a}$ together, or $R^7$ and $R^{7a}$ together, or $R^8$ and $R^{8a}$ together, or $R^9$ and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

a stereoisomer, enantiomer or tautomer thereof, a pharmaceutically acceptable salt thereof, a pharmaceutical composition thereof.

2. A compound of formula (Ia):

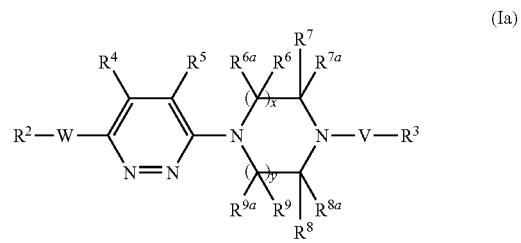

(Ia)

wherein:

x and y are each independently 1, 2 or 3;

W is —C(O)N($R^1$)—; —C(O)N[C(O)$R^{1a}$]—, —N($R^1$)C(O)N($R^1$)— —N($R^1$)C(O)—, —OC(O)N($R^1$)—, —N($R^1$)S(O)$_p$(where p is 1 or 2), —S(O)$_p$N($R^1$)— (where p is 1 or 2), —C(O)—, —OS(O)$_2$N($R^1$)—, —OC(O)—, —C(O)O—, —N($R^1$)C(O)O—, —N($R^1$)C(=N$R^{1a}$)N($R^1$)—, —N($R^1$)C(=S)N($R^1$)—, —N($R^1$)C(=N$R^{1a}$)—, or —C(=N$R^{1a}$)N($R^1$)—;

V is —C(O)—, —C(O)O—, —C(S)—, —C(O)N($R^1$)—, —S(O)$_t$— (where t is 0, 1 or 2) —S(O)$_p$N($R^1$)— (where p is 1 or 2), —C($R^{10}$)H—, or —C(=N$R^{1a}$)—;

each $R^1$ is independently selected from the group consisting of hydrogen;

$C_1$-$C_6$alkyl optionally substituted with one or more substituents selected from the group consisting of halo, methyl or trifluoromethyl; and $C_2$-$C_6$alkyl optionally substituted with one or more substituents selected from the group consisting of methoxy and hydroxyl;

$R^{1a}$ is selected from the group consisting of hydrogen, —O$R^1$, cyano, $C_1$-$C_6$alkyl and cycloalkylalkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_{12}$alkoxy, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —$N(R^{12})_2$;

$R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$$R^9$, and $R^{9a}$ are each independently selected from hydrogen or $C_1$-$C_3$alkyl;

$R^{10}$ is hydrogen or $C_1$-$C_3$alkyl; and each $R^{12}$ is independently selected from hydrogen or $C_1$-$C_6$alkyl;

a stereoisomer, enantiomer or tautomer thereof, a pharmaceutically acceptable salt thereof, a pharmaceutical composition thereof.

3. The compound of claim 2 wherein W is —$N(R^1)C(O)$— and V is —$C(=NH)$—.

4. The compound of claim 2 wherein W is —$N(R^1)C(=NR^{1a})$—.

5. The compound of claim 2 wherein W is —$N(R^1)C(=NR^{1a})N(R^1)$— or —$N(R^1)C(=S)N(R^1)$—.

6. A pharmaceutical composition comprising a pharmaceutically acceptable excipient and a therapeutically effective amount of a compound of claim 2.

* * * * *